(12) United States Patent
Sherman et al.

(10) Patent No.: US 7,131,987 B2
(45) Date of Patent: Nov. 7, 2006

(54) MICROSTRUCTURES AND METHOD FOR TREATING AND CONDITIONING SKIN WHICH CAUSE LESS IRRITATION DURING EXFOLIATION

(75) Inventors: Faiz Feisal Sherman, West Chester, OH (US); Vladimir Gartstein, Cincinnati, OH (US)

(73) Assignee: Corium International, Inc., Redwood City, CA (US)

( * ) Notice: Subject to any disclaimer, the term of this patent is extended or adjusted under 35 U.S.C. 154(b) by 766 days.

(21) Appl. No.: 10/154,686

(22) Filed: May 24, 2002

(65) Prior Publication Data

US 2002/0177858 A1 Nov. 28, 2002

Related U.S. Application Data

(63) Continuation-in-part of application No. 09/952,403, filed on Sep. 14, 2001, now Pat. No. 6,821,281.

(60) Provisional application No. 60/240,730, filed on Oct. 16, 2000, provisional application No. 60/240,787, filed on Oct. 16, 2000.

(51) Int. Cl.
  *H61M 35/00* (2006.01)
(52) U.S. Cl. ........................ 606/290; 606/131
(58) Field of Classification Search ................ 600/556; 604/46, 47, 48, 289, 290; 606/131, 132, 606/133
See application file for complete search history.

(56) References Cited

U.S. PATENT DOCUMENTS

| | | | |
|---|---|---|---|
| 1,554,510 A * | 9/1925 | Kirby | .............. 15/188 |
| 3,918,449 A | 11/1975 | Pistor | |
| 3,964,482 A | 6/1976 | Gerstel et al. | |
| 4,055,029 A | 10/1977 | Kalbow | |
| 4,151,240 A * | 4/1979 | Lucas et al. | ................ 264/504 |
| 4,180,232 A | 12/1979 | Hardigg | |
| 4,381,963 A | 5/1983 | Goldstein et al. | |

(Continued)

FOREIGN PATENT DOCUMENTS

DE 23195591 11/1974

(Continued)

OTHER PUBLICATIONS

Mcallister, H., "Micromachined Microneedles for Transdermal Drug Delivery", Allen & Prausnitz, Georgia Institute of Technology, Atlanta, GA.

(Continued)

*Primary Examiner*—Anh Tuan Nguyen
*Assistant Examiner*—Nguyen Victor
(74) *Attorney, Agent, or Firm*—Reed Intellectual Property Law Group

(57) ABSTRACT

An improved method is provided to enhance skin appearance and health, in which skin is cleaned (or exfoliated) and conditioned by use of microelements affixed to a base element or hand-held patch. For the microstructure used in the improved method, the dimensions of the microelements are controlled so as to remove a certain number of layers of skin cells and to accumulate and retain those skin cells, along with other foreign substances, into areas between the microelements. In another embodiment of the improved method, a conditioning compound or therapeutic active can be applied to the exfoliated skin to enhance the skin. Moreover, the amount of skin cells accumulated using the improved method represents a self-limiting maximum quantity that cannot be substantially exceeded regardless of the number of attempts by a user to re-use the microstructure apparatus associated with the improved method. Some of the microelement shapes are purposefully designed with distal ends that exhibit sharp edges rather than sharp tips to reduce skin irritation resulting from use of the improved method.

9 Claims, 32 Drawing Sheets

U.S. PATENT DOCUMENTS

| | | | |
|---|---|---|---|
| 4,515,168 A * | 5/1985 | Chester et al. ............... 600/554 |
| 4,585,991 A | 4/1986 | Reid et al. |
| 4,784,737 A | 11/1988 | Ray et al. |
| 4,837,049 A | 6/1989 | Byers et al. |
| 5,134,079 A | 7/1992 | Cusack et al. |
| 5,156,591 A | 10/1992 | Gross et al. |
| 5,158,073 A | 10/1992 | Bukowski |
| 5,162,043 A | 11/1992 | Lew et al. |
| 5,198,192 A | 3/1993 | Saito et al. |
| 5,215,088 A | 6/1993 | Normann et al. |
| 5,250,023 A | 10/1993 | Lee et al. |
| 5,250,067 A * | 10/1993 | Gelfer et al. ............... 606/189 |
| 5,256,360 A | 10/1993 | Li |
| 5,279,544 A | 1/1994 | Gross et al. |
| 5,318,557 A | 6/1994 | Gross |
| 5,320,600 A | 6/1994 | Lambert |
| 5,362,307 A | 11/1994 | Guy et al. |
| 5,383,512 A | 1/1995 | Jarvis |
| 5,487,726 A | 1/1996 | Rabenau et al. |
| 5,498,235 A | 3/1996 | Flower |
| 5,512,219 A | 4/1996 | Rowland et al. |
| 5,527,288 A | 6/1996 | Gross et al. |
| 5,531,675 A | 7/1996 | Yoo |
| 5,536,263 A * | 7/1996 | Rolf et al. ................. 604/307 |
| 5,551,953 A | 9/1996 | Lattin et al. |
| 5,567,376 A * | 10/1996 | Turi et al. ................. 264/455 |
| 5,591,123 A | 1/1997 | Sibalis et al. |
| 5,591,139 A | 1/1997 | Lin et al. |
| 5,611,806 A | 3/1997 | Jang |
| 5,645,977 A | 7/1997 | Wu et al. |
| 5,658,515 A | 8/1997 | Lee et al. |
| 5,676,850 A | 10/1997 | Reed et al. |
| 5,681,580 A | 10/1997 | Jang et al. |
| 5,697,901 A | 12/1997 | Eriksson |
| 5,704,520 A | 1/1998 | Gross |
| 5,711,761 A | 1/1998 | Untereker et al. |
| 5,728,089 A | 3/1998 | Lal et al. |
| 5,730,714 A | 3/1998 | Guy et al. |
| 5,735,273 A | 4/1998 | Kurnik et al. |
| 5,771,890 A | 6/1998 | Tamada |
| 5,800,420 A | 9/1998 | Gross et al. |
| 5,807,375 A | 9/1998 | Gross et al. |
| 5,814,020 A | 9/1998 | Gross |
| 5,820,622 A | 10/1998 | Gross et al. |
| 5,827,183 A | 10/1998 | Kurnik et al. |
| 5,848,985 A | 12/1998 | Muroki |
| 5,848,990 A | 12/1998 | Cirelli et al. |
| 5,848,991 A | 12/1998 | Gross et al. |
| 5,855,801 A | 1/1999 | Lin et al. |
| 5,873,849 A | 2/1999 | Bernard |
| 5,879,326 A | 3/1999 | Godshall et al. |
| 5,938,684 A | 8/1999 | Lynch et al. |
| 5,948,488 A | 9/1999 | Marecki et al. |
| 5,964,729 A | 10/1999 | Choi et al. |
| 5,983,136 A | 11/1999 | Kamen |
| 6,014,584 A | 1/2000 | Hofmann et al. |
| 6,023,629 A | 2/2000 | Tamada |
| 6,024,553 A | 2/2000 | Shimalla |
| 6,036,659 A | 3/2000 | Ray et al. |
| 6,038,465 A | 3/2000 | Melton, Jr. |
| 6,047,208 A | 4/2000 | Flower |
| 6,050,988 A | 4/2000 | Zuck |
| 6,055,453 A | 4/2000 | Hofmann et al. |
| 6,083,196 A | 7/2000 | Trautman et al. |
| 6,091,975 A | 7/2000 | Daddona et al. |
| 6,106,751 A | 8/2000 | Talbot et al. |
| 6,129,696 A | 10/2000 | Sibalis |
| 6,132,755 A | 10/2000 | Eicher et al. |
| 6,135,990 A | 10/2000 | Heller et al. |
| 6,183,434 B1 | 2/2001 | Eppstein |
| 6,216,034 B1 | 4/2001 | Hofmann et al. |
| 6,219,574 B1 | 4/2001 | Cormier et al. |
| 6,230,051 B1 | 5/2001 | Cormier et al. |
| 6,241,701 B1 | 6/2001 | Hofmann |
| 6,256,533 B1 | 7/2001 | Yuzhakov et al. |
| 6,312,612 B1 | 11/2001 | Sherman et al. |
| 6,322,808 B1 | 11/2001 | Trautman et al. |
| 6,334,856 B1 | 1/2002 | Allen et al. |
| 6,355,054 B1 | 3/2002 | Neuberger |
| 6,375,627 B1 | 4/2002 | Mauze et al. |
| 6,379,324 B1 | 4/2002 | Gartstein et al. |
| 6,440,096 B1 | 8/2002 | Lastovich et al. |
| 6,451,240 B1 | 9/2002 | Sherman et al. |
| 6,471,903 B1 | 10/2002 | Sherman et al. |
| 6,476,288 B1 | 11/2002 | Van Rijswijck et al. |
| 6,494,830 B1 | 12/2002 | Wessel |
| 6,503,231 B1 | 1/2003 | Prausnitz et al. |
| 6,511,463 B1 | 1/2003 | Wood et al. |
| 6,532,386 B1 | 3/2003 | Sun et al. |
| 6,533,884 B1 | 3/2003 | Mallik |
| 6,537,242 B1 | 3/2003 | Palmer |
| 6,537,264 B1 | 3/2003 | Cormier et al. |
| 6,558,361 B1 | 5/2003 | Yeshurun |
| 6,562,014 B1 | 5/2003 | Lin et al. |
| 6,565,532 B1 | 5/2003 | Yuzhakov et al. |
| 6,591,124 B1 | 7/2003 | Sherman et al. |
| 6,591,133 B1 | 7/2003 | Joshi |
| 6,611,706 B1 | 8/2003 | Avrahami et al. |
| 6,611,707 B1 | 8/2003 | Prausnitz et al. |
| 6,623,457 B1 | 9/2003 | Rosenberg |
| 6,629,949 B1 | 10/2003 | Douglas |
| 6,689,103 B1 | 2/2004 | Palasis |
| 6,743,211 B1 | 6/2004 | Prausnitz et al. |
| 6,767,341 B1 | 7/2004 | Cho |
| 6,770,480 B1 | 8/2004 | Canham |
| 6,778,853 B1 | 8/2004 | Heller et al. |
| 6,780,171 B1 | 8/2004 | Gabel et al. |
| 6,821,281 B1 * | 11/2004 | Sherman et al. ............ 606/131 |
| 6,835,184 B1 | 12/2004 | Sage et al. |
| 6,881,203 B1 | 4/2005 | Delmore et al. |
| 2001/0023324 A1 | 9/2001 | Pronovost et al. |
| 2002/0006355 A1 | 1/2002 | Whitson |
| 2002/0032415 A1 | 3/2002 | Trautman et al. |
| 2002/0042589 A1 | 4/2002 | Marsoner |
| 2002/0045859 A1 | 4/2002 | Gartstein et al. |
| 2002/0045907 A1 | 4/2002 | Sherman et al. |
| 2002/0082543 A1 | 6/2002 | Park et al. |
| 2002/0133129 A1 | 9/2002 | Arias et al. |
| 2002/0138049 A1 | 9/2002 | Allen et al. |
| 2002/0177839 A1 | 11/2002 | Cormier et al. |
| 2002/0177858 A1 | 11/2002 | Sherman et al. |
| 2002/0188245 A1 | 12/2002 | Martin et al. |
| 2002/0193729 A1 | 12/2002 | Cromier et al. |
| 2003/0093028 A1 | 5/2003 | Spiegel |
| 2003/0199812 A1 | 10/2003 | Rosenberg |
| 2003/0208138 A1 | 11/2003 | Olson |
| 2003/0208167 A1 | 11/2003 | Prausnitz et al. |
| 2003/0212397 A1 | 11/2003 | Avrahami et al. |
| 2004/0181203 A1 | 9/2004 | Cormier et al. |
| 2004/0186419 A1 | 9/2004 | Cho |
| 2004/0204669 A1 | 10/2004 | Hofmann |
| 2004/0220535 A1 | 11/2004 | Canham |
| 2004/0236271 A1 | 11/2004 | Theeuwes et al. |

FOREIGN PATENT DOCUMENTS

| | | |
|---|---|---|
| DE | 196 24 578 A1 | 1/1998 |
| EP | 0 312 662 A1 | 4/1989 |
| EP | 0 407 063 A1 | 1/1991 |
| EP | 0 796 128 B1 | 11/1995 |
| EP | 1 086 719 A1 | 3/2001 |
| EP | 1 174 078 A2 | 1/2002 |
| FR | 2535602 A1 | 11/1984 |
| GB | 783479 | 9/1957 |

| | | | |
|---|---|---|---|
| GB | 2221394 A | 2/1990 |
| JP | 09-051878 | 2/1997 |
| SU | 1 667 864 | 7/1991 |
| WO | WO 93/17754 A1 | 9/1993 |
| WO | WO 94/23777 A1 | 10/1994 |
| WO | WO 95/33612 A1 | 12/1995 |
| WO | WO 96/00109 A1 | 1/1996 |
| WO | WO 96/37155 A1 | 11/1996 |
| WO | WO 96/37256 A1 | 11/1996 |
| WO | WO 97/03718 A1 | 2/1997 |
| WO | WO 97/48440 A1 | 12/1997 |
| WO | WO 97/48441 A1 | 12/1997 |
| WO | WO 97/48442 A1 | 12/1997 |
| WO | WO 98/00193 A1 | 1/1998 |
| WO | WO 99/00155 A1 | 1/1999 |
| WO | WO 99/29298 A2 | 6/1999 |
| WO | WO 99/29364 A1 | 6/1999 |
| WO | WO 99/29365 A1 | 6/1999 |
| WO | WO 99/64580 A1 | 12/1999 |
| WO | WO 00/05166 A1 | 2/2000 |
| WO | WO 00/35530 A1 | 6/2000 |
| WO | WO 00/74763 A2 | 12/2000 |
| WO | WO 00/74765 A1 | 12/2000 |
| WO | WO 00/74766 A1 | 12/2000 |
| WO | WO 02/07813 A1 | 1/2002 |
| WO | WO 02/32331 A2 | 4/2002 |
| WO | WO 02/72189 A2 | 9/2002 |
| WO | WO 03/24290 A1 | 3/2003 |
| WO | WO 03/24518 A2 | 3/2003 |

OTHER PUBLICATIONS

Sebastian, H. et al., "Microfabricated Microneedles: A Novel Approach to Transdermal Drug Delivery", Journal of Pharmaceutical Sciences, Aug. 1998, pp. 922-925, vol. 87, No. 8, Atlanta, GA.

Chun, K. et al., An Array of Hollow Microcapillaries for the Controlled Injection of Genetic Materials into Animal/Plat Cells, The University of Tokyo.

Wouters, S. et al., "Microelectrochemical Systems for Drug Delivery", Electrochemica Acta., 1997, pp. 3385-3390, vol. 42, Nos. 20-22.

Prausnitz, M. R., et al., "Transdermal Delivery of Macromolecules: Recent Advances by Modification of Skin's Barrier Properties", Therapeutic Protein and Peptide Formulation and Delivery, pp. 124-153, Chapter 8, ACS Symposium Series 675, Georgia Institute of Technology.

Prausnitz, M. R., et al., Transdermal Transport Efficiency During Skin Electroporation and Iontophoresis, Journal of Controlled Release 38 , 1996, pp. 205-217, Massachusetts Institute of Technology, Cambridge, MA.

Papautsky, I. E., et al., "Micromachined Pipette Arrays (MPA)", pp. 2281-2284, Proceedings—19th International Conference—IEEE/EMBS Oct. 30-Nov. 2, 1997, Chicago, IL.

* cited by examiner

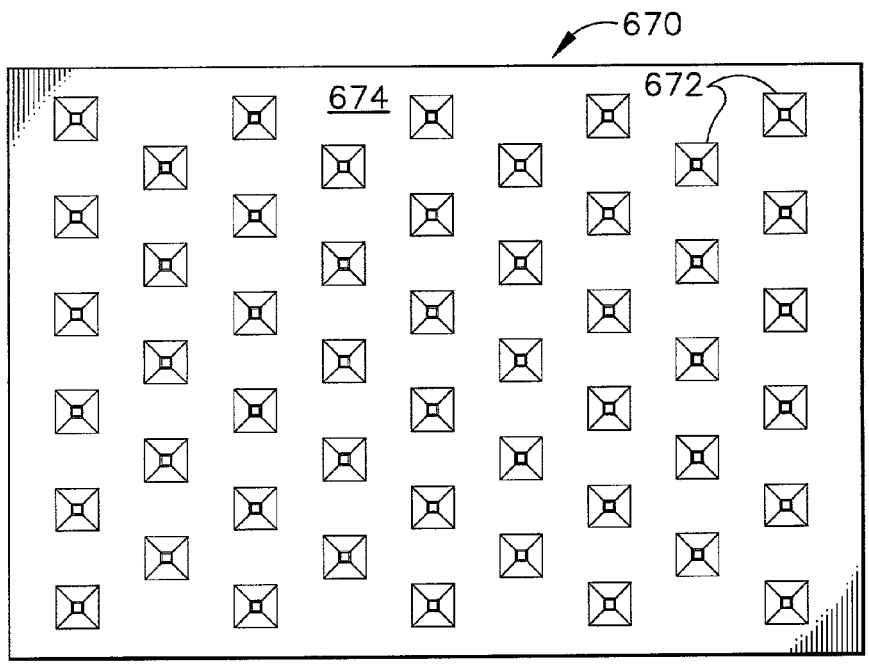
FIG. 49
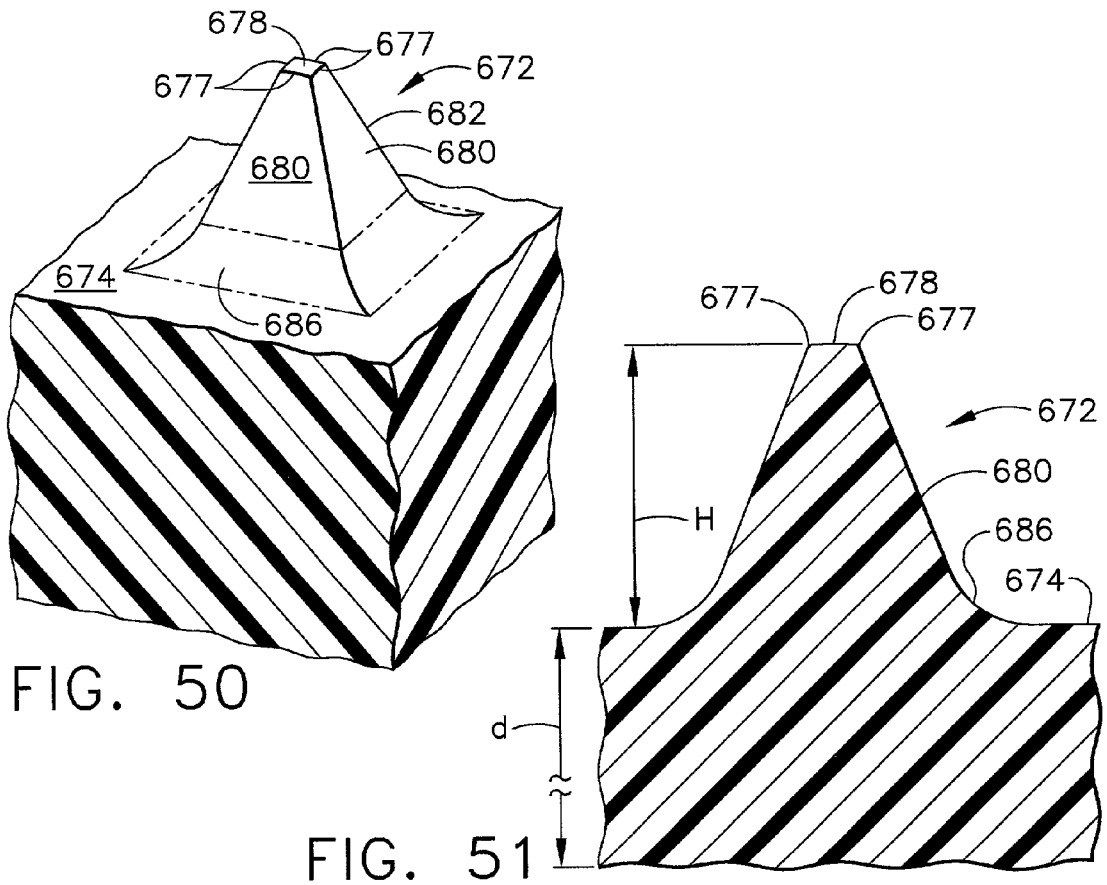
FIG. 50
FIG. 51

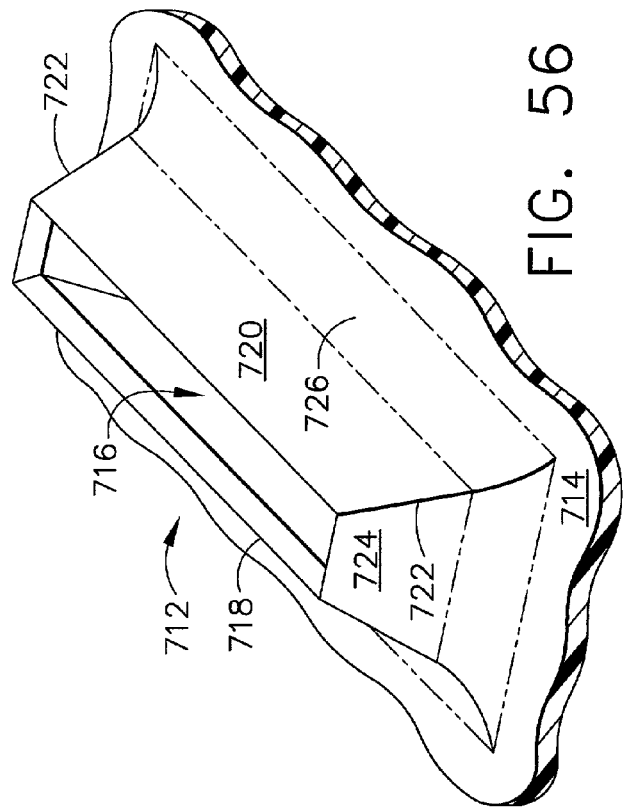
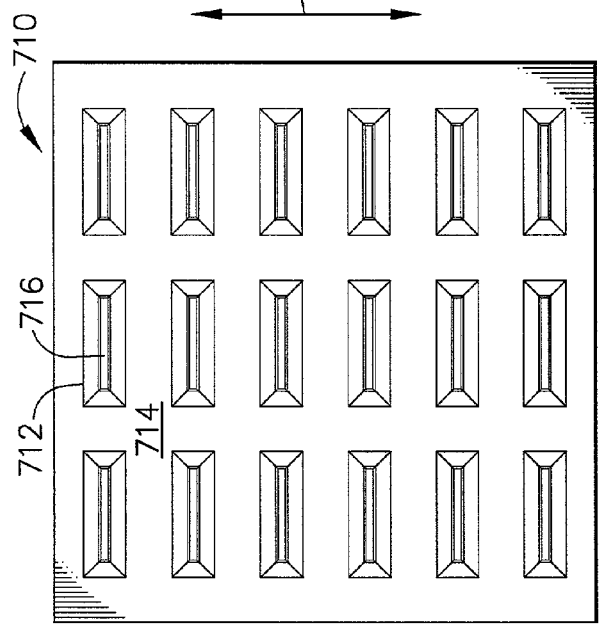
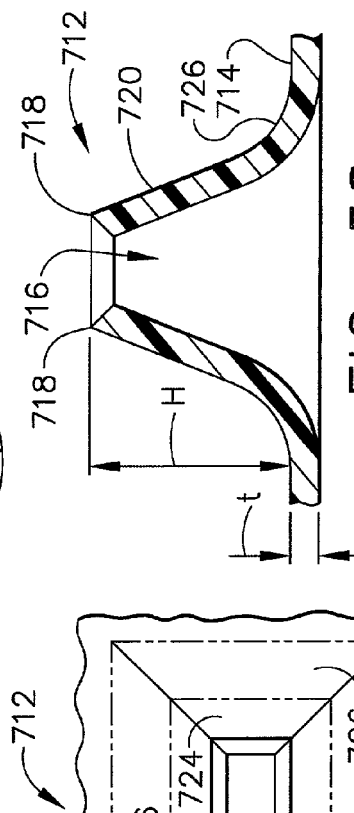
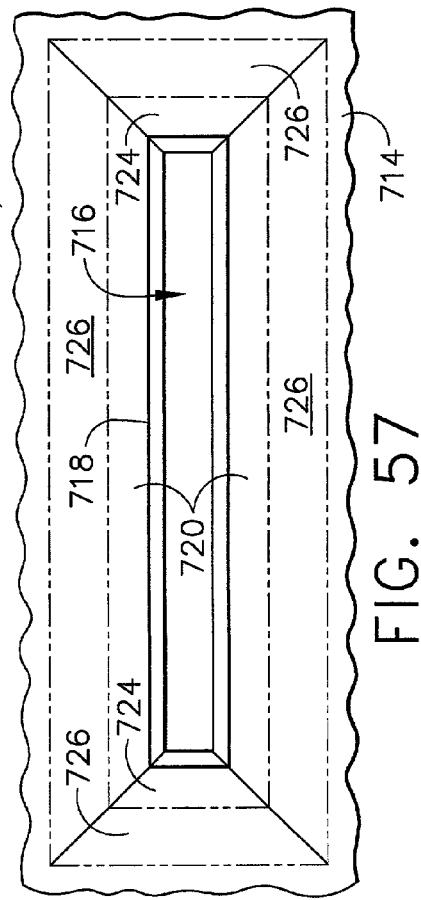

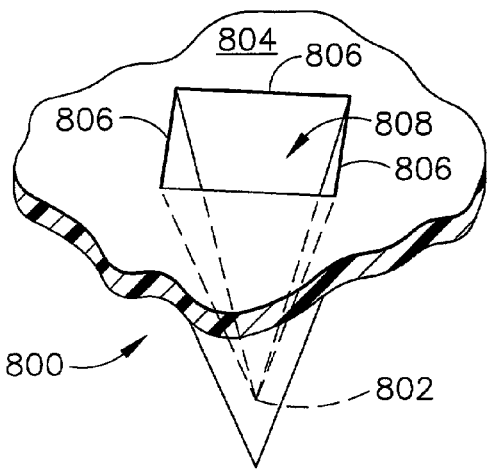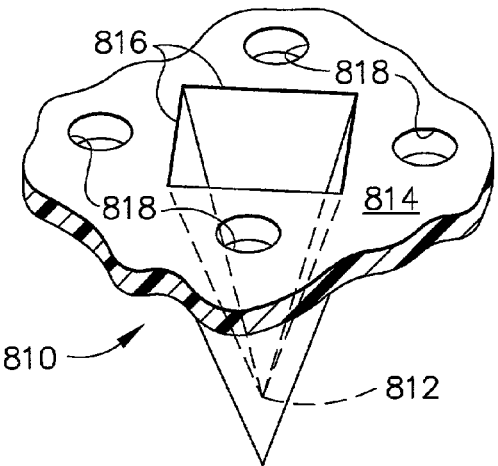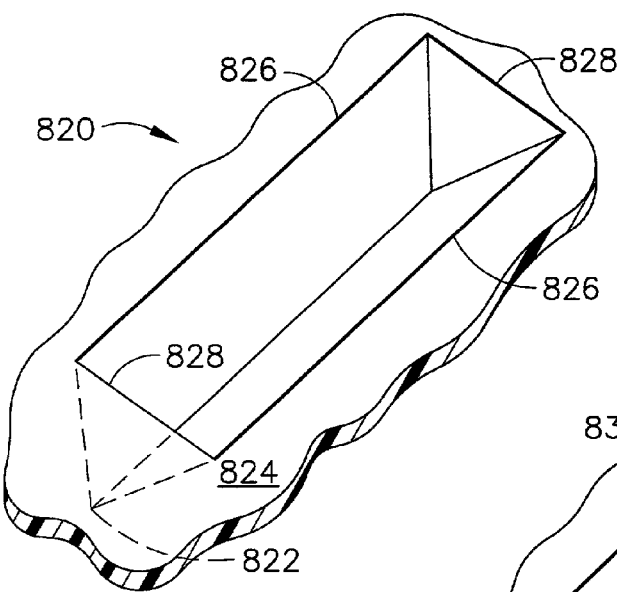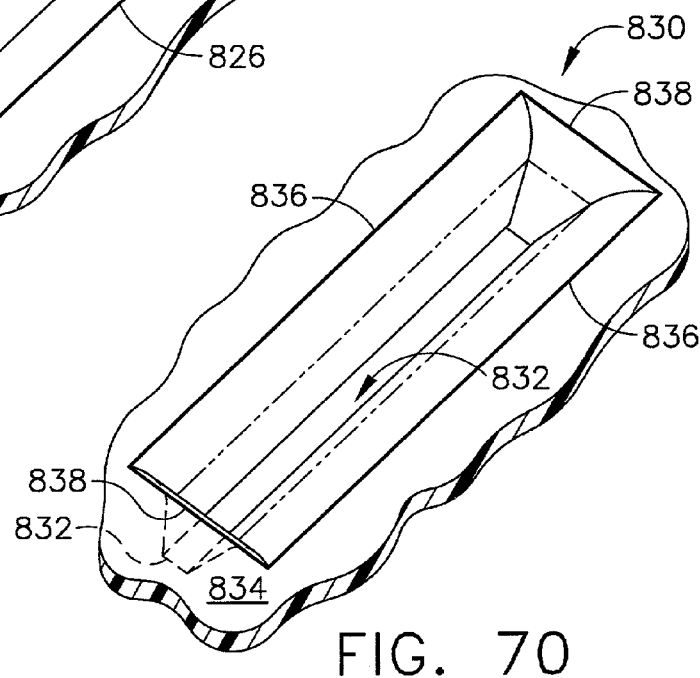

MICROSTRUCTURES AND METHOD FOR TREATING AND CONDITIONING SKIN WHICH CAUSE LESS IRRITATION DURING EXFOLIATION

CROSS-REFERENCE TO RELATED APPLICATIONS

The present application is a continuation-in-part to application Ser. No. 09/952,403, titled "Microstructures for Treating and Conditioning Skin," filed on Sep. 14, 2001, U.S. Pat. No. 6,821,281 which claims priority to U.S. provisional applications Ser. Nos. 60/240,730, filed Oct. 16, 2000, and 60/240,787, filed Oct. 16, 2000.

TECHNICAL FIELD

The present invention relates generally to systems for treating and conditioning skin and is particularly directed to an article of manufacture used to perform one or more functions such as enhancing skin, removing dead skin cells, removing accumulated make-up and cosmetics, extracting skin constituencies, depositing skin enhancing compositions, and improving skin appearance. The invention is specifically disclosed as a planar array of microelements that delivers an adjunct skin enhancement composition from at least one reservoir attached thereto, or the composition can be applied directly to skin and utilized therein in combination with the article of manufacture.

BACKGROUND OF THE INVENTION

Human skin is the largest organ. Skin and hair are the surfaces of the human body that are visible to others and the appearance of skin is important to good grooming and health. Human skin comprises several layers, the outermost is the stratum corneum, which comprises dead skin cells and makes up a substantial portion of the first protective barrier of the body. Most skin comprises a stratum corneum which is 15–20 layers of dead cells thick (about 10–20 microns in thickness). However, some "durable" skin layers, such as heels or calluses, can comprise a stratum corneum which is from 100–150 microns thick. On average, the skin naturally sheds at least one skin layer each day, and the first one to four layers of skin may be removed without affecting the protective nature of skin or the health thereof. In fact, removing up to four (4) layers of the stratum corneum may provide a skin surface area onto which make-up may be more uniformly applied and once applied has a more aesthetically pleasing appearance.

The removal of up to the first ten (10) layers of skin may also instigate resolution of and/or removal of unwanted comedones which themselves may be the result of skin pores being blocked by bacteria, dirt, dead cells, make-up, etc. The removal of skin layers in a safe and convenient manner can be indirectly accomplished in a limited manner by washing (or scrubbing) with an abrasive cloth, for example, a terry cloth sheet, but only skin cells which are about to shed are removed. However, make-up can be deposited into opened pores and if not thoroughly rinsed can leave the skin with an unwanted film of dirt, dead skin cells, oxidized oil.

There is therefore a long felt need for a system for providing enhanced skin health and appearance by helping to remove the outermost layer of human skin. There is also a need for a system which is capable of delivering to human skin one or more treatments which result in a smooth skin condition which facilitates the application of appearance enhancement compositions, cosmetics, and other materials or actives.

In conventional skin treatment or preparation methodologies, the skin cells scraped loose tend to become airborne when a mechanical scrubber is used. These airborne skin cells are distasteful at best, and could represent some type of health hazard in certain situations. In view of this situation, there further is a need to prepare skin in a manner such that most or all of the removed or "loose" skin cells do not become airborne.

In conventional skin treatment or preparation methodologies, the user has great control over the quantity of skin cells that are scraped loose from the skin, simply by rubbing harder, or by rubbing a larger (or smaller) number of strokes. This can be an undesirable situation, since the person may possibly injure himself or herself by being too vigorous, or since the person may achieve nothing by not being vigorous enough. It would be a significant improvement to provide an article of manufacture that can essentially guarantee that a predetermined maximum quantity of skin cells will be removed by application of that article on skin, such that the article's use is essentially fool-proof by virtue of its effects being self-limiting, so that only a maximum amount of skin cells can be removed, regardless of the user's very vigorous attempts to continue the rubbing strokes.

SUMMARY OF THE INVENTION

Accordingly, it is an advantage of the present invention to provide a method and apparatus that can enhance the health and the appearance of human skin.

It is another advantage of the present invention to provide an article of manufacture to treat the surface of skin, which is capable of selectively modifying the skin surface and capable of discriminately removing differential amounts of the body's outer skin layer (the stratum corneum).

It is a further advantage of the present invention to provide articles of manufacture that are capable of removing not only unwanted layers of skin, but can also be fashioned in a manner to selectively remove body hair. At the same time the skin is being conditioned, the articles of manufacture can controllably deposit one or more skin care compositions thereto or provide a skin treatment.

It is still another advantage of the present invention to provide articles of manufacture which can deliver a metered amount of a composition, remove a specific number of cellular layers (e.g., skin layers), and the like; the articles of manufacture can also be made for any type of onetime treatment after which the individual article is disposed of.

It is yet another advantage of the present invention to provide an article of manufacturer that can deliver a metered amount of a composition and remove a specific number of cellular layers (e.g., skin layers), and can do so by use of microelements that are not substantially sharp at their most distal ends from the substrate to which the microelements are mounted, thereby causing less irritation to the skin surface as compared to microelements having very sharp distal ends.

It is still another advantage of the present invention to provide a microstructure apparatus in which a large number of closely-packed microelements are placed on a substrate; when the microstructure is placed against skin and rubbed thereagainst to perform an exfoliation procedure, then skin cells (and perhaps vellus hair) are removed from the skin and accumulate in the spaces between the side walls of the microelements, such that a large majority of the scraped skin cells (and other matter) are removed when the microstructure apparatus is withdrawn from the skin.

Additional advantages and other novel features of the invention will be set forth in part in the description that follows and in part will become apparent to those skilled in the art upon examination of the following or may be learned with the practice of the invention.

To achieve the foregoing and other advantages, and in accordance with one aspect of the present invention, a method for removing cells from skin is provide, in which the method comprises the steps of: (1) providing a microstructure having a substrate and a plurality of microelements; (2) placing the microstructure on skin then rubbing the microstructure against the skin, thereby scraping and accumulating skin cells on the substrate in areas between the plurality of microelements; and (3) withdrawing the microstructure from the skin, and thereby removing a large majority of the skin cells that have accumulated upon the substrate.

In accordance with another aspect of the present invention, a microstructure apparatus is provided, which comprises: (1) a substrate and a plurality of microelements affixed upon a first surface of the substrate; (2) the plurality of microelements being of a predetermined size and shape so as to scrape a substantially predetermined quantity of skin cells from skin when the microstructure apparatus is placed upon the skin and moved in at least one predetermined direction; and (3) the plurality of microelements being spaced-apart from one another upon the substrate by a predetermined distances so as to remove a large majority of the scraped skin cells when the microstructure apparatus is withdrawn from the skin.

The present invention relates further relates to embodiments of the article of manufacture which allows simultaneous delivery of a skin-enhancing composition in conjunction with removing one or more constituents of skin or modifying the skin surface for further treatment. Such a skin-enhancing composition could include both a biological active and a chemical active.

In accordance with yet another aspect of the present invention, a method for removing cells from skin is provided, in which the method comprises the steps of: (1) providing a microstructure having a substrate and a plurality of microelements, wherein a majority of the microelements are of at least one predetermined shape that includes at least one substantially sharp edge at a distal end of the microelements; (2) placing the microstructure on skin, then rubbing the microstructure against the skin, thereby scraping and accumulating skin cells on the substrate in areas between the plurality of microelements, wherein the predetermined shape of the majority of microelements does not create substantial focal discrete points of pressure on skin; and (3) withdrawing the microstructure from the skin, and thereby removing a large majority of the skin cells that have accumulated upon the substrate.

In accordance with a further aspect of the present invention, a method for removing cells from skin is provided, in which the method comprises the steps of: (1) providing a microstructure having a substrate and a plurality of inverted microelements, wherein a majority of the microelements extends from a first surface of the substrate and which exhibit a substantially empty space within the microelements, and wherein the majority of the microelements exhibits at least one substantially sharp edge along a second surface of the substrate, the second surface being opposite the first surface of the substrate; (2) placing the second surface of the microstructure on skin and then rubbing the microstructure against the skin, thereby scraping and accumulating skin cells within the substantially empty space within the majority of microelements; and (3) withdrawing the microstructure from the skin, and thereby removing a large majority of the skin cells that have accumulated within the substantially empty space within the majority of microelements.

In accordance with yet a further another aspect of the present invention, a method for removing cells from skin is provided, in which the method comprises the steps of: (1) providing a microstructure having a substrate and a plurality of microelements, wherein a majority of the microelements are of at least one predetermined size and shape, and exhibit at least one side wall that extends above the first surface of the substrate, and wherein the majority of microelements are oriented in a closely-packed arrangement such that any spacing between side walls of adjacent microelements is substantially minimized; (2) placing the microstructure on skin then rubbing the microstructure against the skin, thereby scraping and accumulating skin cells in areas between the plurality of microelements; and (3) withdrawing the microstructure from the skin, and thereby removing a large majority of the skin cells that have accumulated upon the microstructure.

In accordance with still another aspect of the present invention, a microstructure apparatus is provided, which comprises: a substrate and a plurality of microelements affixed upon a first surface of the substrate; the plurality of microelements being of predetermined sizes and shapes for use in scraping skin cells from skin when the microstructure apparatus is placed upon the skin and moved in at least one direction, the microelement predetermined sizes and shapes including at least one substantially sharp edge at a distal end of the microelements, and the microelement predetermined sizes and shapes having a characteristic such that the microelements do not create substantial focal discrete points of pressure on the skin.

In accordance with a further aspect of the present invention, a microstructure apparatus is provided, which comprises: a substrate and a plurality of microelements affixed upon a first surface of the substrate; the plurality of microelements being of predetermined sizes and shapes for use in scraping skin cells from skin when the microstructure apparatus is placed upon the skin and moved in at least one direction; the plurality of microelements each having at least one side wall that extends above the first surface of the substrate; and wherein the plurality of microelements are oriented in a closely-packed arrangement such that any spacing between side walls of adjacent microelements is substantially minimized.

In accordance with yet a further aspect of the present invention, a microstructure apparatus is provided, which comprises: a substrate and a plurality of inverted microelements that extend from a first surface of the substrate, the microelements exhibiting a substantially empty space therewithin, and wherein the microelements exhibit at least one substantially sharp edge along a second surface of the substrate, the second surface being opposite the first surface of the substrate; and the at least one substantially sharp edge being of a predetermined size and shape for use in scraping skin cells from skin when the second surface of the microstructure apparatus is placed upon the skin and moved in at least one direction.

Still other advantages of the present invention will become apparent to those skilled in this art from the following description and drawings wherein there is described and shown a preferred embodiment of this invention in one of the best modes contemplated for carrying out the invention. As will be realized, the invention is capable of other different embodiments, and its several details are capable of modification in various, obvious aspects all without departing from the invention. Accordingly, the drawings and descriptions will be regarded as illustrative in nature and not as restrictive.

All percentages, ratios and proportions herein are by weight, unless otherwise specified. All temperatures are in degrees Celsius (° C.) unless otherwise specified. All documents cited are in relevant part, incorporated herein by reference.

BRIEF DESCRIPTION OF THE DRAWINGS

The accompanying drawings incorporated in and forming a part of the specification illustrate several aspects of the present invention, and together with the description and claims serve to explain the principles of the invention. In the drawings:

FIG. 49 is a plan view of an array of microelements that are partially pyramidal in shape and more elongated, but which are solid in form, as constructed according to the principles of the present invention.

FIG. 50 is a perspective view of one of the partially-pyramidal microelements of FIG. 49.

FIG. 51 is a side elevational view in cross-section of one of the partially-pyramidal microelements of FIG. 49.

FIG. 55 is a plan view of an array of microelements that are mostly rectangular in shape but with sloped side walls and end walls, and which include through-slots in the microelements, as constructed according to the principles of the present invention.

FIG. 56 is a perspective view of one of the mostly-rectangular microelements of FIG. 55.

FIG. 57 is an enlarged plan view of one of the mostly-rectangular microelements of FIG. 55.

FIG. 58 is a side elevational view in cross-section of one of the mostly-rectangular microelements of FIG. 55.

FIG. 67 is a perspective view of an "inverted" microelement structure, similar in appearance to the microelements seen in FIG. 2, as constructed according to the principles of the present invention.

FIG. 68 is a perspective view of an "inverted" microelement structure, similar in appearance to the microelements seen in FIG. 67, but with several through-holes in the substrate, as constructed according to the principles of the present invention.

FIG. 69 is a perspective view of an "inverted" microelement structure, similar in appearance to the microelements seen in FIG. 66, as constructed according to the principles of the present invention.

FIG. 70 is a perspective view of an "inverted" microelement structure, similar in appearance to the microelements seen in FIG. 64 with through-slots, as constructed according to the principles of the present invention.

DETAILED DESCRIPTION OF THE PREFERRED EMBODIMENT

Figure 1:
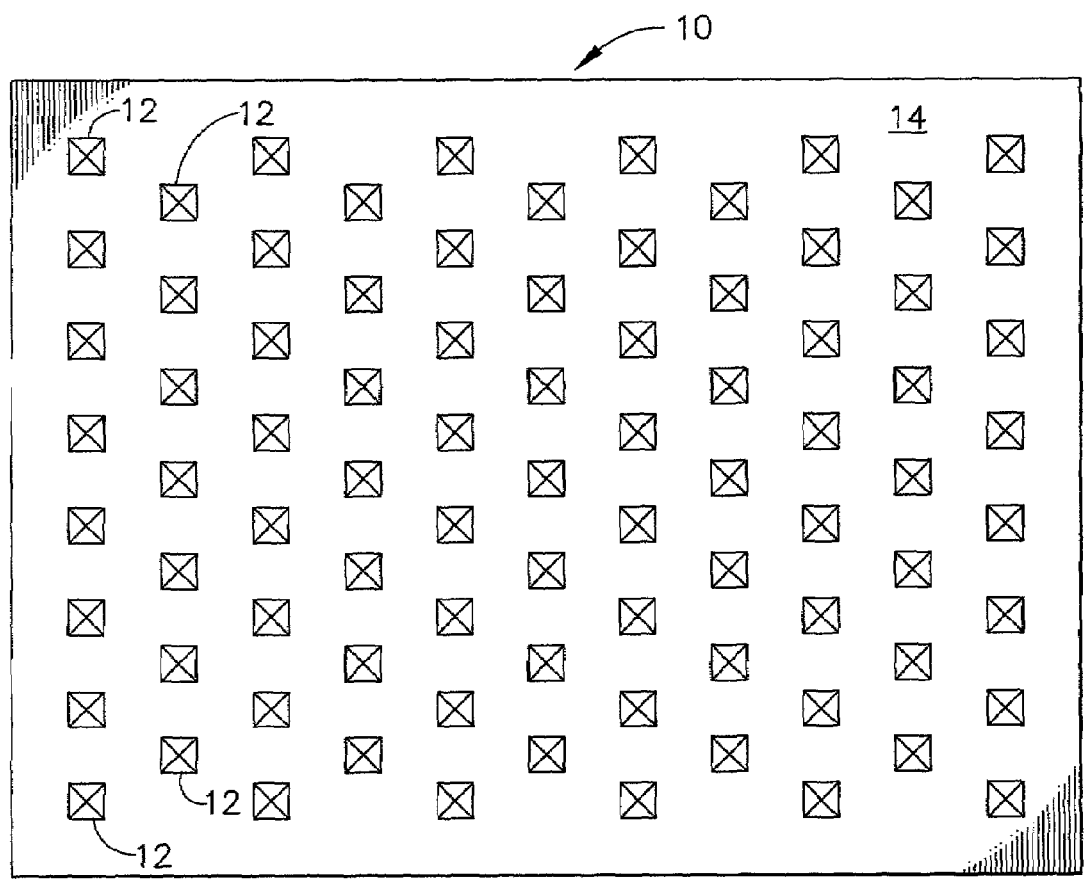
FIG. 1 is a plan view of an array of microelements that are pyramidal in shape, as constructed according to the principles of the present invention.

Reference will now be made in detail to the present preferred embodiment of the invention, an example of which is illustrated in the accompanying drawings, wherein like numerals indicate the same elements throughout the views.

The present invention relates to improving the health and condition, including the appearance, of human skin. The present invention comprises a system which utilizes an article of manufacture capable of selectively treating human skin and which can be modified depending upon the area of human skin which is to be treated, such as the face, hands, or feet; the type of treatment which is to be provided, such as skin refreshment; the type of adjunct compositions to be administered thereto, such as astringents, make-up, make-up remover, or at least one active or drug; or the respective frequency of use, as for example, daily in home use, or a single treatment by a skin care or medical professional in a clinic.

For the purposes of the present invention the term "skin enhancement treatment" is defined as "treatment of human skin with an article of manufacture as defined herein, wherein the surface of the skin is modified by controllably removing a selected number of skin layers or removing skin to a pre-determined depth, and optionally, delivering to the skin which has been treated, a skin enhancing composition, and/or removal therefrom of any unwanted substances." Embodiments of the present invention are directed to a wide range of skin enhancements, each enhancement based upon the type, configuration, and material, which comprises the microelements described herein. In addition, to the effects produced by the selected microelement, the systems of the present invention optionally comprise a composition that provides skin conditioning benefits.

The stratum corneum of skin comprises layers of dead skin cells, which are part of the body's protective outer layer. This outermost layer of skin cells can have a nominal thickness of from about one hundred (100) microns to about 250 microns for thick, durable skin areas, such as calluses, whereas normal, "thin" skin may comprise from about ten to about fifteen microns (10–15) thickness for its stratum corneum. One aspect of the present invention relates to the removal of the outermost layers (e.g., from 1 to 4 layers) of the stratum corneum. The articles of manufacture described herein are capable of selectively removing a predetermined number of skin layers (also known as "exfoliation"). This is achieved by adjusting the configuration of the microelements and/or the distance from which the distal end of the microelements protrudes from a particular base element.

By adjusting the configuration of the microelements, not only is the depth of skin scraping action modulated, but also the type of scraping action (or "rubbing") can be adjusted. For example, the articles of manufacture of the present invention may have hollow or grooved microelements that can serve as passages through which a substance may flow. These passages allow for transport of a material to the skin, for example, an emollient, or, as in the case of removed cellular tissue, dirt, etc., a material from the skin or skin constituents.

As used herein, the term "rubbing" represents an action by which one of the microstructures of the present invention is placed upon skin and moved (or "scraped") along the surface of the skin. The rubbing action (or "scraping" action) can be achieved manually, or by using a device. In other words, the microstructure can be held by hand and manually rubbed against the skin, or the microstructure can be placed on a mechanical device that will, in turn, be used to move (or rub) the microstructure upon the surface of the skin.

Articles of Manufacture

The articles of manufacture of the present invention comprise a base element (or "substrate") onto which is affixed or deposed a plurality of microelements. In general, the "proximal side" or "proximal surface" of the substrate is the surface that contains the microelements extending therefrom; the "distal side" or "distal surface" of the substrate is the opposite surface (keeping in mind that the substrate is generally planar and relatively thin in overall shape) of the substrate. The distal side or surface would typically be the side that is adjacent to any type of storage chamber or reservoir that would contain a fluidic material that may be applied through openings in the substrate or openings in the microelements (as described below). The following is a description of the base element and corresponding microelements.

Base Element

The articles of manufacture of the present invention comprise at least one base element having a first side and a second side. Onto the first side are affixed the microelements as described hereinbelow. Aside from providing a template or base structure onto which the microelements are affixed, the second side, or reverse side, may in turn comprise a handle or other means by which the article of manufacture can be held. In another embodiment, a substance can be deposed upon the second side, which allows the user to grasp, hold, or otherwise control the motion of the article using only the fingertips. The use of a material to provide a tactile surface is especially compatible for embodiments wherein the base element comprises a thin, substantially flexible material, such as paper or polymeric sheets. One embodiment of the present invention includes base elements which comprise flexible sheets, and the thickness of the sheets is determined by the desired degree of flexibility. The flexible sheets are typically rigid enough to provide a template upon which the microelements can be affixed, but which are easily deformed to fit the contours of the skin surface.

The base elements of the present invention may have any shape or configuration. For example, one embodiment relates to circular base elements, while another embodiment relates to rectangular base elements having a width and a length. For such articles of manufacture that comprise microelements having a "microelement angle" less than 90° as defined hereinbelow, rectangular base elements will have a left edge and a right edge. The right edge of the base element is defined herein as the edge along the right side of the base element when the second side of the base element is facing down (away from the observer) and the first side is facing the observer. The left edge is oppositely defined herein.

In another embodiment of the present invention, the second side may have at least one reservoir (or chamber) attached thereto (or constructed therewith) which contains a flowable (or "fluidic") composition, or at least one reservoir or chamber for receiving material (e.g., hair, oils, skin cells) removed from skin. For embodiments of this type, it is an option to modify the base element to comprise a plurality of hollow elements, or to provide channels or pore openings along with solid microelements. Such hollow elements or channels would ostensibly provide a means for a deliverable material or removable material to flow from the first side of the base element to the second side, or vice versa. The hollow elements can also be in register with a hollow element, channel, hole, or other passageway which modifies the microelements as described hereinbelow in a manner that allows a flowable composition to be delivered from the reservoir through a hollow element in the base element, through a tube or channel of the microelement, and onto skin.

For purposes of the present invention, the terms "fluid" or "fluidic" have a meaning that includes flowable liquids, flowable gases, relatively low-viscosity creams, flowable solutions that may contain solid particles, and the like. A "fluidic compound" or "fluidic material" specifically includes such liquids, gases, and solutions; these compounds or materials may comprise at least one active, a drug, or a skin conditioner, or other useful composition of matter; alternatively, the term "fluidic compound" can represent at least two actives, drugs, or the like, including both a biological active and a chemical active (in a single fluidic compound).

Microelements

The articles of manufacture of the present invention further comprise a plurality of microelements, which are affixed to the first side or first surface of the base element. The "proximal end" of the microelement is defined herein as "the microelement end that is affixed to or in register with the base element." The "distal end" of the microelement is defined herein as "the microelement end which comes into contact with skin, and which is the opposite end of the microelement from the proximal end." The term "microelement" is defined herein as "an appendage for contacting skin which extends from the first side of the base element and is affixed thereto (or protrudes therefrom) at an attachment angle." The term "microelement" refers to the entire element which contacts the skin and includes not only the appendage itself, but the attachment angle, any hollow elements or grooves, the density of the microelements as measured in the number of appendages per square centimeter, and any predisposed skin enhancement composition.

The term "skin" is defined herein as "animal skin, including human skin, plant skin or surfaces, and even other biological structures that may not have a true "skin" organ, such as tissue samples of either plant or animal origin."

For the purposes of the present invention, the term "affixed" as it relates to attachment of the microelements to the base element is defined as "held permanently to the first side of the base element." Affixed microelements are neither removable nor detachable. The microelements of the present invention, as it relates to the term "affixed" can comprise any suitable embodiment. For example, the microelements and base element may comprise a single uniform composition or the microelements may be extruded from the material comprising the first side.

Alternatively, and in a separate embodiment, the microelements may be applied to the base element in a separate operation or manufacturing step, such as lamination to a non-woven substrate. Therefore, the microelements can be fashioned and applied in any manner the formulator desires which achieves the desired microelement density or configuration. Other suitable microelement configurations include those described in U.S. patent applications: U.S. Ser. No. 09/580,780, U.S. Ser. No. 09/580,819, and U.S. Ser. No. 09/579,798 all filed May 26, 2000; U.S. Ser. No. 09/614,321 filed Jul. 12, 2000 all of which are commonly-assigned to The Procter & Gamble Company, and which are incorporated herein by reference.

In a further alternative embodiment, the microelements may be manufactured in a continuous embossing operation, in which the thickness of the initial substrate material is less than the height of the of the microelement as it extends above the proximal surface of the substrate. In such an embossing step, the height of the individual microelements may be such that the material (e.g., plastic) is deformed beyond its ultimate stress characteristic, and thus will fracture at the points of highest stress—and thus an opening may be created within the microstructure itself that extends through the substrate (i.e., from the substrate's proximal side (or surface) to its distal side/surface). Alternatively, the material may not be stressed beyond its ultimate stress characteristic, and thus will not fracture but at the same time the height of the microstructure may be greater than the thickness of the initial substrate material.

In yet a further alternative embodiment, the microelements may be manufactured in a molding operation, such that the height of the individual microelements is less than the thickness of the substrate material after being molded. In this further alternative embodiment, the substrate may have through-holes between its proximal and distal surfaces, or it may not, depending upon the application for use of the array.

In yet another alternative embodiment, the microelements may have a rectangular appearance when seen from above (i.e., when viewed from directly normal to its proximal surface), and in which the rectangular microelements may have a slot-like opening that extends through the substrate (i.e., through to the substrate's distal surface). These rectangular microelements can be oriented in a manner so as to be used in a preferred direction, or the microelements can be oriented in varying patterns so that virtually any direction of use would be effective.

Many of the microelements described herein are purposefully manufactured so as to not exhibit very sharp points, thereby creating less irritation to the skin surface when used in an exfoliation procedure, for example. While some of the microelement shapes described below are very pointed, such as at the tip of a four-sided pyramid, other microelement shapes purposefully do not exhibit such very sharp points and instead exhibit shapes that are somewhat blunted at their distal ends by their very design. However, the microelements that do not have pointed tips nevertheless maintain at least one sharp "edge," as in a cutting blade, so they can remove skin cells and other matter when used for exfoliation. In some instances, the microelements include through-holes or through-slots therein, so as to have the ability to pass a fluidic compound from a reservoir or chamber on the distal side of the substrate to the proximal side (and ideally onto the surface of skin). In the embodiments of the present invention, the microelements are mainly used to remove dead skin cells and other materials on the surface of skin (i.e., exfoliation), rather than being used to penetrate through the stratum corneum, which is the subject of other patent applications by the Assignee of this invention.

For the purposes of the present invention the term "microelement density" is defined herein as "the number of microelements per square centimeter of base element surface."

The appendages that comprise the microelements may be of any configuration that is capable of providing the desired skin enhancement. One embodiment of the present invention relates to a plurality of appendages in the form of regular conical appendages. Regular conical appendages have a circular proximal end and a pointed or rounded distal end. Another embodiment relates to inverted conical microelements, in which the appendages are conical appendages affixed to the base element at the tapered end and the circular base comprises the distal end. Rod-shaped appendages are circular or elliptical rods having a uniform circumference along the entire length. Planar appendages are cubes or cubic rectangles (or open boxes) wherein the length and width are uniform (but not necessarily equal to one another) throughout the height of the appendage and the distal end comprises a plane, such as a square, rectangle, or trapezoid, in which the plane is parallel to the base element or at an angle thereto. Wedge-shaped appendages have a rectangular proximal base that tapers to a line segment, which preferably has the same length as the length of the rectangular base. Some wedge-shaped appendages have an inverted appearance. Pyramidal appendages may comprise bases which have three or four sides at the proximal end base, and which taper to a point or rounded top at the distal end. Alternatively, the wedge-shaped appendages may have a triangular section removed therefrom that acts to facilitate the removal of skin hair follicles. The appendages of the present invention may also be coiled having any number of turns from the proximal end to the distal end.

For the purposes of the present invention the term "microelement angle" is defined as the "angle at which the appendage of the microelement protrudes from the base element." For example, a microelement, which is affixed perpendicular to the base element, has a microelement angle of 90°. The microelements of the present invention can be affixed to the base element at any angle from about 30° to about 90° (perpendicular). However, if the direction of use of the article of manufacture is not symmetrical, the microelements can be affixed to the base element at any angle from about 30° to about 150°. In addition, microelements which are not perpendicular to the base element may be angled toward any edge of a rectangular or square base element, or be perpendicular to the tangent of any point along the circumference of a circular base element.

The microelements of the present invention may also comprise hollow elements or contain grooves. Hollow elements are typically disposed along the longitudinal axis of the appendage portion of the microelement and are in register with a corresponding hollow element or passageway at the base element. Grooves or indented elements occur along the surface of an appendage and serve, like hollow elements, to move material toward the skin or remove material therefrom. For example, embodiments which provide a skin conditioning composition to the skin may use a series of hollow elements to deliver the composition from at least one reservoir to the skin. Or, natural facial oils may be carried away from the skin surface by capillary action though hollow elements or by inductive flow along grooves on the surface of the appendages.

The microelements of the present invention may range from absolute rigid (inflexible) to flexible. For the purposes of the present invention, the term "flexible" is defined herein as "during use against skin, the distal end of an appendage is bent or deformed up to 90° from the microelement angle as defined herein above." A perpendicular appendage which is bent 90° is therefore parallel with the base element. An appendage having a microelement angle of 45° can be deformed or bent to an angle of 135°.

The microelements of the present invention may have a protrusion distance of up to 2000 microns from the surface of the base element. The term "protrusion distance" is defined herein as "the distance from distal end of the microelement along a line parallel to the base element." For perpendicular microelements the length of the appendage and the protrusion distance are equivalent. A microelement having a microelement angle, for example, of 30° will have a protrusion distance equal to one half the length of the appendage.

One embodiment of the present invention relates to microelements having a protrusion distance of about 1–100 microns for "non-frictional skin," such as facial skin. Another embodiment relates to protrusion distances of about 1–50 microns. Further embodiments encompass microelements wherein the appendages have protrusion distances from about one to about twenty (1–20) microns, whereas other embodiments include protrusion distances of from about five to about twenty (5–20) microns and from about four to about twenty (4–20) microns, as well as embodiments from about four to about ten microns (4–10). Other embodiments comprise no range of protrusion distances but have discreet distances such as, for example, a 4-micron embodiment, a 5-micron embodiment, or a 10-micron embodiment.

The microstructures of the present invention can also be used on "frictional skin," such as skin on the elbow or heel. For such applications, the protrusion distances of the microelements may be much longer, and will more likely be in the range of 100–2000 microns.

The microelements of the present invention may comprise an appendage, which has flexible elements and rigid elements, for example, an appendage which has a rigid portion extending from about the middle of the element to the proximal end and a flexible portion extending from about the middle of the element to the distal end. Articles of manufacture which are composites of several materials may comprise a thin flexible base element onto which are deposed rigid, inflexible microelements.

The articles of manufacture of the present invention may comprise a multitude of arrays, each array comprising the same or different types or sizes of microelements, in which the various attributes of the microelements, including microelement density, appendage type, microelement angle, hollow elements vs. solid elements with or without grooves, degree of flexibility, protrusion distance, etc. may vary from array to array or within a single particular array. For the purposes of the present invention the term "array" is defined as "multiple microelements in a pattern."

In some cases, certain array elements collectively may be separated from another array by a distance which is greater than the distance between the microelements which comprise the first array. In other cases, arrays may contain different types of microelements which all have the same spacings. The distance between microelements along the edge of two separate and distinct arrays may be greater than the distance between two microelements, which are members of the same array. Alternatively, several different microelement shapes or protrusion sizes may exist in a single array in which all individual elements are spaced-apart from one another in a consistent manner throughout the entire structure.

The microelements preferably have a length and shape that will tend to scrape skin cells (typically dead or loose skin cells) from the upper surface of the stratum corneum, while at the same time will not tend to penetrate entirely through the stratum corneum layer. The characteristic of the microelements to not cut or penetrate entirely through the stratum corneum is further enhanced by directing the user to move the "patch" or microstructure in only one direction (or in a single line that represents a back and forth direction), so that the "sharper" edges of the microelements do not tend to cut or plow into the skin upper layers; instead, these sharper edges merely assist in scraping away the skin cells. As will be seen in the drawings, some of the microelements have shapes that also assist in accumulating the skin cells (as well as other foreign substances found on the skin surface) once they have been scraped loose.

Referring now to the drawings, FIG. 1 illustrates a microstructure array generally designated by the reference numeral 10 containing multiple microelements 12 that are situated on a base or substrate 14. In FIG. 1, each "column" of microelements 10 is offset from the next, adjacent column of similar microelements. However, each of the columns could be made to be identical to one another, if desired, and the offset could be removed. Alternatively, there could be several columns with various offsets before the microelement pattern repeats, or the offsets could be substantially random so that there is no repetitive pattern.

Figure 2:
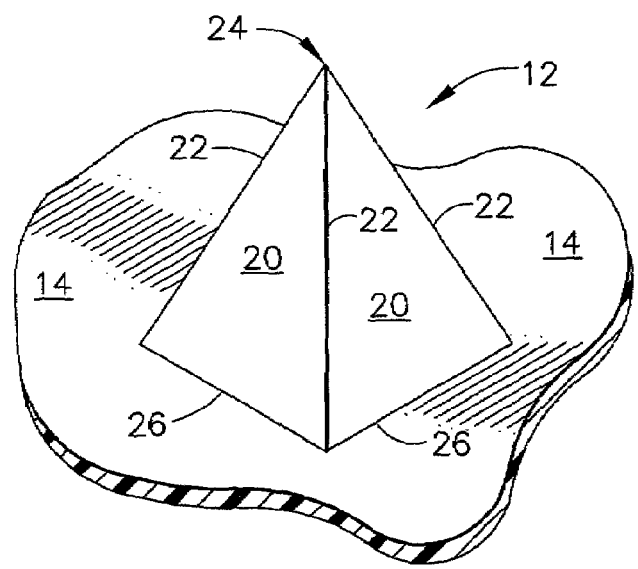
FIG. 2 is a perspective view of one of the pyramidal microelements of FIG. 1.

FIG. 2 illustrates in a magnified view one of the microelements 12, which has the appearance of a four-sided pyramid. Each side wall of the pyramid is designated at the reference numeral 20, and the seam or "corner" between sides is located at the reference numeral 22. The pyramid's peak is illustrated at 24, and the base line of each of the sides is located at 26, where it meets the substrate 14.

This array 10 of microelements is very useful in skin preparation by forming it into a patch that can be held by a human hand, and placed against a particular area of skin and then rubbed in a straight back and forth motion (or perhaps in a circular motion, if desired). When the patch or array 10 is rubbed against the skin, the microelements 12 will tend to remove skin cells that will accumulate in the planar spaces between the individual microelements 12. Since the skin cells that are removed do not become airborne, the microstructure array or patch 10 is a great improvement over the previously available mechanical scrubbers. Instead of knocking skin cells loose, the invention of FIG. 1 will trap the loose skin cells, which will then be disposed of along with the microstructure array 10.

In essence, the microstructure array 10 is very useful for an exfoliation of the skin, which in essence will pre-treat the skin for a later application of a conditioner substance, if desired. In addition to removing the skin cells, the array structure can also remove and collect foreign substances or even hair that are found on the surface of the skin while the microelements are rubbed along the skin surface. Once the area between the pyramidal microelements 12 becomes "full" of removed or "loose" skin cells and other substances, then this microelement array 10 essentially loses its functionality. The amount of material (including the loose skin cells) that is removed by use of the microelement array 10 is controlled by the height of the individual microelements 12 and the spacings therebetween. This allows fairly precise control over the number of layers of skin cells that are removed.

The array or patch 10 will correctly perform its functions of scraping and removing skin cells without regard to the direction of movement of the patch 10 with respect to the orientation of the individual microelements 12. In other words, these microelements 12 are omnidirectional in operation, and all directions are preferred, or even "predetermined." Other embodiments of the invention described below are not omnidirectional, and instead are unidirectional or bi-directional in nature with respect to the orientation of their individual microelements.

One very important aspect of the present invention utilizes the above rubbing/scraping feature, by which skin cells and other materials are first scraped loose, and then removed from the skin surface. The "precise control" noted above in connection with removal of the number of layers of skin cells is a "self-limiting" feature, in that the substrate-microelement combination (i.e., the microstructure patch 10 itself) will only remove a substantially predetermined quantity of these skin cells and materials before becoming "full," after which the patch 10 essentially will not remove any further skin cells/materials. The system is basically fool-proof! Even if the user, either out of ignorance or exuberance, attempts to continuously re-use the patch, it will not further "scrape" the user's skin. After the patch 10 has accumulated the maximum amount of material that it can nominally hold, any additional skin cells removed by such further attempts to scrape the skin will be minuscule in quantity, and such further scraping attempts are essentially futile.

Similar microstructures are described below, although most of them exhibit different shapes for their microelements that protrude from the substrate. It will be understood that, regardless of the shape or size of the individual microelements, each of the microstructure patches described herein will have the capability for providing this fool-proof result. This is a significant improvement over previously-available devices that have been used for conditioning skin.

Another feature of the microstructure 10 is its capability for use in applying a conditioner or other type of compound that is in the form of a liquid or a cream. Just after the microstructure patch 10 has "cleansed" (exfoliated) an area of skin, the skin's surface will be smoother and mostly free of foreign substances. It is the perfect time to apply a fluidic compound, such as a conditioner, to the skin. The conditioner could enhance the health of the skin, or be in the form of make-up, for example. It also could be some type of topical drug or other active, if desired. The other microstructures described below will also lend themselves well for this type of topical application of a fluidic compound to skin.

A further feature of the microstructure 10 is its capability for a compound to be applied onto the substrate 14 and/or microelements 12 in advance of its placement against an area of skin. When the microstructure patch 10 is placed onto the skin, it will impart some of this compound onto the same area of the skin that is being cleansed, or exfoliated—this will essentially occur simultaneously. The other microstructures described below will also lend themselves well for this type of simultaneous delivery of a fluidic compound to the same area of skin that is being exfoliated. Of course, the embodiments described below which include through-holes in the substrate (e.g., see FIGS. 3 and 4) may not be the first choice for this methodology of composition delivery, but such devices certainly could be used in this manner, if desired. The compound that is pre-applied to the surface of the microstructure 10 could be placed either by the user, or at the time of manufacture of the microstructure 10.

Figure 3:
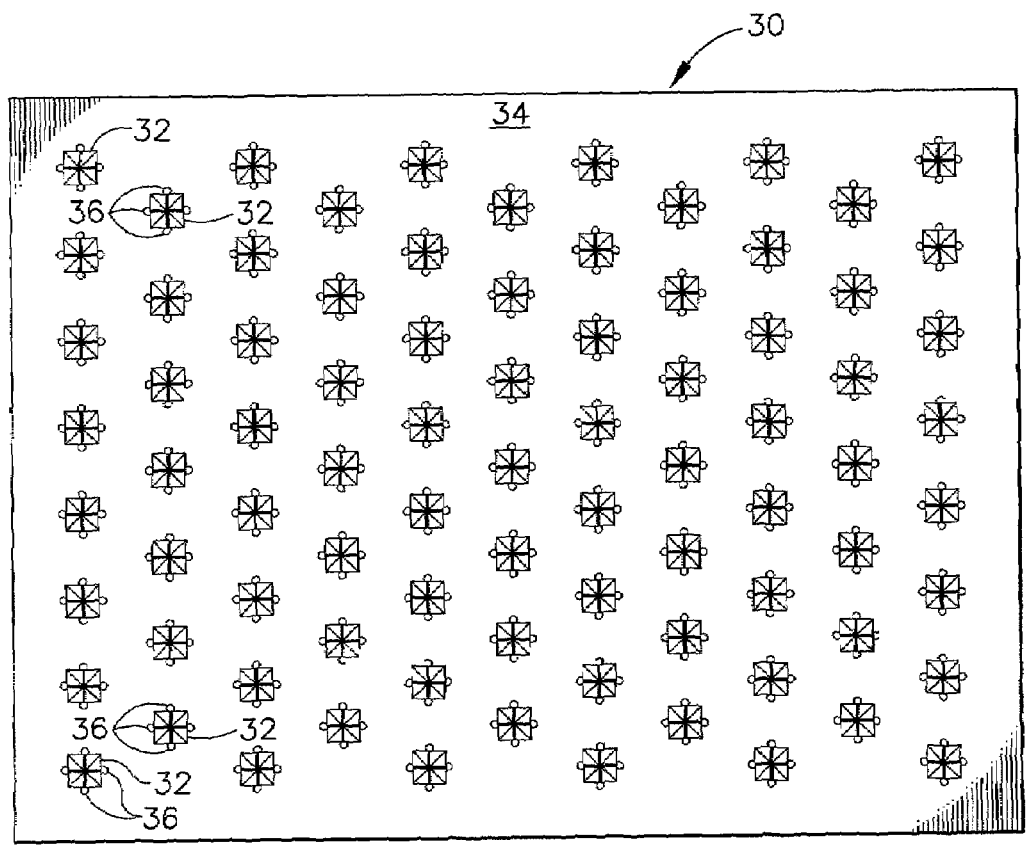
FIG. 3 is an array of pyramidal microelements as according to FIG. 1, with the addition of through-holes in the substrate, and channels along the sides of the microelements.

FIG. 3 illustrates a similar microelement array, generally designated by the reference numeral 30, in which through-holes and channels are added. The base or substrate 34 includes a plurality of through-holes 36 that are positioned proximal to the base of the individual pyramidal microelements 32. These through-holes 36 can either penetrate through the entire substrate 34, or can penetrate partially into the substrate and connect to passageways that may run in a direction perpendicular to the through-holes, and make common connections between many of the through-holes.

Figure 4:
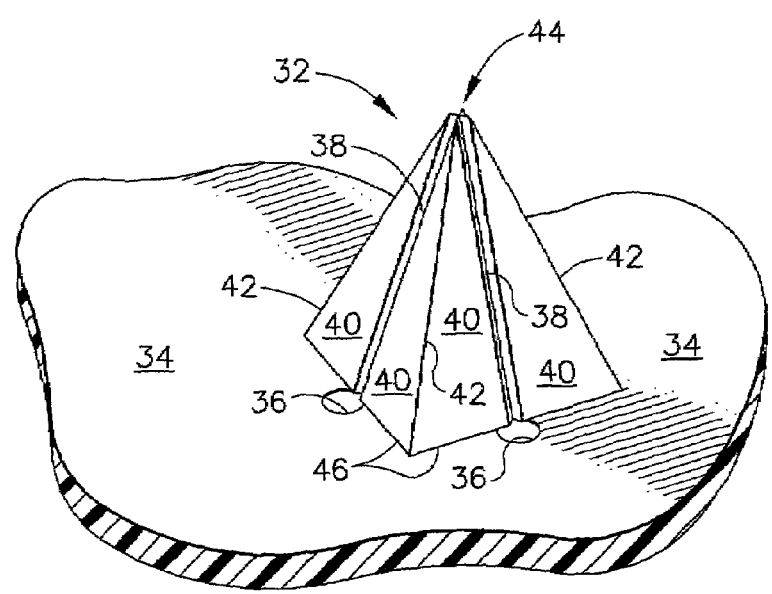
FIG. 4 is a perspective view of the pyramidal microelements of FIG. 3.

On FIG. 4, further details are visible, in which the side walls 40 of the pyramidal microelement 32 are seen to have grooved channels 38 which connect to the through-holes 36. The edges of the side walls 40 are at reference numeral 42, the individual base lines of the pyramid are at 46, and the peak of the pyramid is at 44.

On FIGS. 3 and 4, the array 30 of multiple pyramidal structures at 32 all have a through-hole adjacent to each side of the pyramid. Of course, there could be fewer through-holes 36 per pyramidal microelement 32, if desired. Alternatively, some of the pyramidal microelements 32 in the array could have no adjacent through-holes, if desired. Such microelements (or others in the array) could also forego the channels 38.

The structure of FIGS. 3 and 4 is useful to perform a simultaneous exfoliation and conditioning step. While the array or "patch" 30 is rubbed along the skin, the removed or loose skin cells will accumulate in the open spaces between the individual pyramidal microelements 32, which will prepare the skin for any type of conditioning that will then be placed upon that skin surface. Even after the "spacing areas" between the microelements 32 become essentially full of loose skin cells and oils or other substances found on the skin surface, at least one active or conditioner can nevertheless be delivered through the grooves or channels 38 by use of a capillary force. Moreover, the loose skin cells will not necessarily be tightly jammed along the surfaces of the pyramidal microelements 32, and therefore, should not become a significant obstacle to the delivery of the active or conditioner along the channels or grooves 38. Furthermore, the capillary force will work to the advantage of delivering a conditioner or active, especially in partially-blocked grooves or channels 38.

Similar to the patch 10, the array or patch 30 will correctly perform its functions of scraping and removing skin cells without regard to the direction of movement of the patch 30 with respect to the orientation of the individual microelements 32. In other words, these microelements 32 are omnidirectional in operation, and all directions are preferred, or even "predetermined."

Figure 5:
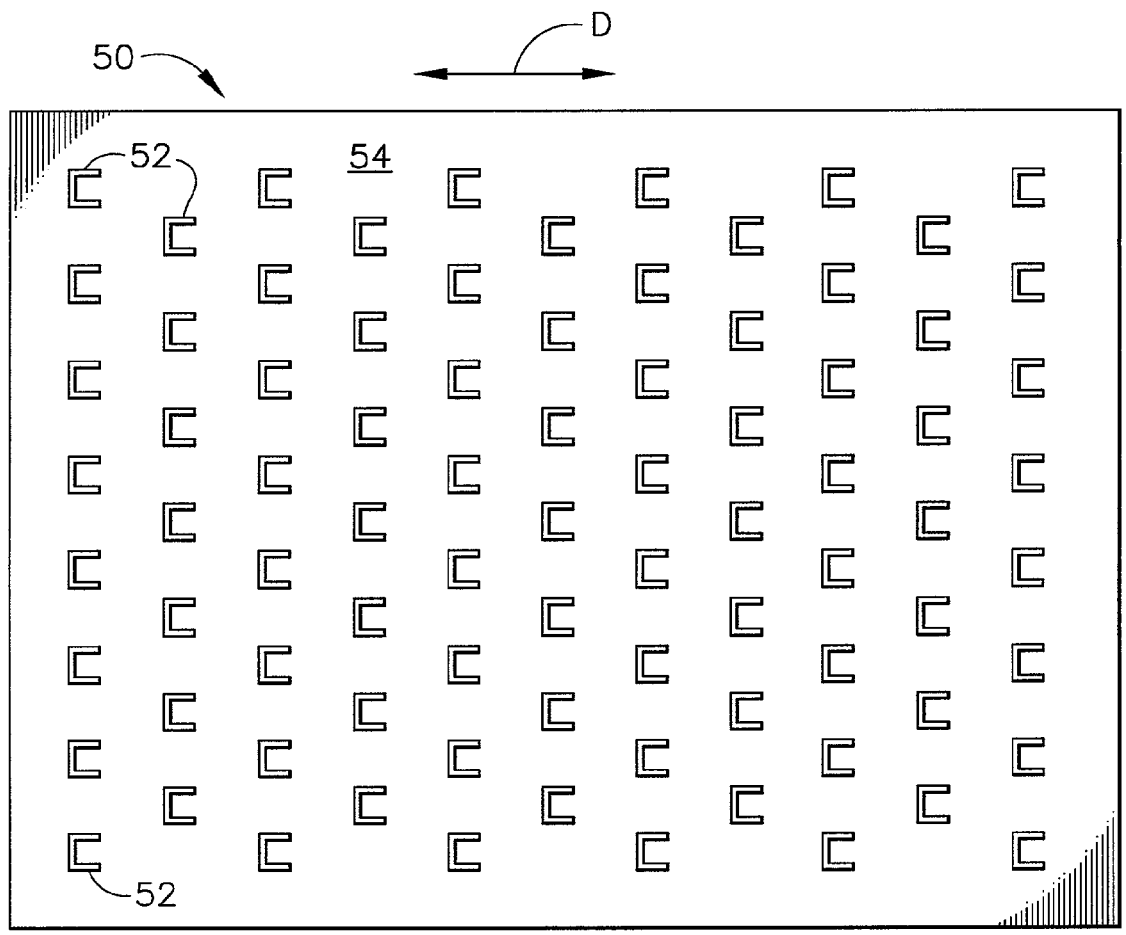
FIG. 5 is a plan view of an array of microelements that have an overall cubic rectangular shape, as constructed according to the principles of the present invention.

Another microelement shape is illustrated in FIG. 5, comprising an array 50 of "cubic rectangular" microelements at 52. These microelements 52 have a cup-like shape which has the appearance of a topless, hollow or open cube-like or box-like structure after one of the cube's (box's) side walls have been removed. This can be clearly seen in the perspective view of FIG. 6. (It will be understood that the "cube-like structure" 52 does not have identical length, width, and height outer dimensions, and thus is not really a geometric cube. In that respect, the term "box-like" or "box" is more descriptive.)

The individual columns of microelements 52 can be offset on the substrate 54, as seen in FIG. 5. As an alternative construction, each of the individual columns of these microelements 52 could be identical, thereby eliminating any offset, if desired. As a further alternative, there could be several columns with various offsets before the microelement pattern repeats, or the offsets could be substantially random so that there is no repetitive pattern.

To perform an exfoliation of skin, the microstructure or "patch" 50 is rubbed back and forth substantially along the direction designated by the letter "D" (which is a preferred, predetermined direction). In this manner, the open cup-like area will easily collect the loose skin cells and other foreign substances on the surface of the skin. The "open" area that will collect these cells is easily seen at 68 in FIG. 6.

Figure 6:
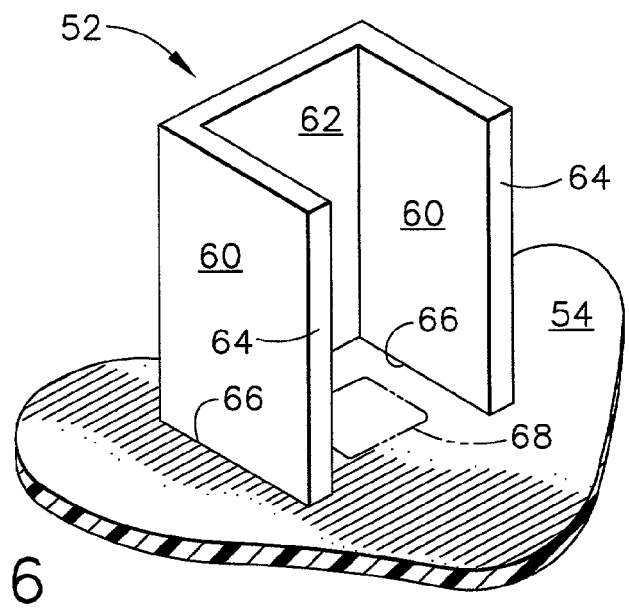
FIG. 6 is a perspective view of one of the cubic rectangular microelements of FIG. 5.

FIG. 6 shows further details of the individual microelement 52, which has a "back wall" 62, a pair of "side walls" 60, a "front edge" at 64 on each of the side walls 60, and a base line 66 along the bottom of the side walls 60.

As in the previously described embodiments, the amount of skin cells that can be collected by this structure 50 will depend upon the height of the individual microelements 52, as well as the spacings between such microelements on the substrate 54. The cup-like shape of the individual microelements 52 provides even better control over the quantity of material that is to be removed due to the rubbing action. Factors that impact the skin cell sizes to be removed (and the overall quantity of material to be removed) include the height of the walls 60 and 62, the open distance between edges 64 (i.e., the area 68), and the sharpness of the edges 64 themselves.

Figure 7:
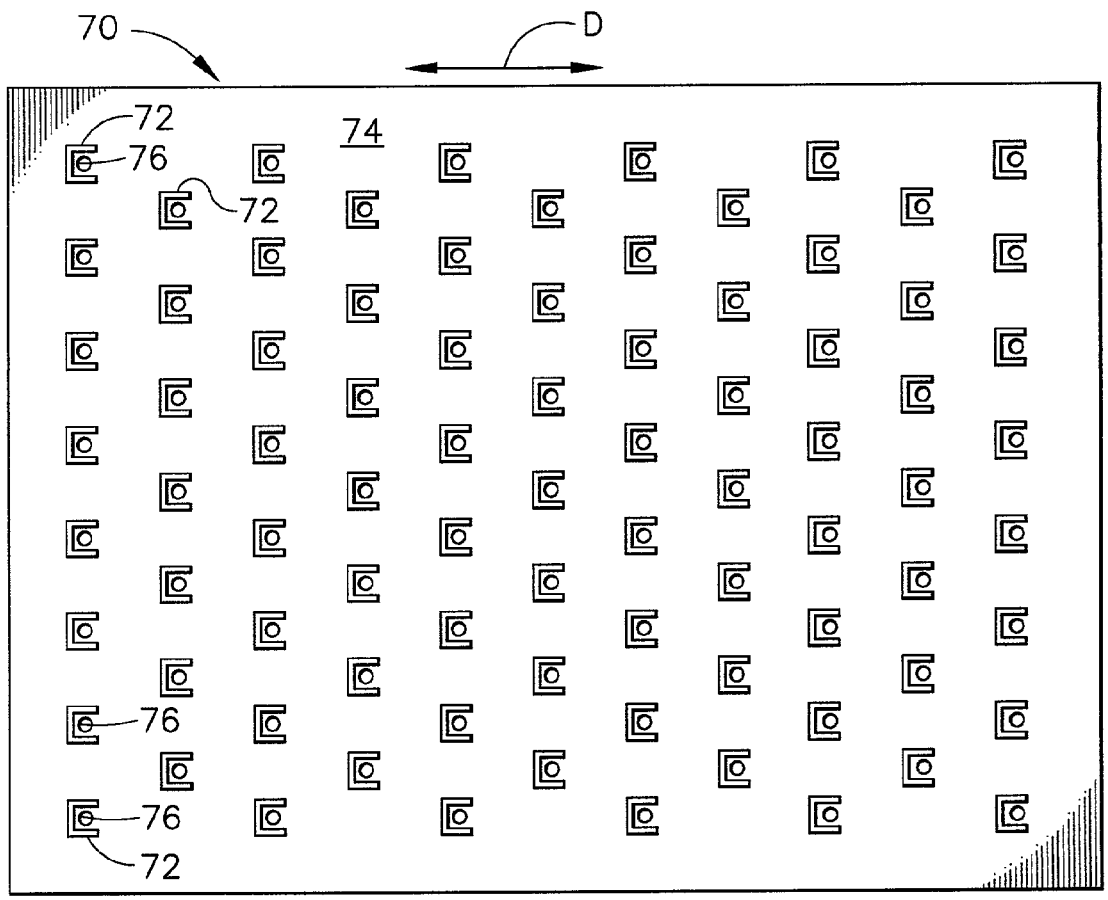
FIG. 7 is a plan view of an array of the cubic rectangular microelements of FIG. 5 with the addition of through-holes in the substrate.

FIG. 7 illustrates a similar array of microelements, designated by the reference numeral 70. Each individual microelement 72 has a similar appearance to the open box-like microelements 52 of FIGS. 5 and 6, however, a through-hole 76 has been added within the "cup-like" area of the microelement 72. These holes typically would run completely through the base or substrate 74, although they could instead extend only partially into the substrate to connect to some type of internal channels. In that manner, these holes could become (or connect to) passageways of any shape, diameter, or length.

Figure 8:
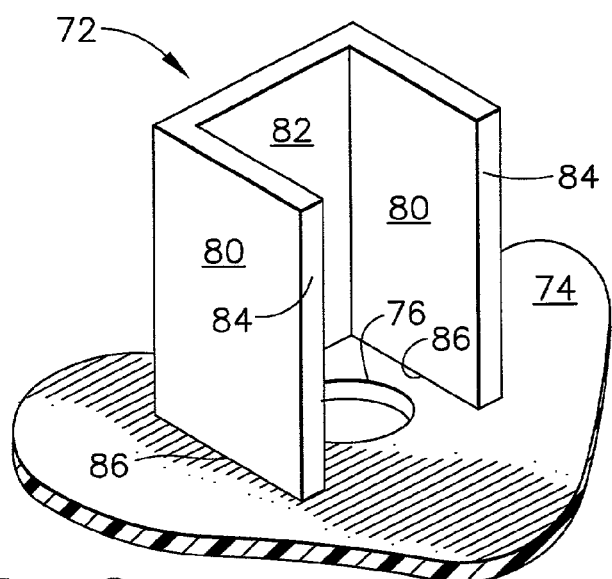
FIG. 8 is a perspective view of one of the cubic rectangular microelements of FIG. 7.

The microstructure array 70 could be formed into a "patch" that is applied to skin and rubbed in a back and forth manner substantially in the direction "D" indicated on FIG. 7 (which is a preferred, predetermined direction). FIG. 8 shows further details, in which there are two side walls 80, a back wall 82, two "front" edges 84, a base line 86 for each of the side walls 80, and the through-hole 76 that is proximal to the interior area of the microelement 72. In a similar manner to the previously described microstructure of FIGS. 3 and 4, the microstructure 70 disclosed on FIGS. 7 and 8 can be used to simultaneously exfoliate the skin surface while delivering some type of active that will condition the skin, or otherwise treat the skin. Such systems can both exfoliate and deliver in a single operation.

Figure 9:
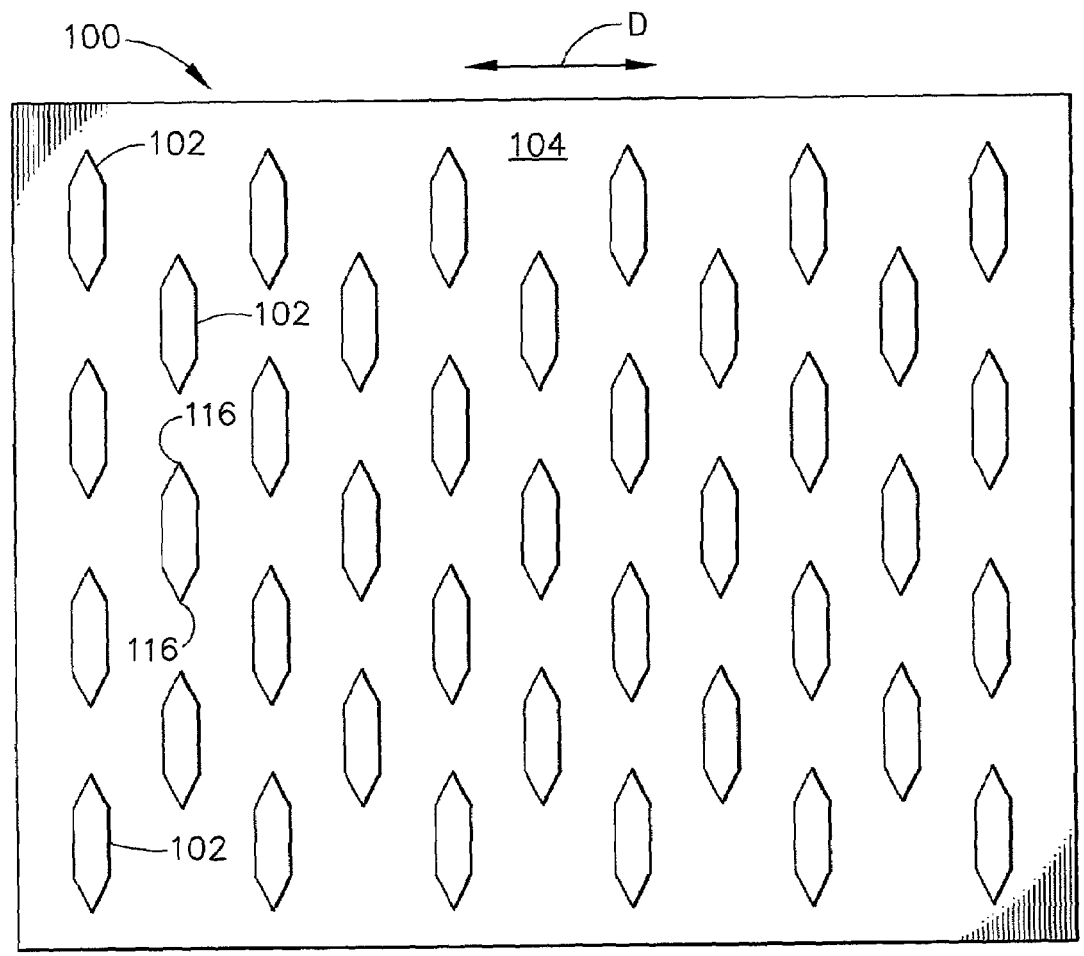
FIG. 9 is a plan view of an array of wedge-shaped microelements, as constructed according to the principles of the present invention.

FIG. 9 illustrates an array 100 of wedge-shaped microelements 102 mounted onto a base or substrate 104. As in some of the earlier-described embodiments, each column of microelements 102 can be offset from the adjacent column, as illustrated on FIG. 9. However, the columns could alternatively be made identical to one another, in which there would be no offset. A further alternative could arrange several columns with various offsets before the microelement pattern repeats, or the offsets could be substantially random so that there is no repetitive pattern.

Figure 10:
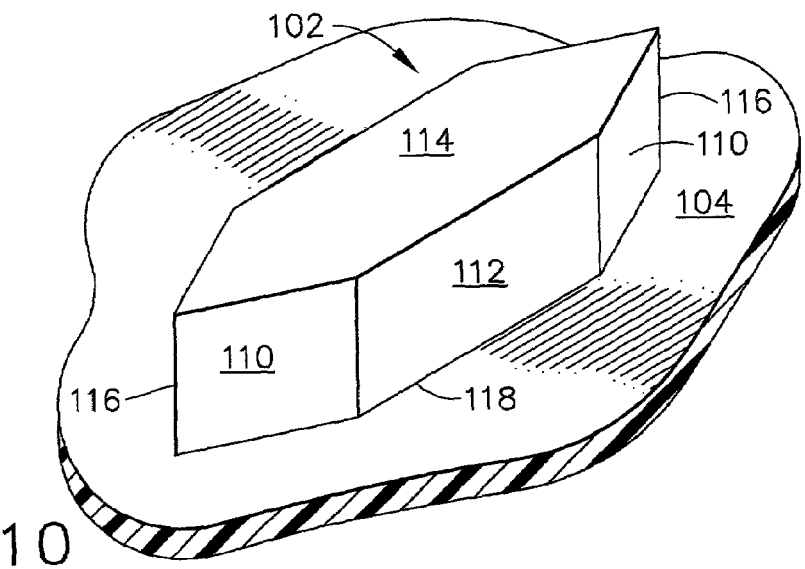
FIG. 10 is a perspective view of one of the wedge-shaped microelements of FIG. 9.

The wedge-shaped microelement 102 is illustrated in greater detail in the perspective view of FIG. 10. The top of the structure is at 114, and there are two elongated side walls 112 and a pair of converging side walls 110 that, at their line of convergence, form a cutting edge 116. There is also a base line 118 at the junction between the side wall 110 and the substrate 104.

The relatively sharp edge 116 is not purposefully used to "cut" skin in the exfoliation methodology described in this patent document. Instead, the overall wedge shape of the microelement 102 is provided as a more substantial structure than some of the other embodiments described herein. It also is probably easier to manufacture than the microelements described earlier, in FIGS. 1–8. In the microelements of the array 100 on FIG. 9, it is preferred to apply the array as a "patch" onto skin, and then rub it in a back and forth manner substantially along the line "D" (which is a preferred, predetermined direction). As can be seen from FIG. 9, the relatively sharp edges 116 will not be used to cut into the skin when the patch 100 is moved in this manner along the line "D." Rather than cutting the skin, the microelement patch or array 100 is designed to exfoliate the skin and accumulate skin cells and other foreign substances that have accumulated on the skin. The amount of removed skin cells and foreign substances that will be accumulated on the microelement array 100 depends upon the height of the individual microelements 102 and the spacings therebetween.

Figure 11:
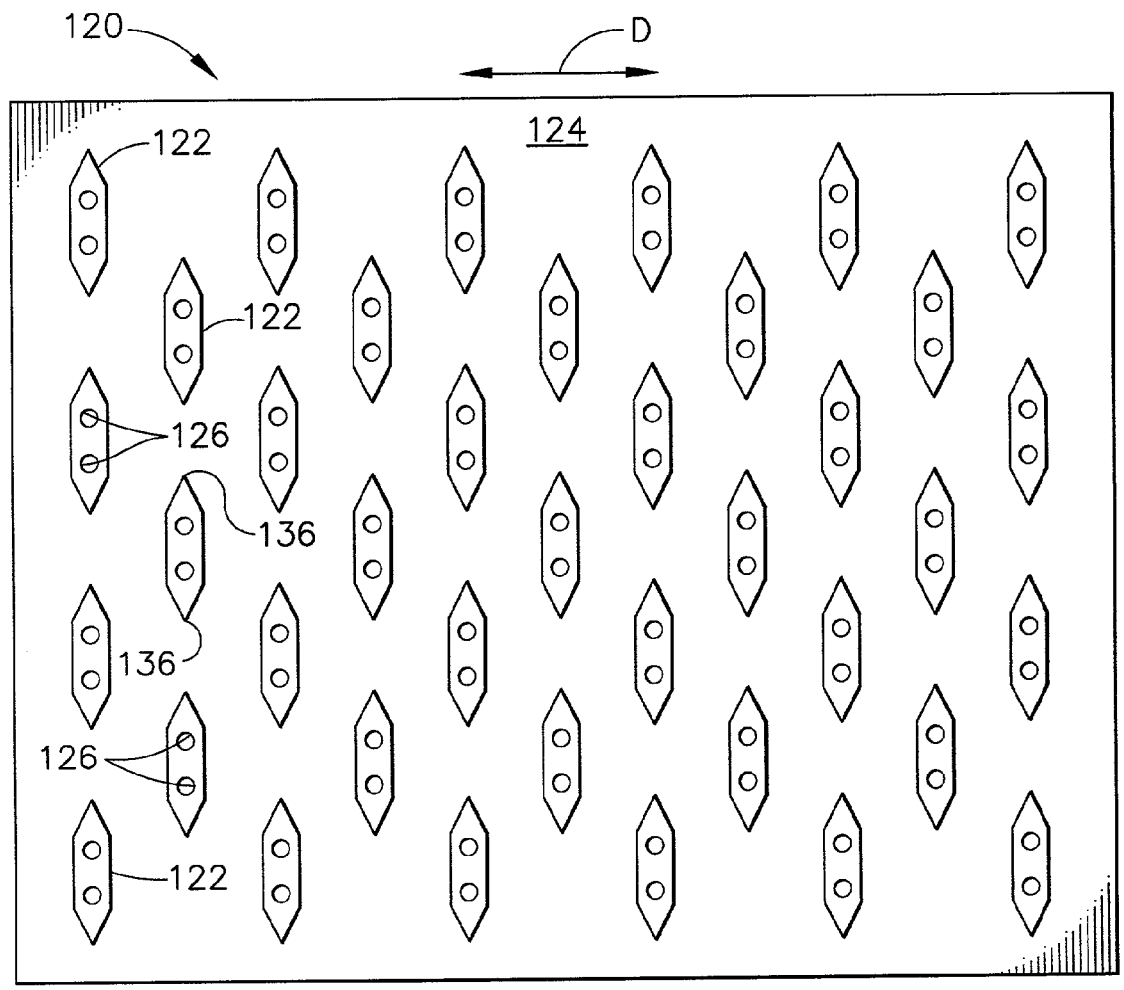
FIG. 11 is a plan view of an array of the wedge-shaped microelements of FIG. 9 with the addition of through-holes that penetrate through the microelement and through or into the substrate.

FIG. 11 shows a similar wedge-shaped microstructure array at 120, which has individual wedge-shaped microelements 122 that have two separate through-holes at 126. The microelements 122 are all mounted on a base or substrate 124. As viewed in FIG. 11, the columns of microelements 122 are somewhat different from one another, in that they are offset from one another in adjacent rows. This need not be the case, and alternatively the columns could be identical to one another to eliminate any offset, if desired. Again, alternatively there could be several columns with various offsets before the microelement pattern repeats, or the offsets could be substantially random so that there is no repetitive pattern.

Figure 12:
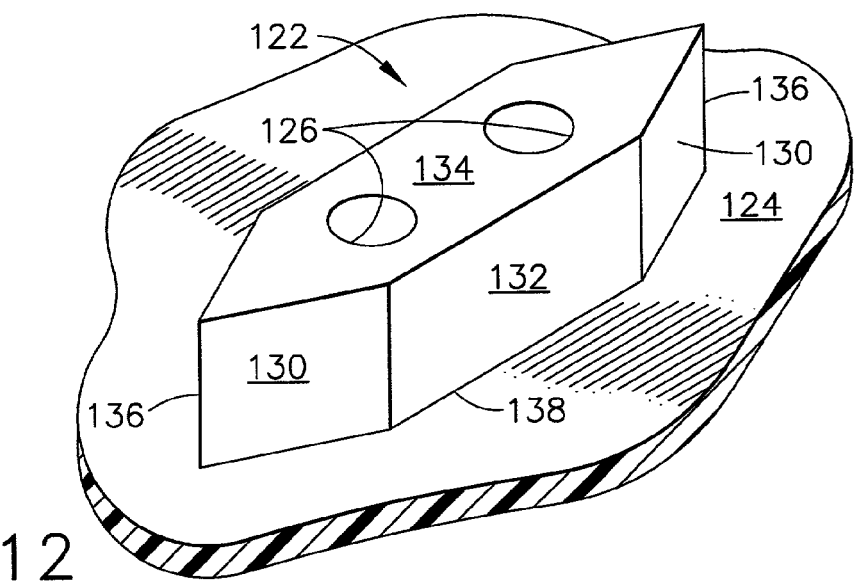
FIG. 12 is a perspective view of one of the wedge-shaped microelements having through-holes of FIG. 11.

FIG. 12 shows further details of the individual microelement 122, in which a top surface 134 and elongated side walls 132 are exhibited, along with converging side walls 130 that come to a sharp edge 136. A base line 138 is also illustrated as the junction between the microelement 122 and the substrate 124. The through-holes 126 are created to penetrate entirely through the microelement 122, and preferably will also penetrate entirely through the base 124, although the holes 126 can become passageways that do not entirely penetrate through the base or substrate, but instead connect to some type of perpendicular runs or passageways, if desired. Since there are two separate holes 126 per microelement 122, it is possible to simultaneously deliver two different actives (one per hole in a single microelement) in a single operation, if desired.

The microelements 122 are designed to perform both an exfoliation and delivery procedure in a single step. In this particular structure, it can almost be guaranteed that there will be a lack of build-up of dead skin and other foreign matter within the delivery holes or passageways 126. Even if some of this foreign matter or dead skin cells accumulates in these passageways 126, a capillary action may result and accomplish delivery of at least one active or drug through the passageways 126 onto the surface of the skin.

Figure 13:
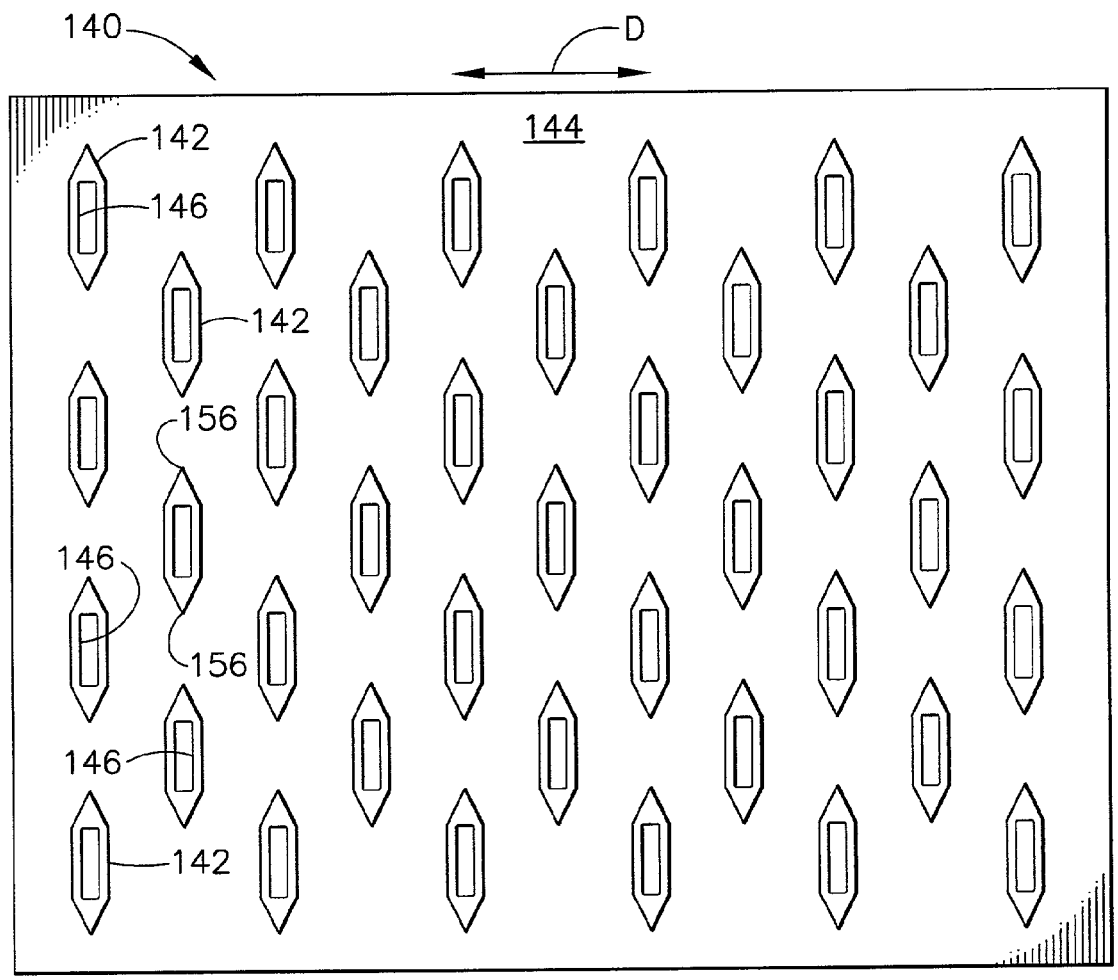
FIG. 13 is a plan view of an array of wedge-shaped microelements of FIG. 9, in which a through-slot is located in the microelements, which penetrates through or into the substrate.

FIG. 13 illustrates a microstructure array designated by the reference numeral 140 that contains a large number of individual wedge-shaped microelements 142 that are mounted to a base or substrate 144. These wedge-shaped microelements 142 contain a through-slot 146, through which at least one active or drug can be delivered to a skin surface after an exfoliation operation has taken place. In a similar manner to the structures of FIG. 11, the microelement array or patch 140 will preferably be placed on the skin surface and rubbed in a back and forth manner substantially along the direction "D" (which is a preferred, predetermined direction) to remove skin cells and other foreign substances from the skin surface. The amount of material removed from the skin surface will depend upon the height of the individual microelements 142 and the spacings therebetween.

Figure 14:
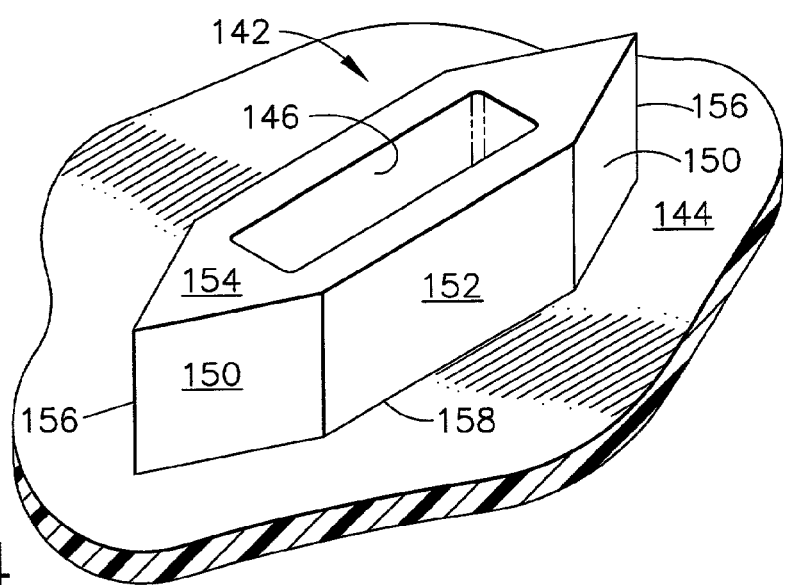
FIG. 14 is a perspective view of one of the wedge-shaped microelements having the through-slot of FIG. 13.

FIG. 14 shows greater details of an individual microelement 142, showing a top surface 154, side walls 152, converging side walls 150 that come to a relatively sharp edge 156, and a base line 158 where the microelement 142 adjoins the base or substrate 144.

The through-slot 146 can provide a larger cross-sectional area for delivery of at least one active or drug to the skin surface, as compared to the microelement 122 of FIG. 12. Of course, the actual dimensions of the microelement 142 could be either larger or smaller than similar microelements 122 illustrated on FIG. 12. Both sets of microelements 122 and 142 are relatively simple to construct, although the ones with the through-slot 146 may be somewhat easier to construct as compared to constructing multiple smaller through-holes 126.

The patch or array 140 can be used for a combinational step of exfoliation and delivery of at least one active, in a similar fashion to that described in some of the earlier embodiments. Other similar shapes of wedge-shaped structures could easily be constructed without departing from the principles of the present invention.

Figure 15:
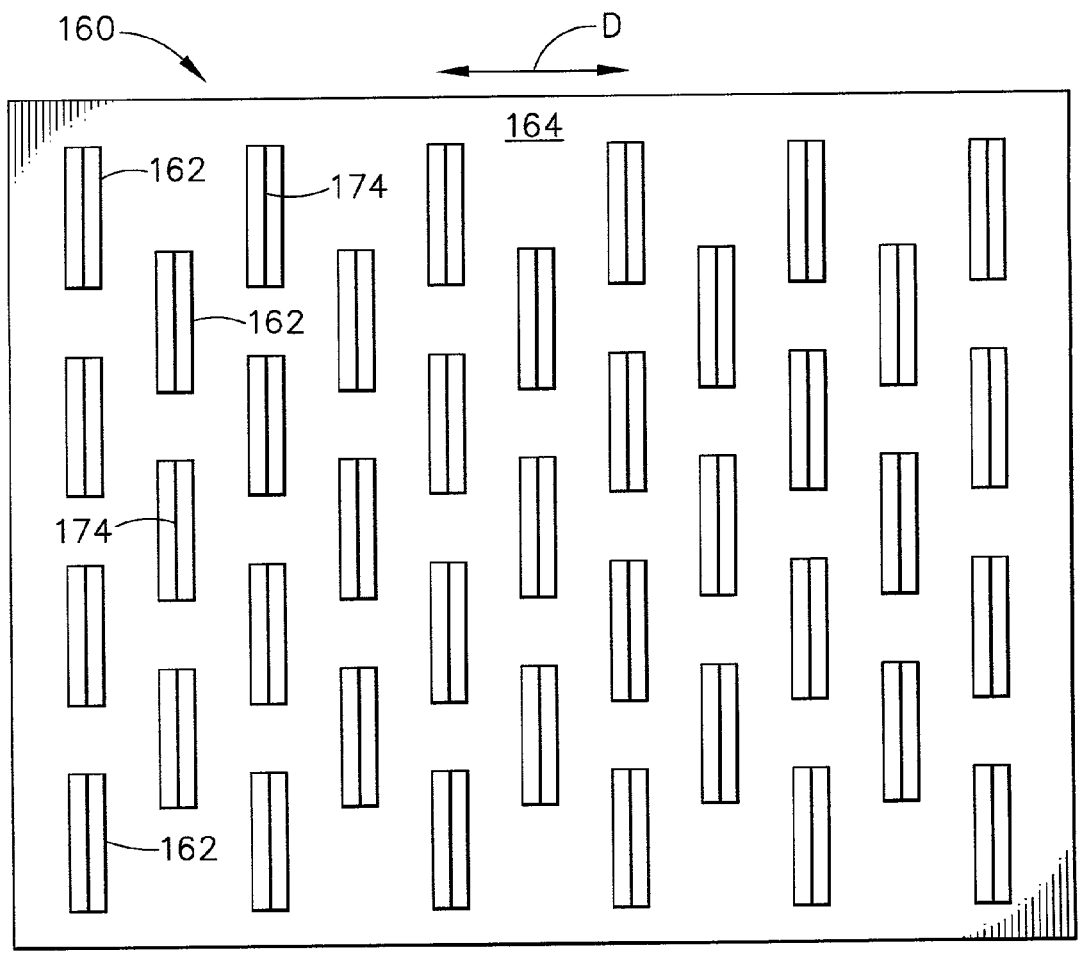
FIG. 15 is a plan view of an array of microelements having an elongated triangular shape, as constructed according to the principles of the present invention.
Figure 16:
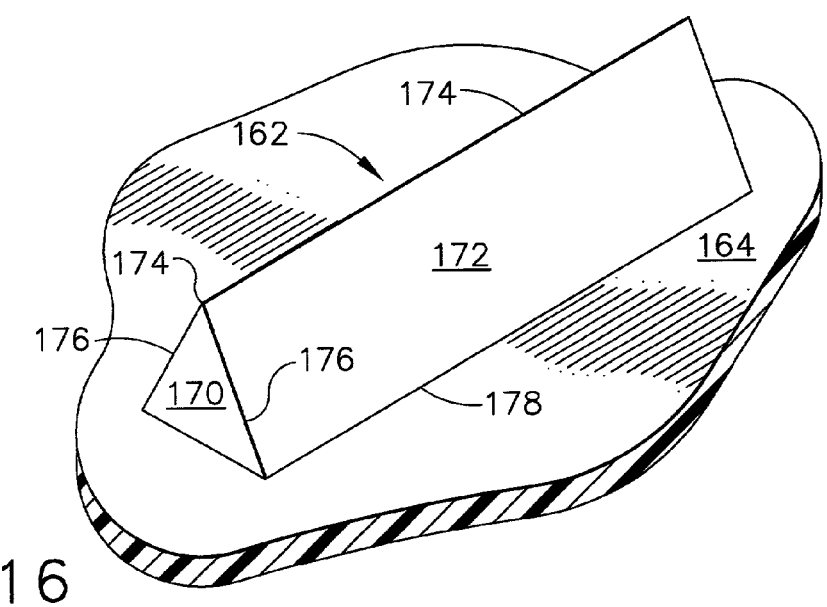
FIG. 16 is a perspective view of one of the elongated triangular microelements of FIG. 15.

FIG. 15 discloses an array or patch 160 of triangular-shaped wedge microelements 162, mounted on a base or substrate 164. As seen in FIG. 16, each of the microelements 162 consists of an elongated triangular shape, having a pair of triangular side walls 170, a pair of sloped elongated side walls 172, a top edge 174, and a pair of base lines 178. The junction between the triangular end walls 170 and the rectangular but sloped side walls 172 is designated at the reference numeral 176. The peak of the triangle is illustrated at 174, which is only one point along the top edge 174 of the microelement 162.

These triangular-shaped wedges can be useful in an exfoliation procedure, and preferably will be placed on skin in the form of a patch and then rubbed back and forth over the skin substantially in the direction "D" (which is a preferred, predetermined direction). The amount of loose skin cells that are removed (and the amount of any additional foreign substances removed) will depend upon the overall height of each of the microelements 162 and the spacings therebetween. The individual columns of microelements can be offset from one another in adjacent columns, as seen in FIG. 15. Alternatively, the columns could be identical to one another, without any offset. Another alternative could arrange several columns with various offsets before the microelement pattern repeats, or the offsets could be substantially random so that there is no repetitive pattern.

Figure 17:
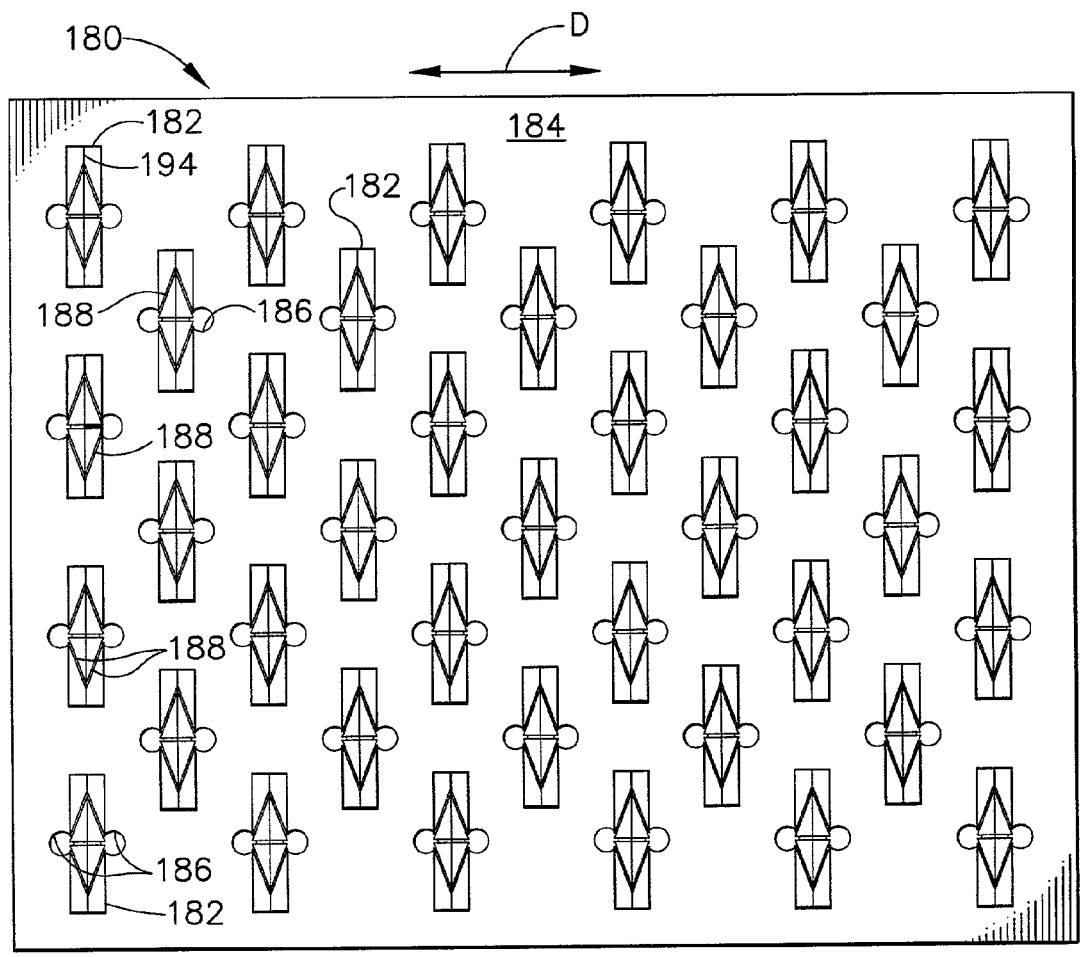
FIG. 17 is a plan view of an array of the elongated triangular microelements of FIG. 15 with the addition of through-holes in the substrate, and elongated channels along the surfaces of the triangular microelements.

FIG. 17 discloses a similar microelement array 180, which has triangular-shaped wedges as individual microelements 182 that are placed or are formed upon a base or substrate 184. In the "patch" 180, there are multiple through-holes 186 and channels 188 for placing at least one active on the skin.

Figure 18:
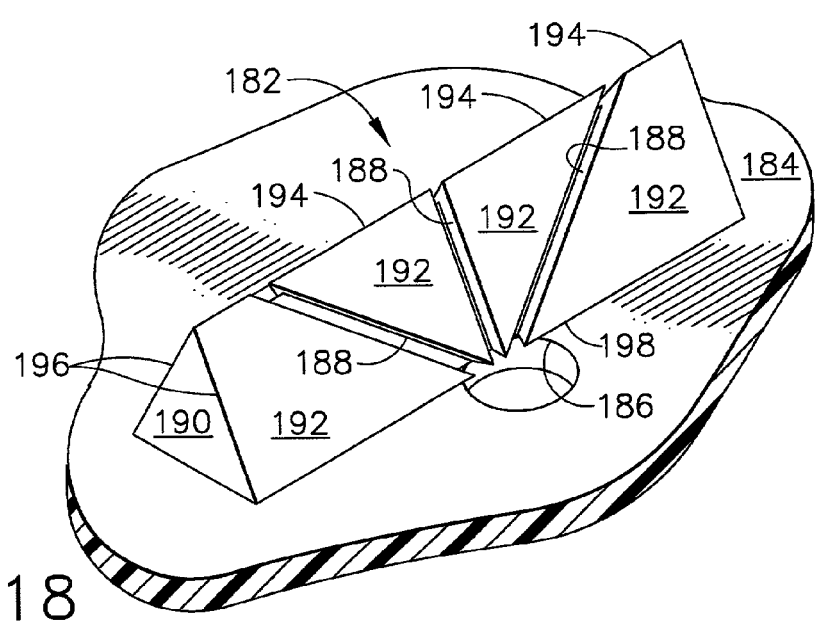
FIG. 18 is a perspective view of one of the elongated triangular microelements of FIG. 17.

FIG. 18 shows the channels 188 and holes 186 in a magnified view, in which the holes 186 would typically be designed to penetrate entirely through the substrate 184; however, such holes 186 could only partially penetrate the base if they connect to some other type of passageway within the base structure itself.

The triangular shape of the microelement 182 is seen on FIG. 18 along the side wall 190, which connects to sloped, rectangular side walls 192 along edges 196. A top edge 194 exists between the two triangular side walls 190, and a base line 198 marks the line between the microelement 182 and the substrate 184.

On FIG. 18, there are three separate channels 188 in the surface of the elongated side wall 192. Of course, fewer channels could be utilized, if desired, or even more numerous channels could be used. These channels 188 lend themselves well for capillary action to allow at least one active to flow through the holes 186 and along the channels 188 onto a skin surface, even after the areas between the microelements 182 become substantially full of dead skin cells and other foreign substances.

The triangular wedge structures of both FIGS. 16 and 18 are designed to essentially scrape away dead skin cells without penetrating the skin itself. This is accomplished by moving the microelement patches 160 or 180 in a back and forth manner substantially in the direction "D" as shown on FIGS. 15 and 17. Of course, if the microelement patches were to be moved in a different direction, particularly one that was perpendicular to the line "D" (which is a preferred, predetermined direction), then it is quite likely that the skin would be cut and penetrated. This has much usefulness, however, that concept is not directly a part of the present invention. Instead, that type of methodology is disclosed in a companion patent application, filed on Sep. 14, 2001, under Ser. No. 09/952,391, that is also assigned to The Procter & Gamble Company, and having the title "Microelements for Delivering a Composition Cutaneously to Skin."

Figure 19:
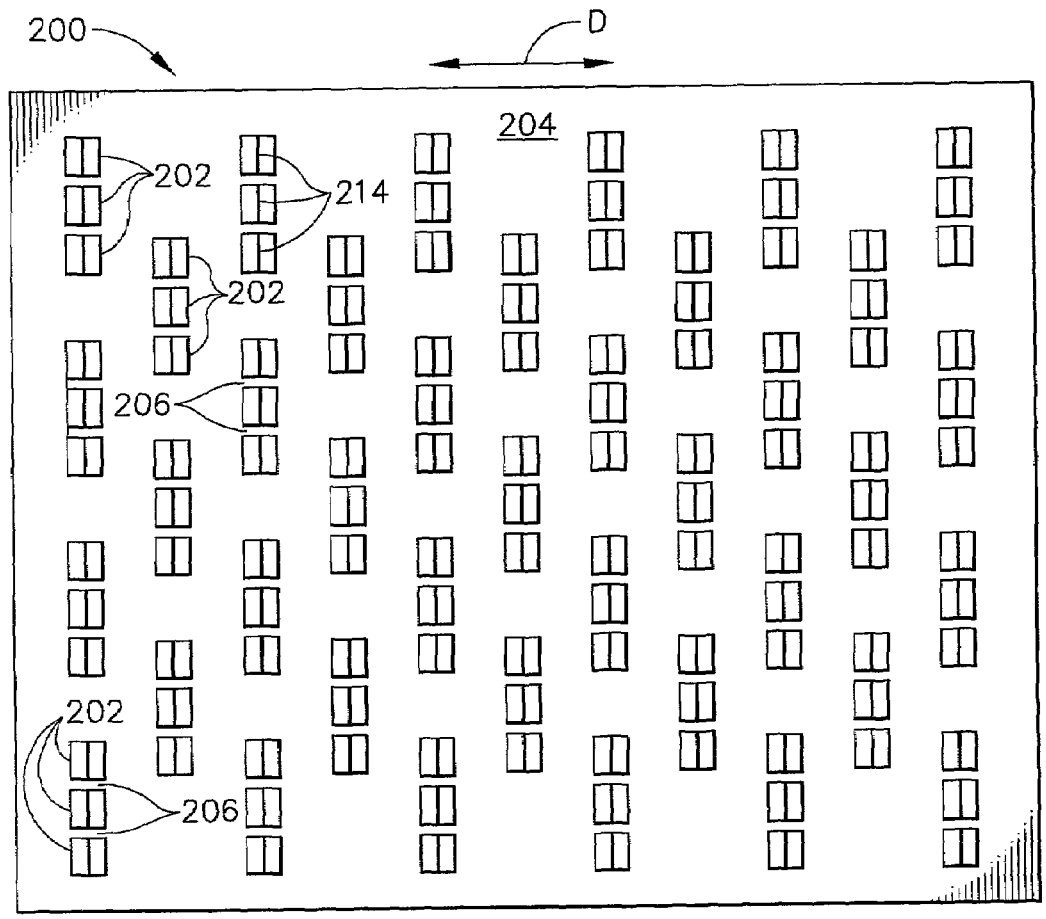
FIG. 19 is a plan view of an array of triangular-shaped wedge microelements that are grouped in closely-spaced arrangements, as constructed according to the principles of the present invention.
Figure 20:
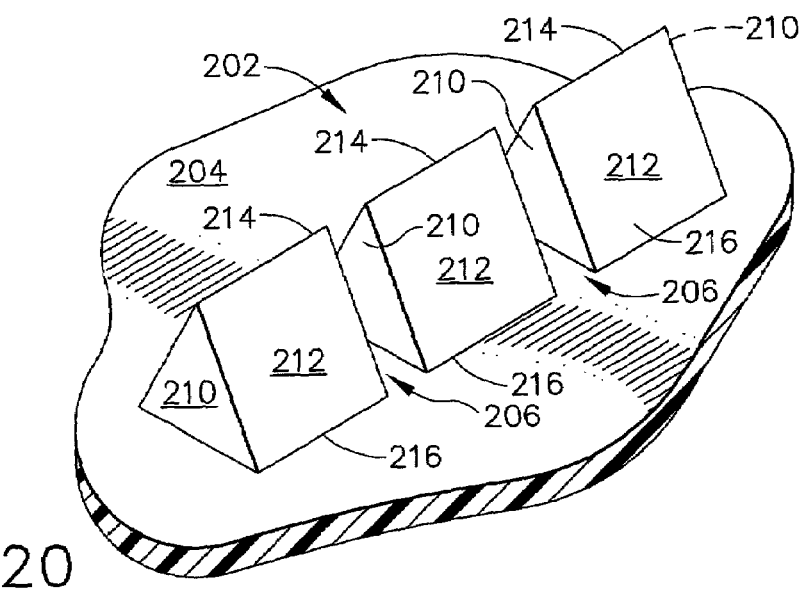
FIG. 20 is a perspective view of one of the closely-spaced triangular wedge microelements of FIG. 19.

Another refinement of the triangular-shaped wedge is illustrated on FIGS. 19 and 20. On FIG. 19, a microstructure array or patch 200 is illustrated as containing multiple wedge-shaped microelements 202 that are placed upon, or are formed thereon, a base or substrate 204. As seen in FIG. 20, each of the microelements 202 is comprised of three separate triangular-shaped wedges, each having a space therebetween at 206.

On FIG. 20, it can be seen that the three sections of the triangular-shaped wedge 202 includes a triangular-shaped side wall 210, a pair of rectangular, sloped side walls 212, a top edge 214, and a base line at 216 where the microelement 202 joins the substrate 204. Each of the three wedge shapes is separated by a space 206, in which a center triangular wedge shape is surrounded on both sides by a second, outer similar wedge shape, and spaced apart from each of these outer wedge shapes by the spacing area 206.

The "new" spaces 206 provide more trapping area between the closely-spaced wedges of the microelement 202. Therefore, a further amount of material should accumulate within these spaces, thereby trapping more dead skin cells and other foreign substances for a given microelement array or patch 200. As in the case of these embodiments described above, the amount of material that will be removed and then accumulated from the skin surface will depend upon the height of the microelements 202 and the spacings therebetween. In this new structure of FIGS. 19 and 20, this will also depend upon the spacings 206 between the individual triangular wedges of the individual microelement 202.

The preferred use of the array or patch 200 is to apply the patch directly to the skin, and then rub the patch in a back and forth manner along the skin surface substantially in the direction "D" as seen on FIG. 19 (which is a preferred, predetermined direction). This particular design exfoliates quite well, but is not designed to also apply an active at the same time. Of course, through-holes and channels could be added to this structure, if desired, although that type of structure would probably be easier to construct when using the shape disclosed in FIG. 18 for the microelement 182.

Figure 21:
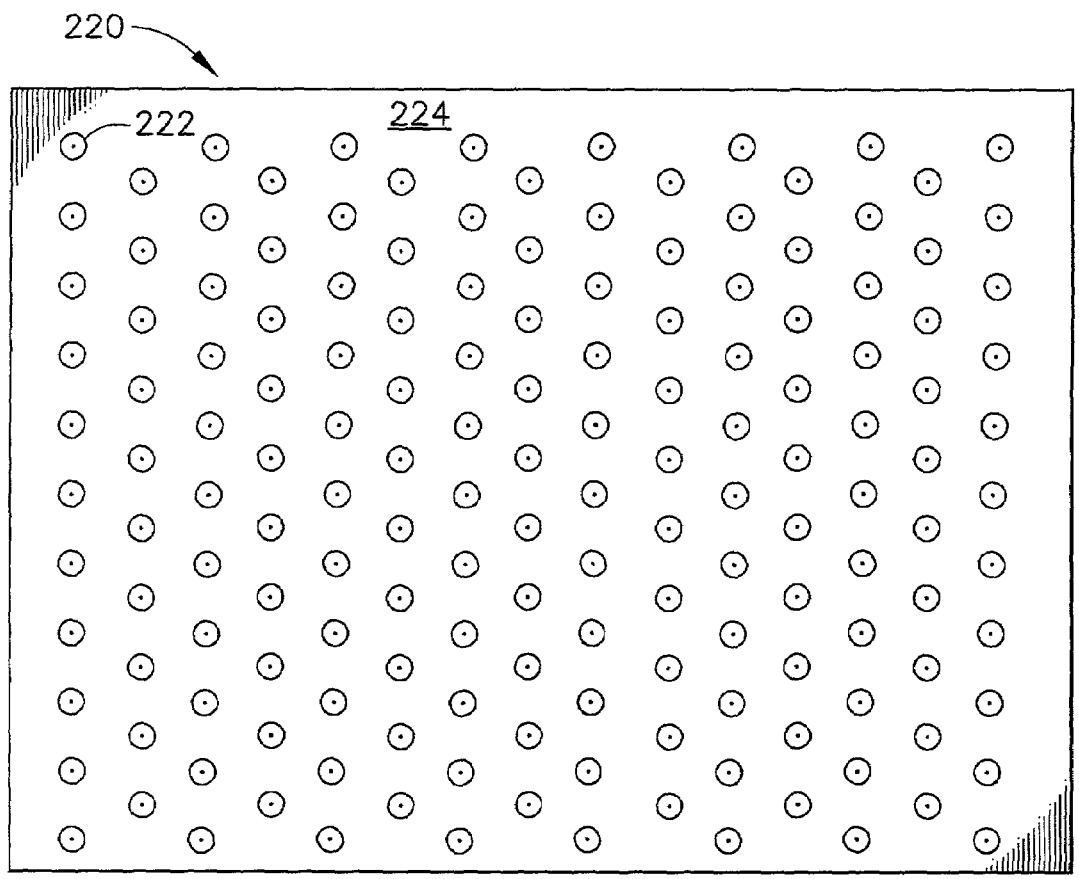
FIG. 21 is a plan view of an array of conical-shaped microelements, as constructed according to the principles of the present invention.
Figure 22:
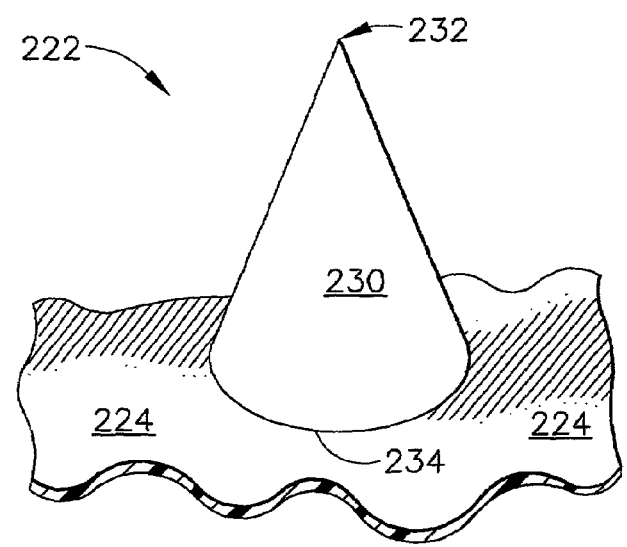
FIG. 22 is a perspective view of one of the conical microelements of FIG. 21.

FIG. 21 illustrates a microstructure array 220 that has multiple cone-shaped microelements 222 that are placed upon or constructed on a base or substrate 224. The individual microelements 222 are illustrated in greater detail in FIG. 22, in which each conical microelement 222 has a curved side wall 230, a peak 232, and a circular base "line" at 234. If desired, the conical shape of the microelement 222 could be somewhat truncated so that it does not come to a perfect point at 232. One advantage of having the curved side wall 230 is that it will more easily de-mold, thus simplifying fabrication.

The individual columns of the conical microelements 222 can be offset from one another for such adjacent columns if desired, as viewed in FIG. 21. Alternatively, each of the columns of microelements could be identical to one another, with no offset. Yet another alternative could arrange several columns with various offsets before the microelement pattern repeats, or the offsets could be substantially random so that there is no repetitive pattern.

The conical microelements 222 on the array or patch 220 can be used for exfoliation in a manner as described above for other shapes of microelements. In this particular structure, the direction of motion of the array or patch 220 is not important with respect to removing the skin cells or other foreign substances from the skin surface. From that standpoint, the microstructure patch 220 is similar to the patches 10 and 30 disclosed in FIGS. 1 and 3. As before, the amount of dead skin cells and other substances that are accumulated depends upon the height of the individual microelements 222 as well as the spacings therebetween.

Similar to the patch 10, the array or patch 220 will correctly perform its functions of scraping and removing skin cells without regard to the direction of movement of the patch 220 with respect to the orientation of the individual microelements 222. In other words, these microelements 222 are omnidirectional in operation, and all directions are preferred, or even "predetermined."

Figure 23:
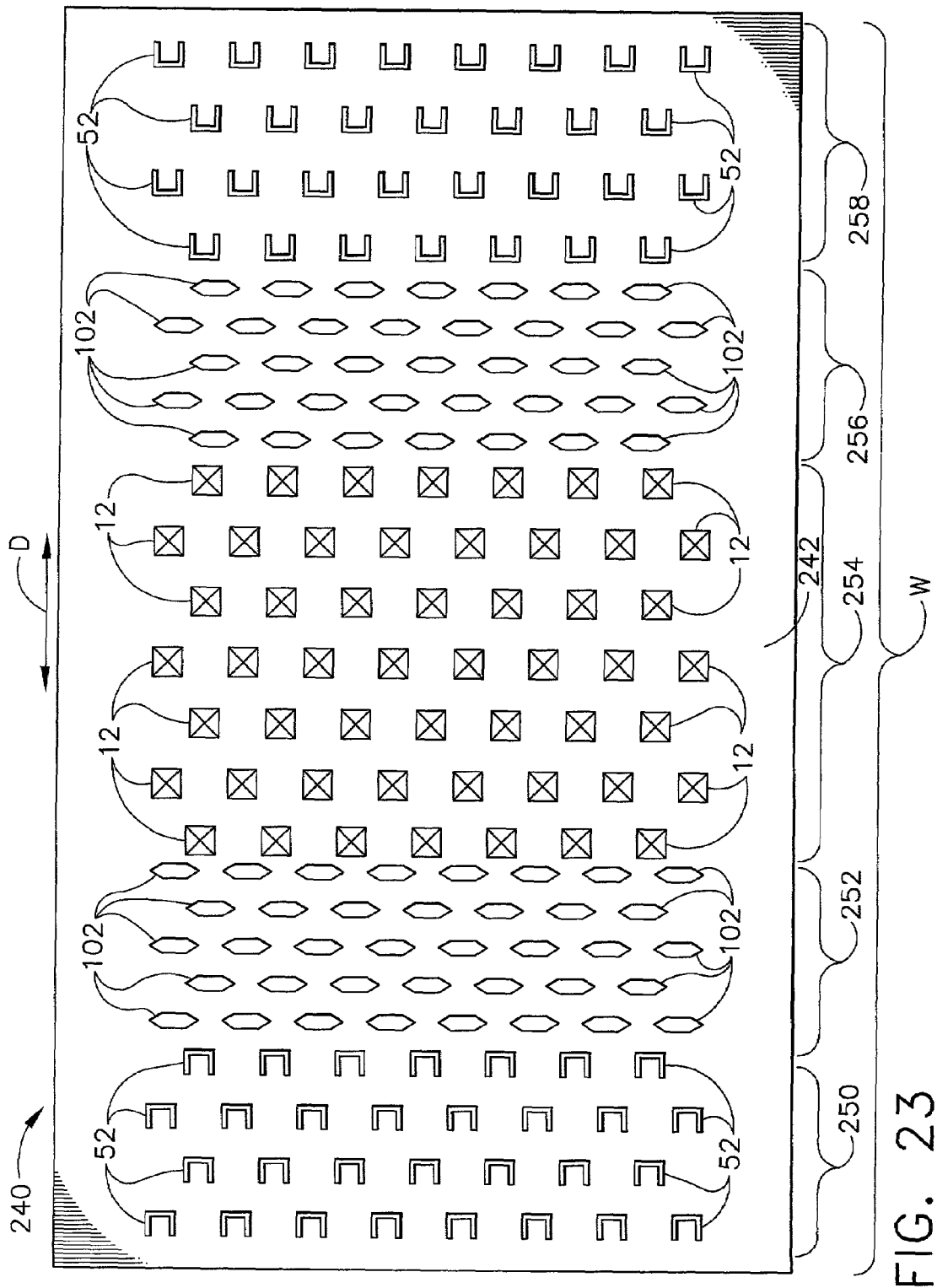
FIG. 23 is a plan view of a microelement array in which more than one microelement shape is constructed on the single substrate, as constructed according to the principles of the present invention.

FIG. 23 illustrates a microstructure array generally designated by the reference numeral 240 that contains more than one microelement shape upon its substrate 242. The different shapes are grouped in sub-arrays, which are designated by the reference numerals 250, 252, 254, 256, and 258. These multiple shapes on a single base or substrate could all be the same height, or if desired, could be of different heights. Furthermore, there could be through-holes or other types of passageways for delivering an active to a skin surface, or alternatively they could have no such passageways in the surface of the substrate 242 and the patch 240 could be used merely for exfoliation. On FIG. 23, the overall width of the array or patch 240 is designated by the dimension "W", which could be of any size necessary for a particular application.

On FIG. 23, the left-hand array 250 consists of multiple cup-shaped microelements 52, which were earlier described in reference to FIGS. 5 and 6. As seen in FIG. 23, these "open-box" or "cup-like" microelements 52 are facing to the left, which means that they would tend to accumulate skin cells when the array or patch 240 is moved toward the left along the arrow "D" (which is a preferred, predetermined direction). The width of this array 250 is about ⅙ W in the illustrated embodiment of FIG. 23; however, the width or array overall shape (i.e., it could be non-rectangular) could be easily varied, as desired.

A similar array of cup-like microelements 52 is arranged along the right-hand side (as seen in FIG. 23) in the array 258. These open-box microelements 52 would tend to accumulate skin cells when the microelement array or patch 240 is moved toward the right along the arrow "D" (which is still a preferred, predetermined direction). The width of this array 258 is also about ⅙ W in the illustrated embodiment of FIG. 23, but this too could be easily varied.

The microelements in the arrays 252 and 256 are illustrated as being the wedge-shaped elements 102 that were described above in reference to FIGS. 10 and 11. The middle array 254 is composed of the pyramidal microelements 12 that were described above in reference to FIGS. 1 and 2. The width of the arrays 252 and 256 are each about ⅙ W in the illustrated embodiment of FIG. 23; however, the width or array overall shape (i.e., it could be non-rectangular) could be easily varied for either of these arrays, as desired. Finally, the width of the middle array 254 is about ⅓ W in the illustrated embodiment of FIG. 23; however, as noted above, the width or array overall shape (i.e., it could be non-rectangular) could be easily varied, as desired.

If all of the microelements constructed on the array or patch 240 in FIG. 23 are of precisely the same height, this multiple microelement-shaped patch would nevertheless provide different treatments to the skin surface. For example, the pyramidal-shaped microelements 12 would provide a "fine" treatment and remove the smaller skin cells, while the wedge-shaped microelements 102 of the arrays 252 and 256 would provide a "medium" treatment and thereby remove somewhat larger skin cells. At the same time, the "end" arrays 250 and 258 that are composed of the cup-shaped (or open box) microelements 52 would provide a "coarse" treatment of the skin, and tend to remove the larger skin cells. In this manner, each individual area of the multiple-shaped array or patch 240 would tend to remove different sized skin-cells, thereby accomplishing a removal of at least most of all of the skin cells up to a certain depth into the stratum corneum. Of course, the types and sizes of skin cells that are removed could also be controlled by changing the height of some of the microelements of different shapes, if desired. As noted above, however, even if all of the microelements were of the same precise height, each of these array areas would tend to accumulate different sized skin cells.

It will be understood that a microelement patch could be composed of any one shape of microelements, or could be comprised of several different shapes on a single substrate or patch structure, without departing from the principles of the present invention. Moreover, it will be understood that the microelements disclosed herein could be of all the same height, or of different heights on the same substrate or patch, without departing from the principles of the present invention. Finally, it will be understood that minor modifications to the shapes disclosed in the drawings are contemplated by the inventors, and would still fall within the principles of the present invention.

It will also be understood that the microelement arrays or patches that contain through-holes or through-slots need not have such through-holes or through-slots for each and every one of the individual microelements that make up the array. In other words, the passageways that flow through the microelements (or adjacent thereto) could be constructed on only one-half of the microelements, if desired, while still achieving most of the results that would otherwise be achieved if such through-holes or through-slots were found at each of the microelements. Certainly, the holes or slots could be varied in size or diameter to either reduce or increase the amount of fluidic material that flows therethrough. All of these variations are contemplated by the inventors, and would fall within the principles of the present invention.

Figure 24:
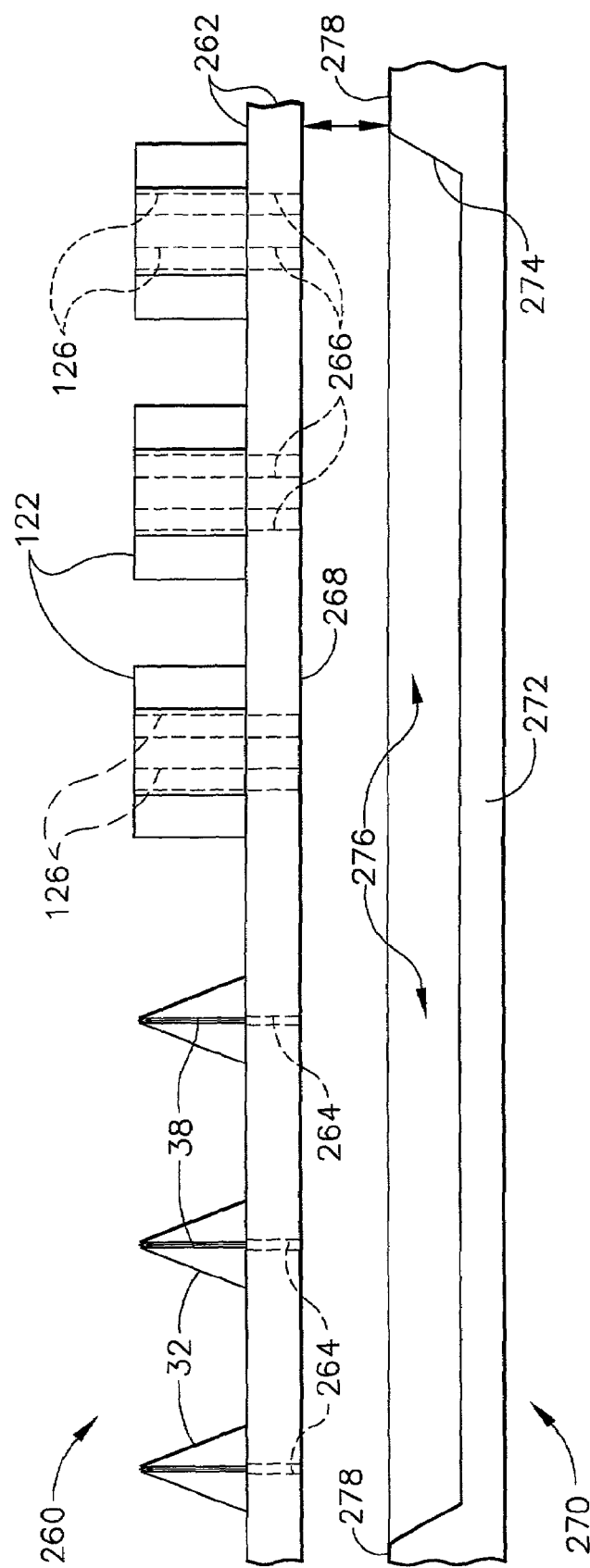
FIG. 24 is an elevational view in partial cross-section of an array of microelements similar to those found in FIG. 23, with the addition of through-holes or passageways to a reservoir structure below the main substrate.

FIG. 24 is a side elevational view in partial cross-section of a microstructure that contains an array of different shaped microelements and a corresponding substrate, designated at the reference numeral 260, as well as an underlying reservoir structure designated by the reference numeral 270. On FIG. 24, the array of microelements 260 is illustrated as having a set of pyramidal microelements 32 having grooves or channels 38 along the sides of the pyramid shapes, and a set of wedge-shaped microelements 122 having through-holes 126. The base or substrate is designated at the reference numeral 262.

On FIG. 24, the through-holes actually travel all the way through both the microelements and the substrate 262 to form passageways, and these passageways are depicted in two groups. The first group is a combination of the grooves or channels 38 in the pyramidal microelements 32 that are connected to the through-holes 264, to form a common set of passageways that extend from the bottom surface of the base or substrate 262 through the top surface of this substrate 262 and are in communication with the channels or grooves 38. The second set of passageways comprises a set of through-holes 266 that are in communication with the microelement through-holes 126 of the wedge-shaped microelements 122. These through-holes 126 and 266 must be in registration with one another to form complete passageways from the top of the microelement 122 to the bottom of the substrate of 262. Naturally, there could be some horizontal runs that connect similar passageways, if desired.

The bottom portion 270 depicted in FIG. 24 includes a reservoir structure that has a bottom wall at 272 and a reservoir area or volume at 276 that is bounded by the side walls of the reservoir at 274. Multiple such compartments or chambers can be constructed to house multiple actives. The upper portion of this reservoir structure 270 would typically be planar, as depicted at the reference numeral 278, and would make contact against the bottom surface at 268 of the microstructure/substrate apparatus at 260. It is important that the reservoir 276 be in communication hydraulically or pneumatically with the passageways 264 and 266, thereby allowing a fluidic drug or other active to reside within the reservoir confines at 276 until used, and then for the fluidic drug or active to be directed through the passageways 264 and 266 to the upper surface of the microelements 32 and 122.

Figure 25:
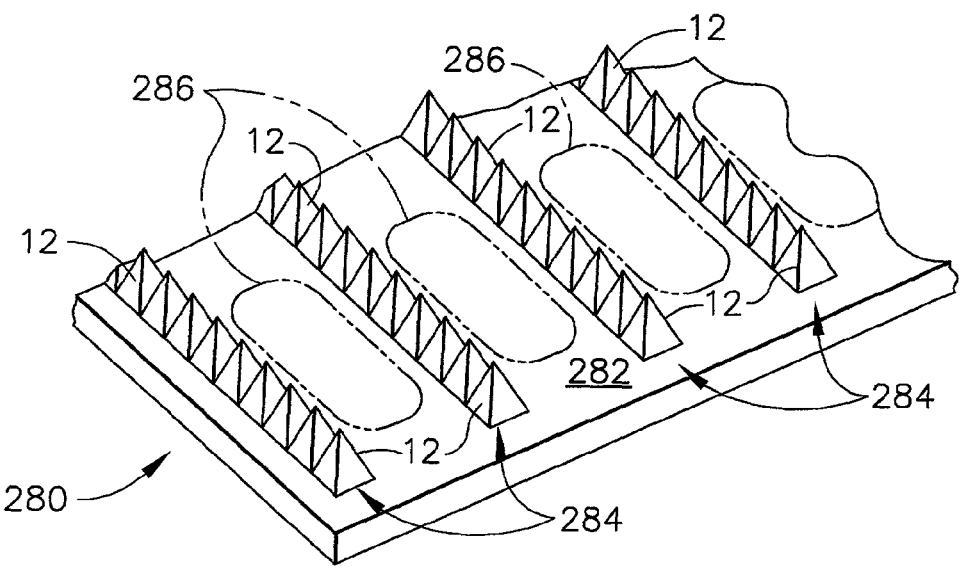
FIG. 25 is a perspective view of multiple arrays of pyramidal-shaped microelements, as constructed according to the principles of the present invention.

FIG. 25 illustrates a variation of the pyramidal microelements on a patch or array, generally designated by the reference numeral 280. Several columns of the pyramidal microelements are illustrated, in which the columns are at 284, and are composed of individual pyramidal microelements 12. These columns 284 of microelements are all built upon a planar substrate 282 of the array or patch 280. As can be seen in FIG. 25, there is no substantial space between individual microelements 12 within an individual column 284.

There is, however, a substantial space between adjacent columns 284, and these spacings are designated by the reference numeral 286 along the planar surface of the substrate 282. It is the spacings 286 that will accumulate skin cells and other foreign substances as these pyramidal microelements are used to exfoliate skin. In a preferred embodiment for use of the microelement array 280, the array/patch 280 will be placed upon skin and moved in a back and forth manner substantially along any line. Similar to the patch 10, the array or patch 280 will correctly perform its functions of scraping and removing skin cells without regard to the direction of movement of the patch 280 with respect to the orientation of the individual microelements 12. In other words, these microelements 12 are omnidirectional in operation, and all directions are preferred, or even "predetermined."

Figure 26:
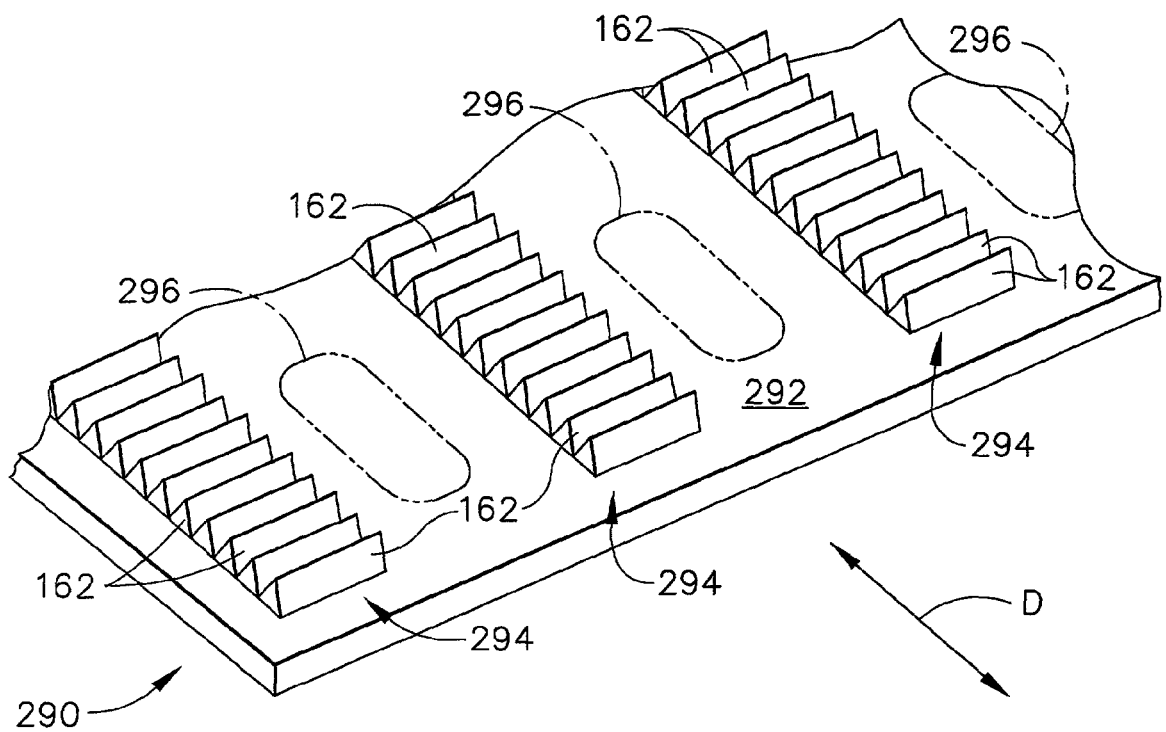
FIG. 26 is a perspective view of multiple arrays of elongated pyramidal-shaped microelements, as constructed according to the principles of the present invention.

FIG. 26 illustrates a similar arrangement of microelements, and includes multiple columns of pyramidal elongated microelements; its overall structure is designated by the reference numeral 290. The upper surface of the base or substrate 292 includes multiple columns 294 of elongated pyramidal microelements 162, in which there is no substantial space between each of the microelements 162 within a single column 294.

The individual columns 294 are spaced-apart from one another so that a planar area that is relatively open at the start is made available, at the areas designated by the reference numeral 296. These open areas 296 will receive the skin cells and other foreign substances on skin when the array/patch structure 290 is used to exfoliate the skin. In a preferred mode of use of the array/patch 290, the patch 290 will be placed upon skin and moved in a back and forth manner substantially in the direction of the arrow "D" (which is a preferred, predetermined direction).

Figure 27:
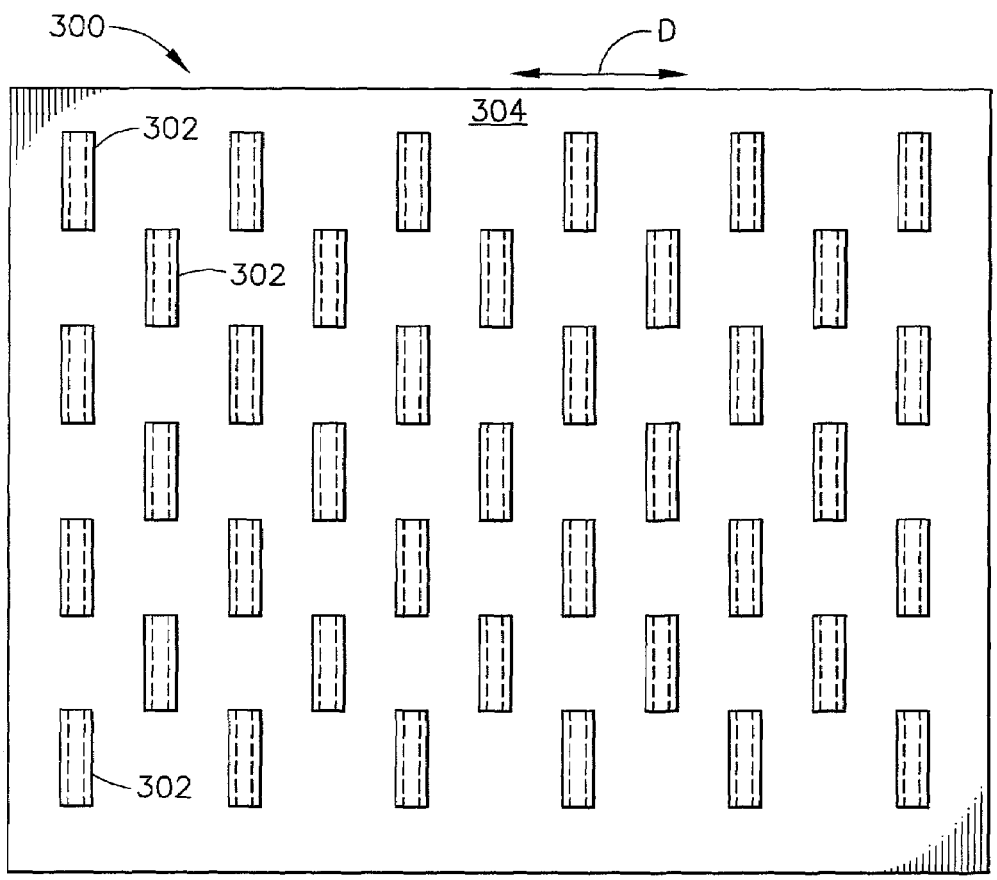
FIG. 27 is a plan view of an array of inverted wedge-shaped microelements, constructed as according to the principles of the present invention.

FIG. 27 illustrates an array of microelements, in which the array is generally designated by the reference numeral 300. The individual microelements 302 are arranged in columns on a substrate 304. The columns can have an offset of the microelements, as illustrated on FIG. 27. Alternatively, the individual columns of microelements 302 could be identical to one another, without any offset.

Figure 28:
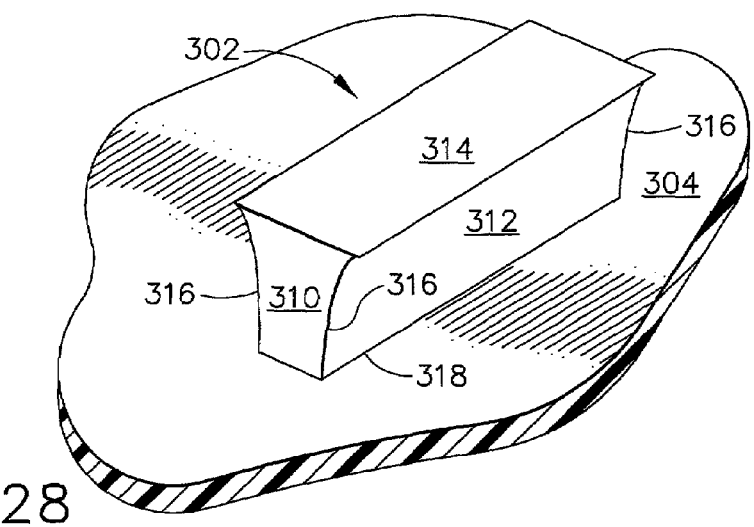
FIG. 28 is a perspective view of one of the inverted wedge-shaped microelements of FIG. 27.

FIG. 28 depicts one of the individual microelements 302 in greater detail. This microelement 302 has a shape that is something like an inverted curved wedge, or an inverted conical shape, as exhibited by one of its end walls 310. The curved edges of end wall 310 are depicted at 316, and a curved elongated side wall is depicted at 312. The top of the inverted wedge shape is depicted at 314, while the base line at 318 illustrates the point or line where the microelement 302 meets the substrate 304.

This inverted wedge shape is quite useful for exfoliation of skin, and can accumulate loose or dead skin cells and other foreign materials from the skin by use of a back and forth motion substantially along the line "D" (which is a preferred, predetermined direction). The height of the individual microelements 302 and the spacings therebetween will determine how much material will be removed from the skin surface.

Figure 29:
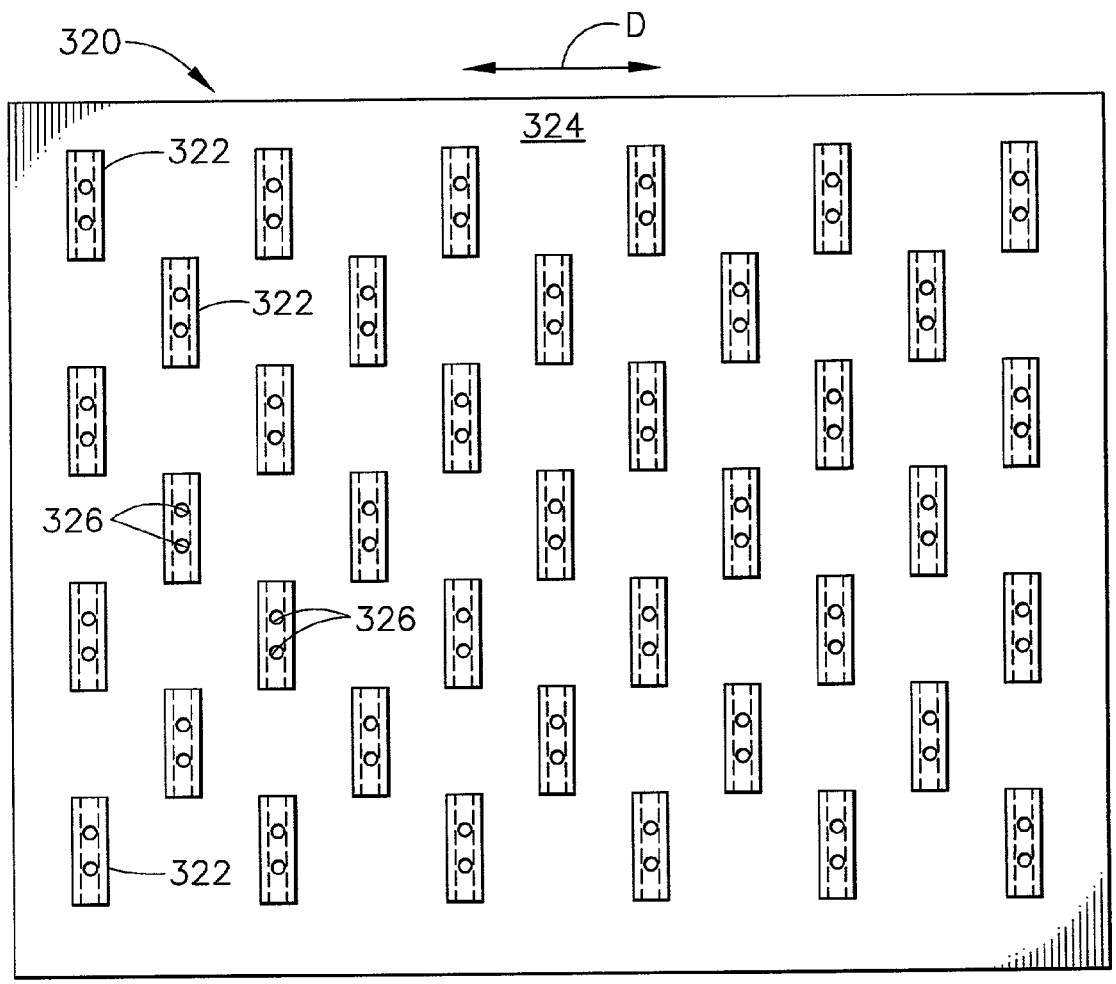
FIG. 29 is a plan view of an array of the inverted wedge-shaped microelements of FIG. 27 with the addition of through-holes in the microelements which penetrate through or into the substrate.

FIG. 29 illustrates an array 320 of similar inverted wedge-shaped microelements 322, which are mounted upon a substrate 324. In FIG. 29, the microelements 322 each include two through-holes 326, which are designed to pass one or more fluidic drugs or actives from one or more reservoirs to condition the skin after exfoliation.

Figure 30:
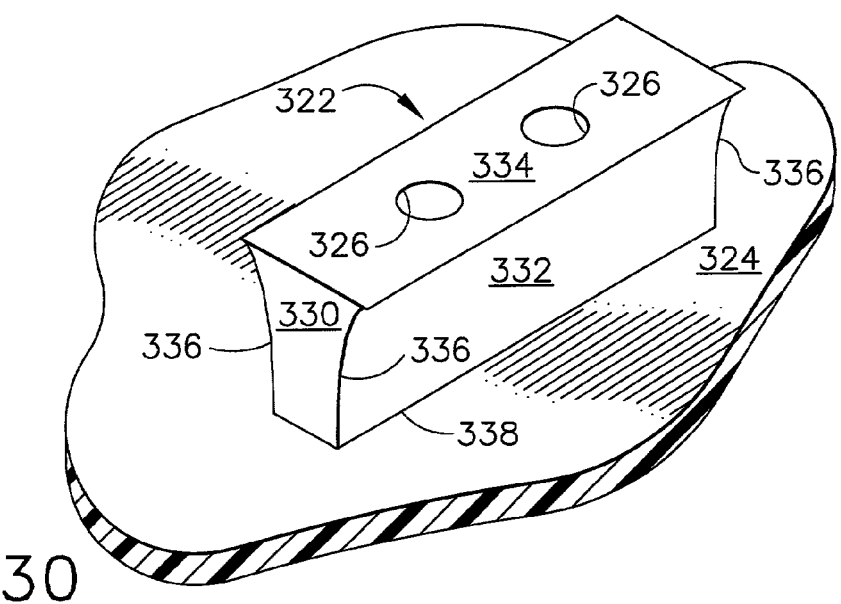
FIG. 30 is a perspective view of one of the inverted wedge-shaped microelements of FIG. 29.

FIG. 30 illustrates an individual inverted wedge microelement 322 in greater detail. The end wall 330 shows the overall shape of the inverted wedge (or inverted conical shape), which has two curved edges at 336 that adjoin the end wall 330 to adjacent elongated side walls 332. A top surface at 334 is illustrated as having the two through-holes 326, while a bottom base line 338 shows the line where the microelement 322 joins the substrate 324.

This inverted wedge-shaped microelement 322 can be used in a single operation for both exfoliation and for delivering at least one active to the skin surface. This active can be used to condition the skin just after many of the dead or loose skin cells have been removed.

Figure 31:
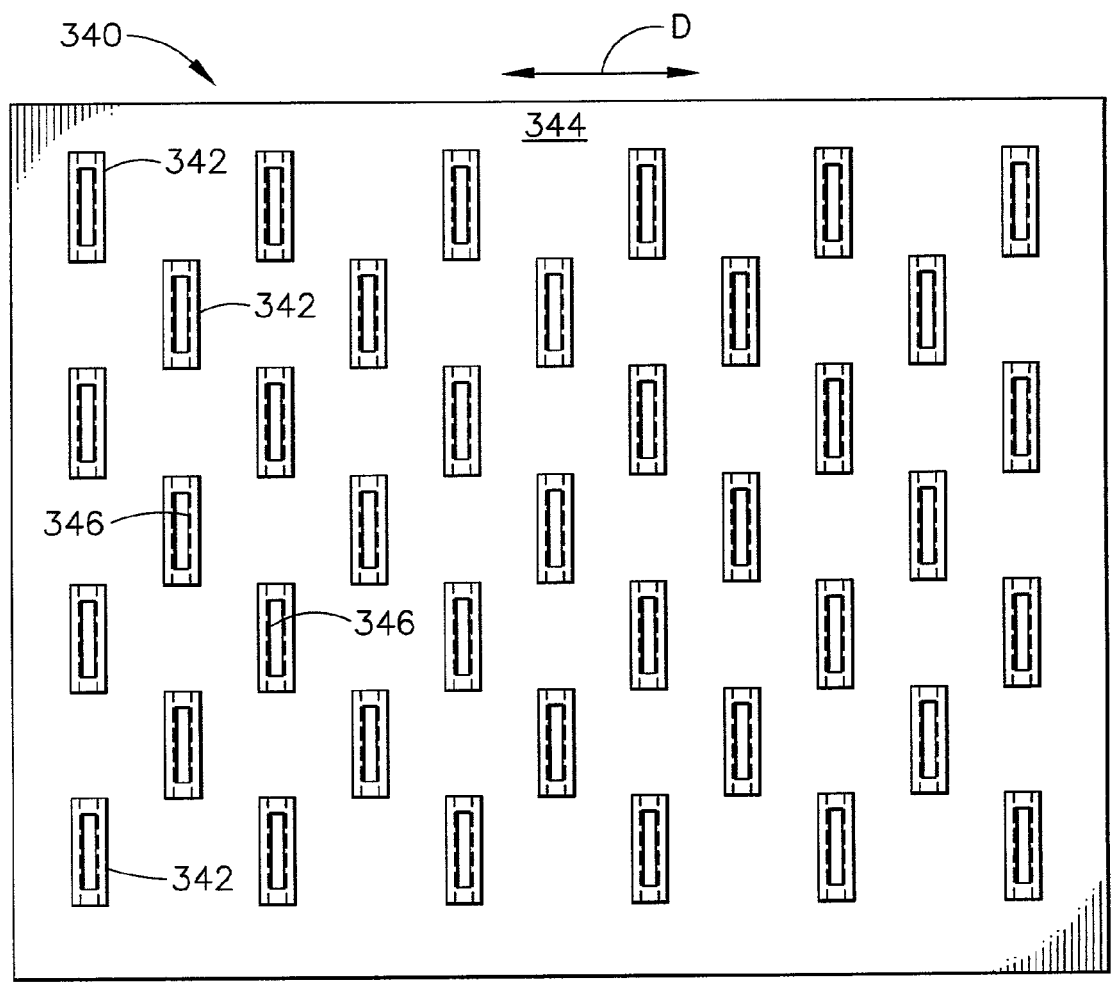
FIG. 31 is a plan view of an array of the inverted wedge-shaped microelements of FIG. 27 with the addition of through-slots in the microelements which penetrate through or into the substrate.
Figure 32:
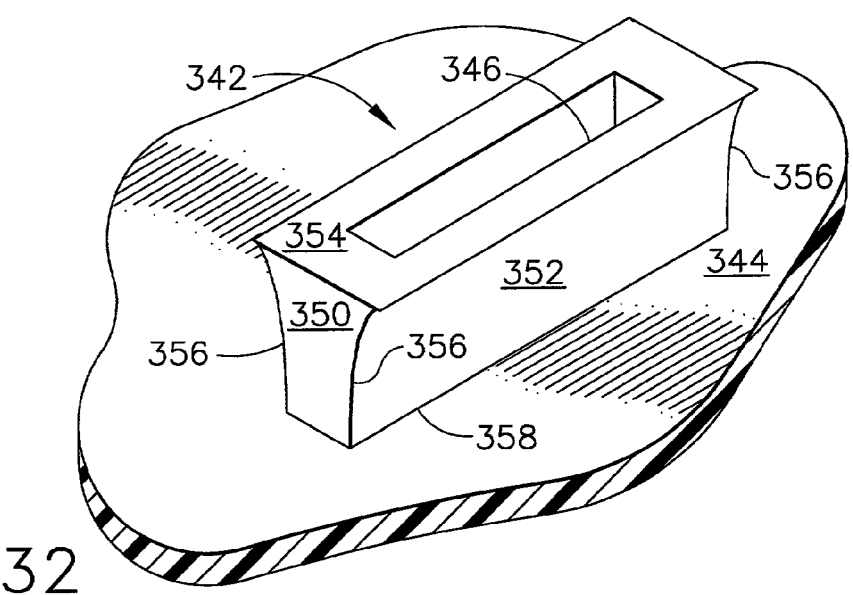
FIG. 32 is a perspective view of one of the inverted wedge-shaped microelements of FIG. 31.

An alternative structure for the inverted wedge microelement is illustrated in FIGS. 31 and 32. In FIG. 31, an array 340 of microelements 342 is depicted on a substrate 344. Each of the microelements 342 contains a through-slot 346, which can be seen in greater detail in the perspective view of FIG. 32.

In FIG. 32, the microelement 342 can be seen to have an inverted wedge shape (or inverted truncated conical shape) as exhibited by its end wall at 350. This end wall 350 is adjoined to adjacent elongated side walls 352 by curved edges 356. The top surface of the microelement is viewed at 354, while its bottom base line 358 illustrates the junction between the microelement 342 and the substrate 344.

The through-slot 346 can be used to deliver at least one active to skin, thereby making the array/patch 340 useable for both exfoliation and active delivery in a single operation. In a preferred mode of use, the array/patch 340 is placed on skin and then moved in a back and forth direction substantially along the line "D" (which is a preferred, predetermined direction).

Figure 33:
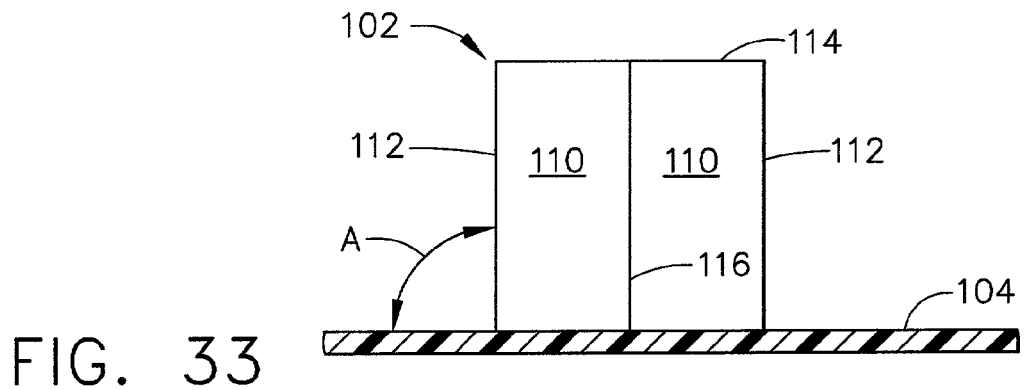
FIG. 33 is an elevational view in partial cross-section of a wedge-shaped microelement of FIG. 10, in which the side walls are perpendicular with respect to the substrate plane.

FIG. 33 illustrates the wedge-shaped microelement 102 from its "sharp" end in an elevational view. The two converging sides 110 are seen to form a relatively sharp edge at 116, which travels vertically from the top of the substrate/base 104 to the top surface 114 of the microelement 102. The angle "A" between the substrate top surface at 104 and the side wall 112 is clearly visible. On FIG. 33, this angle "A" is approximately 90°, and therefore forms a perpendicular angle.

Figure 34:
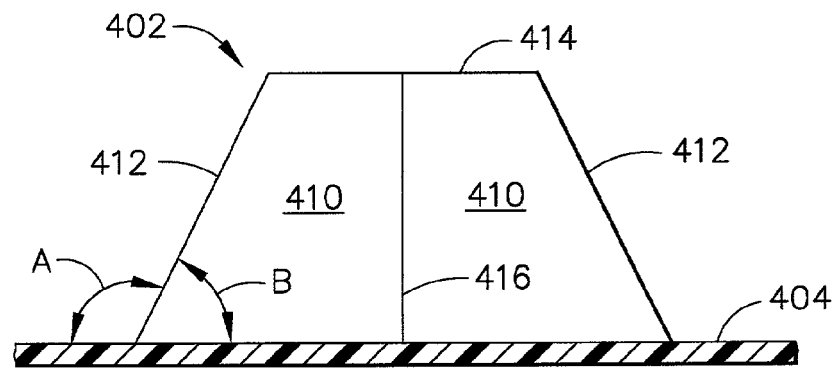
FIG. 34 is an elevational view in partial cross-section of a wedge-shaped microelement similar to that of FIG. 10, in which the side walls have an angular relationship that is not perpendicular with respect to the substrate plane.

FIG. 34 shows an alternative shape for a wedge-shaped microelement designated by the reference numeral 402. This wedge-shaped microelement has a similar appearance from above to that of the wedge-shaped microelement 102, except that its elongated side walls are not formed by a perpendicular angle to the substrate.

On FIG. 34, the substrate 404 is joined to the outer wall that is elongated along the side of the microelement (i.e., the wall 412) by an angle "A" that is greater than 90°. Its complimentary angle is illustrated at "B." Angle B is between 45° and 60° in FIG. 34, but of course could be any angle that will successfully operate to exfoliate the skin.

The front walls that converge are illustrated at 410, and converge along the relatively sharp edge at 416. This non-perpendicular wall shape of a microelement 402 may have some advantages with regard to manufacturing and with regard to overall strength of the structure.

Figure 35:
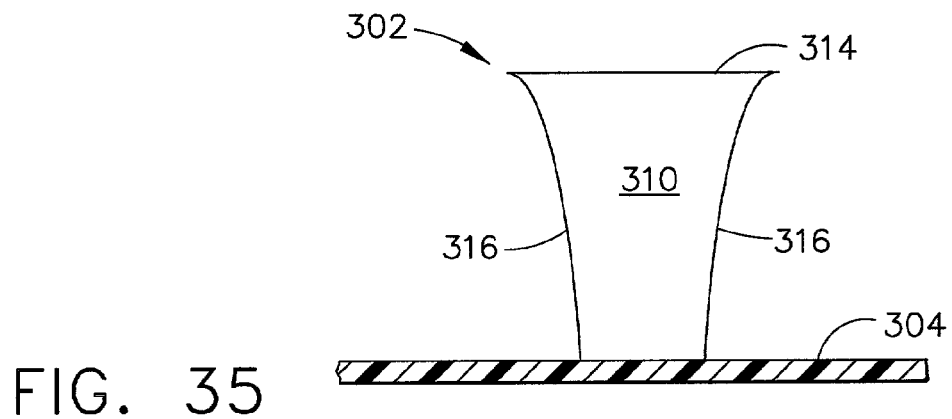
FIG. 35 is a side elevational view of an inverted wedge-shaped microelement of FIG. 28, in which the side walls are curved (i.e., concave).
Figure 36:
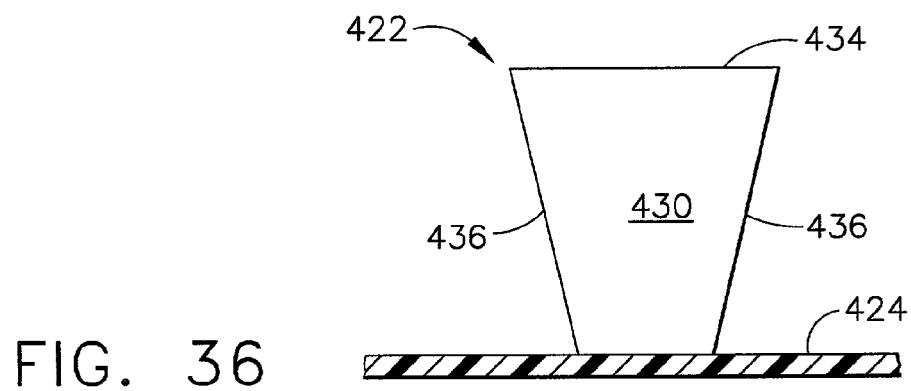
FIG. 36 is a side elevational view of an inverted wedge-shaped microelement similar to that of FIG. 28, in which the side walls are straight (i.e., flat).

FIG. 35 illustrates an end view of the inverted wedge or inverted truncated cone-shaped microelement 302. As can be seen, the side walls 316 are clearly curved in a concave manner. This is in contrast to the structure illustrated in FIG. 36, in which the microelement 422 has straight side walls 436. A similar top surface 434 exists as compared to the top 314 in FIG. 35. The overall shape of the end surface 430 is fairly similar to that of the end surface 310, but of course the shape in FIG. 36 is that of a truncated cone. The base/substrate is shown at 424.

Figure 37:
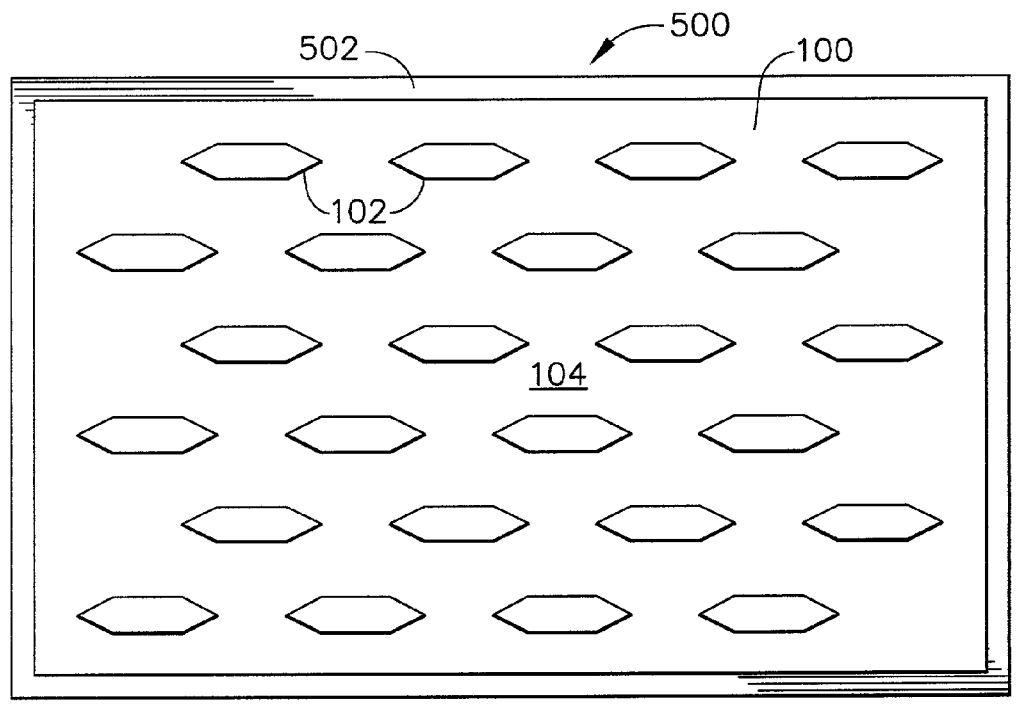
FIG. 37 is a plan view of a microelement array as seen in FIG. 10, with the addition of a non-woven backing material that is laminated to the original substrate.

FIG. 37 illustrates an array of wedge-shaped microelements 102 on a substrate 104 that makes up a microstructure apparatus designated by the reference numeral 100. Microstructure apparatus 100 comprises a top layer that is laminated to a non-woven backing 502, which is preferably thin enough so as to be substantially flexible. This overall structure is generally designated by the reference numeral 500 on FIG. 37.

The top layer 100 that contains the multiple microelements 102 can have as a substrate and microelement material some type of moldable plastic, such as nylon, or a polycarbide material, or PMMA, for example (and these materials may be used with any microelement shape). The bottom or backing material 502 preferably is a substantially flexible material that exhibits a soft texture. Typically a non-woven material gives an impression of cloth, and thus can provide the desired soft texture.

The non-woven backing material 502 can be laminated with the microelement layer 100 by use of a chemical glue or a heat-activated adhesive, for example. On FIG. 37, the non-woven backing is somewhat larger in length and width than the microelement layer 100, and thus can be seen along the edges.

Figure 38:
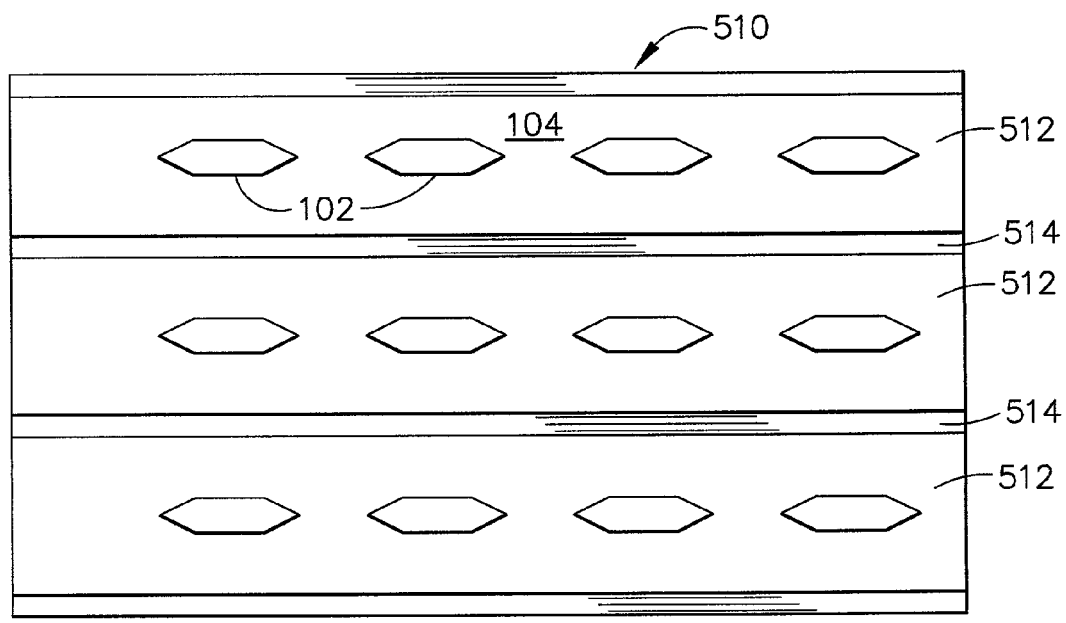
FIG. 38 is a plan view of a plurality of microelement strips that are laminated onto a non-woven backing.

FIG. 38 illustrates a similar laminated structure, however, the microelements 102 are formed as strips 512, in which there are several such strips that contain rows of the microelements. The non-woven backing material can be seen both along the top and bottom edges, and also between the strips at 514 on FIG. 38. The overall structure is generally designated by the reference numeral 510.

Figure 39:
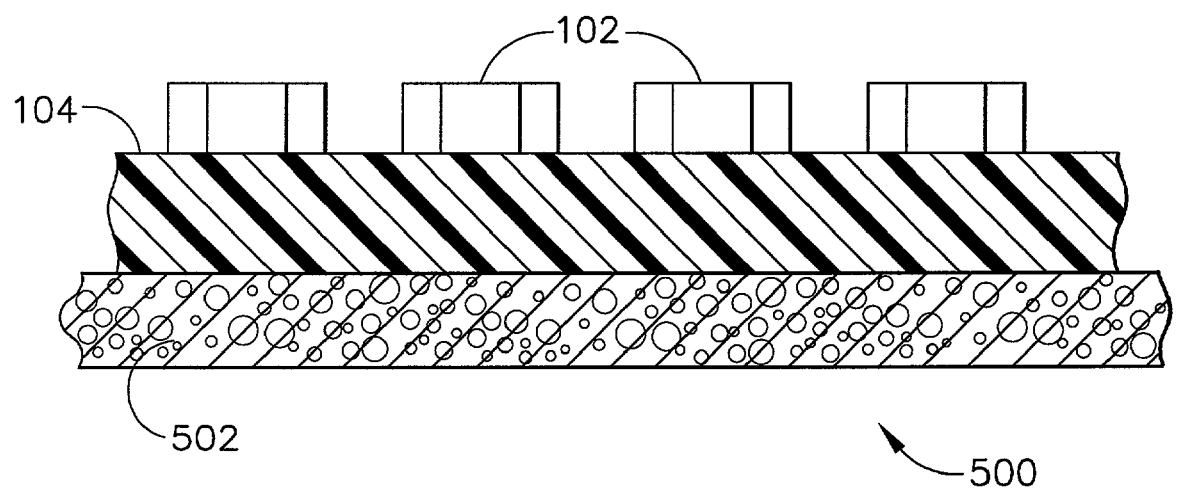
FIG. 39 is an elevational view in partial cross-section of a microelement array as seen in FIG. 10, showing further details of the substrate and non-woven backing.

In FIG. 39, the microelements 102 are visible at the top, as residing above the substrate 104. The bottom portion of the substrate is permanently affixed to the non-woven backing material 502, thus leading to the overall structure at 500.

As discussed above, the fixing of the non-woven backing material 502 to the substrate 104 can be by some type of adhesive used in lamination, or perhaps using a sonic bonding process. Alternatively, a co-extruded material could be used.

One major advantage to using a non-woven backing material as depicted in FIGS. 37–39 is that this non-woven material 502 (or 514 on FIG. 38) can be impregnated with at least one active, and thereby effectively become a "reservoir" without creating an actual chamber having an open volumetric space. This not only saves a manufacturing procedure step by not requiring a true open chamber to be constructed, but also allows the overall structure of the "patch" shown in the earlier figures to be made of a substantially flexible material that is much less likely to exhibit breakage problems.

It will be understood that various shapes of microelements can be used with the non-woven backing material, and various shapes of substrates can be laminated or otherwise affixed to the non-woven backing material. It will also be understood that the backing material may or may not be impregnated, all without departing from the principles of the present invention. Finally, it will also be understood that other suitable materials besides non-woven materials could be used for the backing at 502 and 514 on FIGS. 37 and 38, all without departing from the principles of the present invention.

Figure 40:
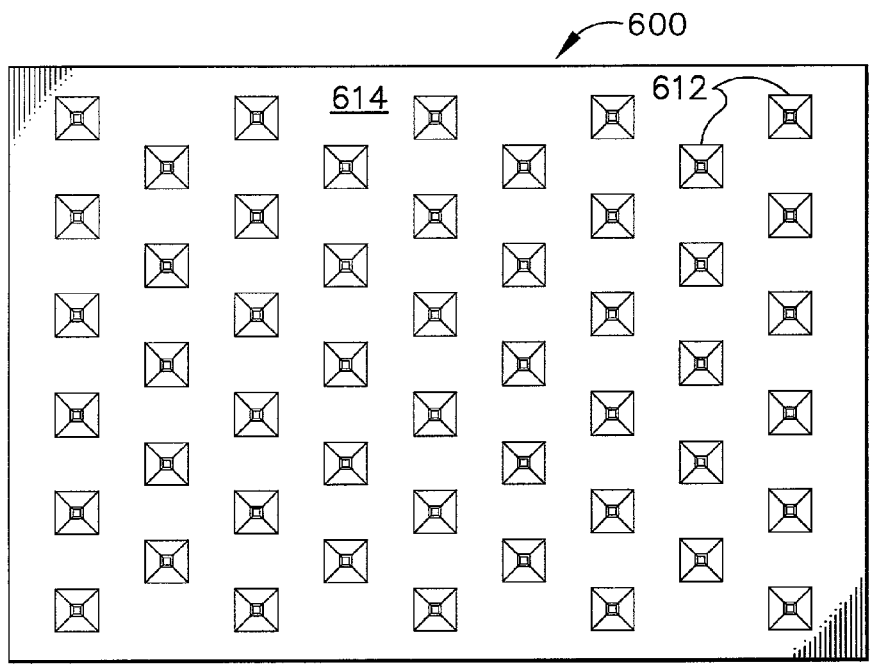
FIG. 40 is a plan view of an array of microelements that are partially pyramidal in shape, and which include through-holes in the microelements, as constructed according to the principles of the present invention.

Another alternative embodiment of the present invention is depicted in FIG. 40, in which a microelement array is generally depicted by the reference numeral 600. This microstructure 600 includes a large number of individual microelements 612, each of which extend from the proximal side or surface (i.e., the surface that can be viewed in FIG. 40) of the substrate 614. Each of the microelements 612 comprises a structure that is mainly a four-sided "partial" pyramid, as seen in a perspective view FIG. 41. The microelement 612 has sloped sides 620, each of which are bounded by an edge 622 between the various sides, and each of which has a base line at 626.

Figure 42:
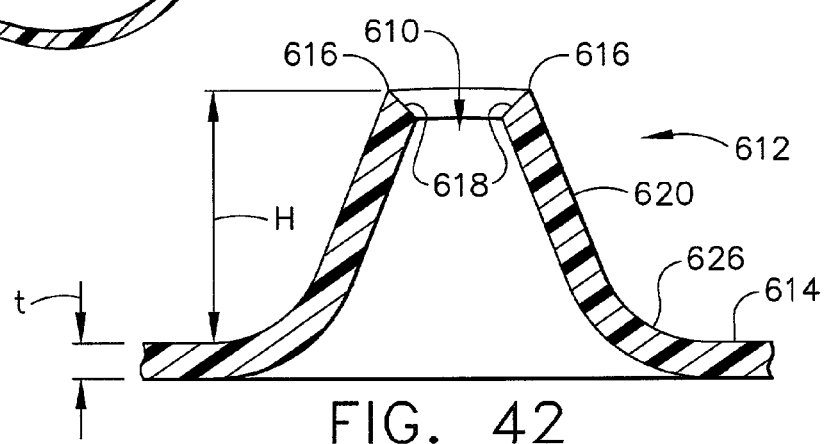
FIG. 42 is a side elevational view in cross-section of one of the partially-pyramidal microelements of FIG. 40.

In an exemplary embodiment of the present invention, the microstructure 600 is made of a plastic film that begins as a relatively thin planar structure. The microelements may be created by a continuous embossing operation, and as can be seen in FIG. 42, the initial thickness of the substrate 614 is indicated by the dimension "t," while the height of the microelement 612 is indicated by the dimension "H." In this embodiment, H>t, and moreover, the film is purposefully deformed beyond its "ultimate stress" characteristic, thereby fracturing along the top edges 616, and thereby forming an opening 610. The top edges 616 are the uppermost portion of the fracture lines at the reference numeral 618 (as can be best seen in the cross-section view of FIG. 42). The radius of top edges 616 can control the amount and type of exfoliated skin, and therefore, this radius can be optimized as a function of desired benefit.

The overall shape of top edges 616 provides substantially sharp cutting edges, similar to a blade. By use of this type of structure, the microelements 612 can be made to any desired length without the possibility of piercing the stratum corneum layer of the skin, because there are no focal discrete points of pressure created by the microelements 612. This is in contrast with the substantially sharp tips at 24 as viewed in FIG. 2 of the pyramidally-shaped microelement 12; such a sharp tip 24 will create a focal discrete point of pressure against the skin (i.e., where the force against the skin is concentrated).

As also can be seen on FIG. 42, the base line 626 could exhibit some curvature, although such curvature is not necessary. If there is any curvature, it will have the appearance of a curved surface that leads from the planar top (or "proximal") surface of the substrate 614 to the relatively flat, sloped sides 620 of the partially-pyramidal-shaped microelements 612. It will be understood that all base lines in this patent disclosure could have some curvature, or they could be composed of substantially flat surfaces which join in an angular relationship at a line (i.e., the base line). The precise shape of the base line is not a critical factor in the usefulness of the microelements of the present invention.

Figure 41:
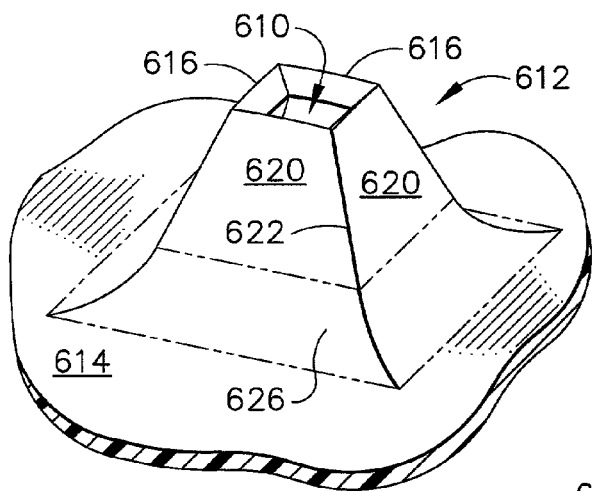
FIG. 41 is a perspective view of one of the partially-pyramidal microelements of FIG. 40.

Knowing the ultimate stress characteristics of a particular material, the maximum stress point can be predetermined to some accuracy, thereby predetermining the overall height dimension H, and also ensuring that the overall shape of the partial (or truncated) pyramid of the microelement 612 does not fully form a substantially sharp tip (this is the opposite of the embodiment illustrated in FIGS. 1 and 2, in which the pyramidal-shaped microelement 12 comes to a substantially sharp point at 24). In the embodiment of FIGS. 40–42, the microelements 612 will still have properties (i.e., one or more sharp edges) that will tend to scrape against skin and thereby perform an exfoliation procedure, but at the same time will not cause the same amount of skin irritation as compared to the embodiment described in FIGS. 1 and 2. The microelements 612 will provide a different "feel" to the skin of the user, and thereby reduce skin irritation, such as a rash that might otherwise occur. The end result is a set of microelement structures that appear to not be entirely formed, yet will exhibit a predetermined shape that is desired for a particular application on a user's skin surface. It will be understood that the microelements depicted in FIGS. 40–62 and described herein are still sufficiently sharp to perform the scraping action necessary for the exfoliation function—but they are not as sharp as the microelements described in the earlier figures (i.e., they are not "extremely" sharp).

Since the opening 610 extends all the way from the upper or proximal surface of the substrate 614 to the lower or distal surface of that substrate, a skin active compound can be stored along the lower portions of a microstructure 600 that is used to both exfoliate and then condition the skin by allowing the active compound to flow through the openings 610. It should be noted that the use of the microstructure 600 can be in any direction desired by the user—in other words, its "preferred" direction of use is omnidirectional.

Various types of materials could be used in the continuous embossing procedure for manufacturing the microstructure 600. It will be understood that the terms "emboss" or "embossing" as used herein encompass a pressing operation, or any type of fabrication step whereby a material is squeezed under pressure with or without the application of heat. It will also be understood that after the structures are formed, the upper surface of the overall microstructure 600 could be metalized in a separate process step, if desired. It will be further understood that the microstructure 600 can be used in a product or "assembly" that is much larger and has additional elements, such as an enclosed reservoir that will contain a skin active compound that will be used to flow through the openings 610.

Figure 43:
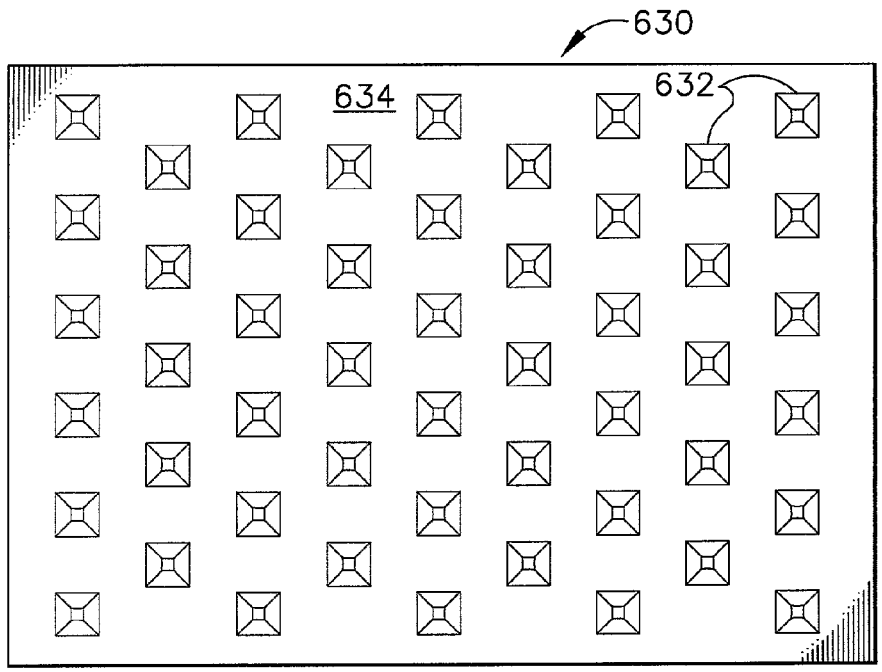
FIG. 43 is a plan view of an array of microelements that are partially pyramidal in shape, but which are solid in form, as constructed according to the principles of the present invention.

The embossing operation used to create the microstructure 600 can also be used to create a microstructure 630 that is illustrated on FIG. 43, in which an array of microelements 632 are created on the upper or proximal surface of the substrate 634, but do not exhibit an opening, such as the opening 610 in the microstructure 600. Instead, the partially pyramidal-shaped microelements 632 are formed up to a certain height (i.e., dimension "H"), however, this height H is not sufficiently large to cause the material to fracture during the embossing step. The resulting structure can be more easily viewed on FIGS. 44 and 45, in which the microelement 632 exhibits four sloped sides 640, with corner lines therebetween at 642, and has the appearance of a truncated pyramid. The top surface is illustrated at 638; this surface is relatively smooth, and has not fractured to create any type of opening.

Figure 45:
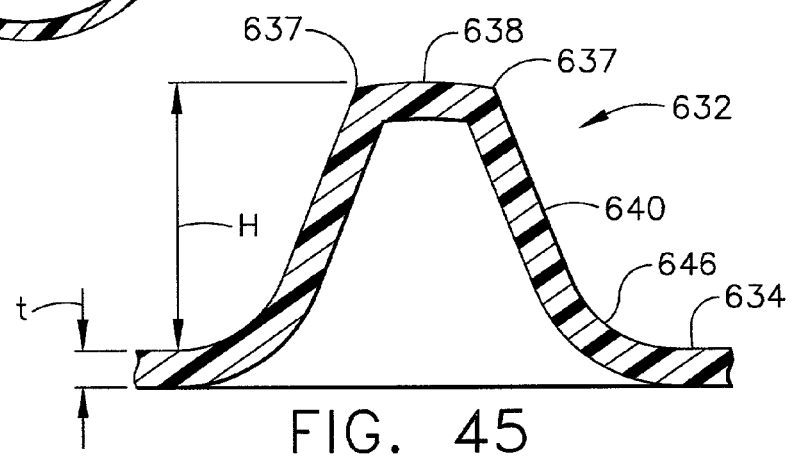
FIG. 45 is a side elevational view in cross-section of one of the partially-pyramidal microelements of FIG. 43.

As can best be seen on FIG. 45, the overall height dimension H is still greater than the thickness (i.e., dimension "t") of the plastic film that makes up the substrate 634. However, the height is less than that which would cause the material to undergo a stretching beyond its "ultimate stress" characteristic, and thereby the material does not fracture. In other ways, the partially-pyramidal shape of the microelement 632 is very similar to that of the microelement 612 seen on FIG. 41, and a base line at 646 is illustrated as being a curved surface between the relatively flat planar upper surface of the substrate 634 and the relatively smooth or flat walls 640 of the partially-pyramidal microelements 632.

It will be understood that the shapes of the microstructure 630 could be molded rather than being embossed, if desired. Furthermore, it will be understood that the upper surface could be metalized, if desired for certain types of applications. Since there are no openings between the proximal and distal surfaces of the substrate 634, the microstructure 630 would be generally useable for exfoliation procedures, but not for applying a skin active compound from a reservoir. However, some type of fluidic material could be first applied to the surface of skin, after which the microstructure 630 could be rubbed against that same area of skin to both exfoliate and to "press in" the skin active compound, if that is a desired result.

The radius of top edges 637 can control the amount and type of exfoliated skin, and therefore, this radius can be optimized as a function of desired benefit. The overall shape of top edges 637 provides substantially sharp cutting edges, similar to a blade. By use of this type of structure, the microelements 632 can be made to any desired length without the possibility of piercing the stratum corneum layer of the skin, because there are no focal discrete points of pressure created by the microelements 632.

Since the structure of the microelement 632 does not come to a substantially sharp point, the shape will provide a different "feel" to the user's skin as compared to the microelement 12 as seen on FIG. 2, which has a substantially sharp point at 24. This could be a significant improvement for some purposes in exfoliation procedures. The shape of the microelements 632 and their arrangement on microstructure 630 indicate that this microstructure can be used in an omnidirectional manner.

Figure 46:
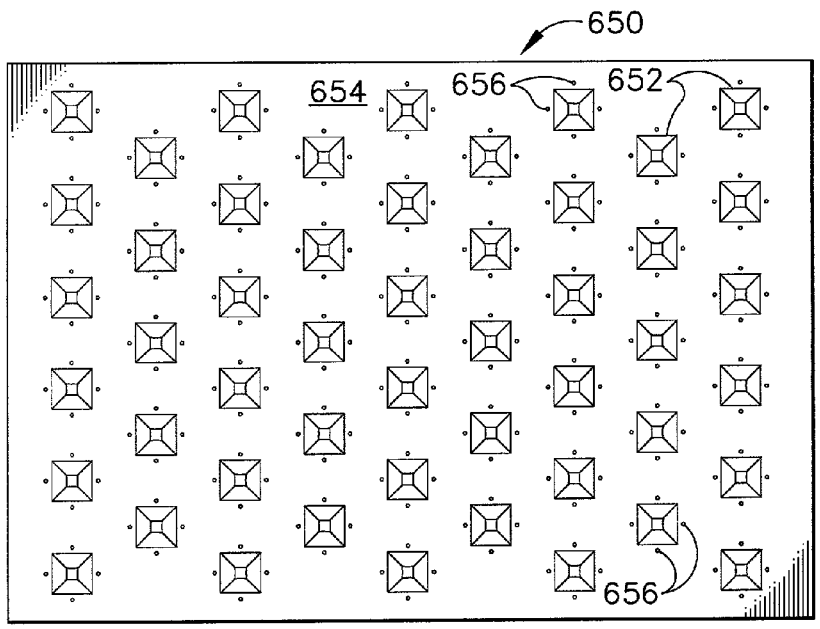
FIG. 46 is a plan view of an array of microelements that are partially pyramidal in shape but are solid in form, and which include through-holes in the substrate, as constructed according to the principles of the present invention.

FIG. 46 illustrates a microstructure generally designated by the reference numeral 650, which comprises an array of partially-pyramidal-shaped (or truncated pyramidal) microelements 652 that extend from a base or substrate 654. A large number of relatively small openings are made in the substrate, as indicated at 656. From the pattern of the array, and from the shape of the microelement 652, it can be seen that this microstructure 650 could be used in an omnidirectional manner.

Figure 44:
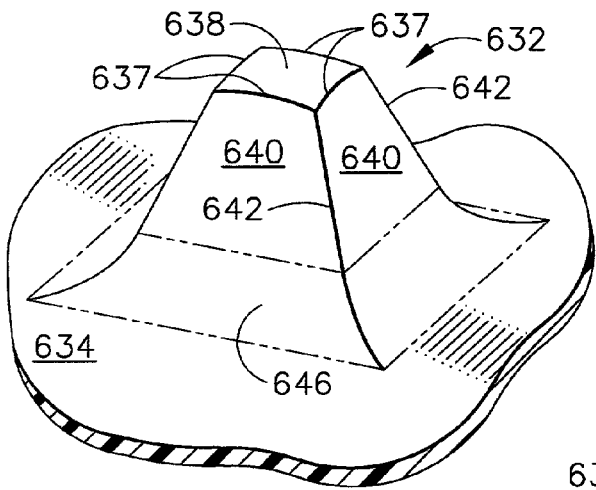
FIG. 44 is a perspective view of one of the partially-pyramidal microelements of FIG. 43.
Figure 47:
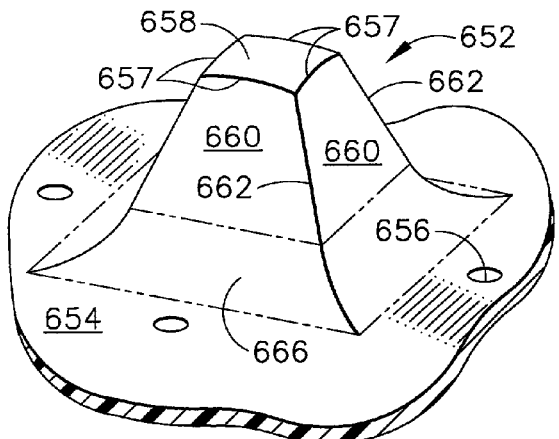
FIG. 47 is a perspective view of one of the partially-pyramidal microelements of FIG. 46.
Figure 48:
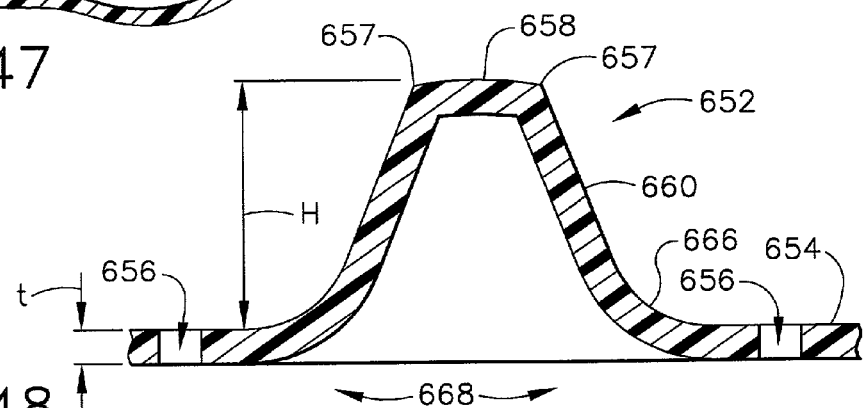
FIG. 48 is a side elevational view in cross-section of one of the partially-pyramidal microelements of FIG. 46.

As can be discerned from FIGS. 47 and 48, the microelements 652 are essentially identical to those microelements 632 seen on FIGS. 44 and 45. The main difference between microstructure 650 and microstructure 630 is the addition of the through-holes 656 that extend from the top or proximal surface of the substrate 654 through to the bottom or distal surface of that same substrate. In FIGS. 47 and 48, the side walls of the microelement are indicated at 660, which have edge lines at 662, and which meet the substrate at a somewhat curved surface transition referred to herein as the base line 666. The top surface of microelement 652 is indicated at 658, and has essentially the same size and shape as the top surface 638 of the microelement 632 in FIG. 44.

The radius of top edges 657 can control the amount and type of exfoliated skin, and therefore, this radius can be optimized as a function of desired benefit. The overall shape of top edges 657 provides substantially sharp cutting edges, similar to a blade. By use of this type of structure, the microelements 652 can be made to any desired length without the possibility of piercing the stratum corneum layer of the skin, because there are no focal discrete points of pressure created by the microelements 652.

As can be best viewed from FIG. 48, the overall height "H" is larger than the thickness "t" dimension, although as described before in reference to microstructure 630, the material used to create the microelement 652 is not stretched beyond its ultimate stress characteristic, and thereby does not fracture. Since the microstructure 650 exhibits a large number of through-holes 656, it could be fabricated by a molding operation if desired, rather than by embossing.

On FIG. 48, the area beneath the microstructures is indicated at 668. This is the area (or, more accurately, the volume) that could contain a fluidic compound, such as a skin active. When in use, the microstructure 650 is placed on the skin and rubbed against a particular area of the skin to exfoliate the skin, as described above in reference to other embodiments of the present invention. While the exfoliation is taking place, the fluidic compound in the volume or spaces 668 can flow through the through-holes 656 onto the skin surface, as desired.

Another alternative embodiment of microstructures of the present invention is illustrated in FIG. 49, in which the microstructure is generally designated by the reference numeral 670. A large number of individual microelements 672 extend from the upper or proximal surface of a base or substrate 674. This can best be seen in FIGS. 50 and 51. There are no through-holes shown in this particular embodiment.

As can be seen in FIGS. 50 and 51, the overall height of the microelement is given by the dimension "H" while the "final" thickness of the substrate is given by the dimension "d." In this embodiment of FIGS. 49–51, the dimension d is greater than or equal to the height dimension H, or expressed mathematically: $d \geq H$.

It can be seen from FIGS. 50 and 51 that the overall shape of microelement 672 is again a four-sided partial (or truncated) pyramid, in which the very top or "tip" of the pyramid is not fully formed, as can be seen by the top surface 678 not being extremely pointed in shape. This is by design, as the exfoliation procedure to be performed by microstructure 670 can still take place because of the overall height dimension H of each of the microelements 672; however the lack of a substantially sharp point at the top of the partial pyramid will reduce skin irritation and provide a different "feel" to the human user as that user rubs the microstructure 670 against his or her skin surface.

The radius of top edges 677 can control the amount and type of exfoliated skin, and therefore, this radius can be optimized as a function of desired benefit. The overall shape of top edges 677 provides substantially sharp cutting edges, similar to a blade. By use of this type of structure, the microelements 672 can be made to any desired length without the possibility of piercing the stratum corneum layer of the skin, because there are no focal discrete points of pressure created by the microelements 672.

The other features of the microelements 672 are very similar, in which there are sloped but relatively flat sides at 680, which are separated by angled edges 682, and which meet the substrate 674 at a base line 686, which is illustrated in FIGS. 50 and 51 as having some curvature. Once again, the arrangement and shape of the microelements is such that this microstructure 670 is omnidirectional in potential use. Since the final thickness of the substrate (i.e., dimension d) is greater than the height of the microstructure (at dimension H), it will be understood that an embossing procedure might be very difficult for this configuration, and that a molding operation might be preferred. The materials used would likely be plastic, although other types of moldable materials could be used if desired.

It also would be possible that a material having fairly high ductility characteristics could be pressed into this shape, rather than using a molding operation. In that circumstance, the initial thickness of the substrate could start out as a somewhat larger dimension than its final thickness (at dimension d) after the pressing operation has occurred. Moreover, it will be understood that, whatever the materials used to create the initial shapes, the upper surface could be metalized to provide control in reflectivity, thereby offering to consumers (users) a visual feedback as to the extent of exfoliation, or if desired, it could be coated with another material or compound for tailoring (or altering) friction, thereby customizing film and/or skin feel. It will be understood that the metalization (or other coating material) can be applied to every structure described herein.

Figure 52:
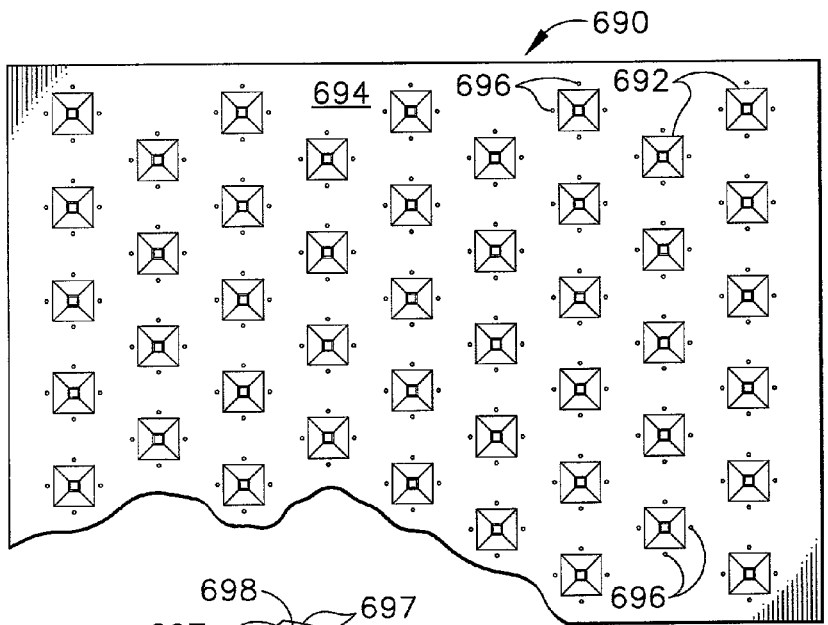
FIG. 52 is a plan view of an array of microelements that are partially pyramidal in shape and more elongated but are solid in form, and which include through-holes in the substrate, as constructed according to the principles of the present invention.

FIG. 52 illustrates a microstructure generally designated by the reference numeral 690 which contains an array of individual microelements at 692. These microelements extend from a substrate 694, and a relatively large number of openings or through-holes are illustrated at 696. This microstructure 690 is essentially the same in shape as the microstructure 670, in which the main difference is the addition of the through-holes 696.

The radius of top edges 697 can control the amount and type of exfoliated skin, and therefore, this radius can be optimized as a function of desired benefit. The overall shape of top edges 697 provides substantially sharp cutting edges, similar to a blade. By use of this type of structure, the microelements 692 can be made to any desired length without the possibility of piercing the stratum corneum layer of the skin, because there are no focal discrete points of pressure created by the microelements 692.

Figure 53:
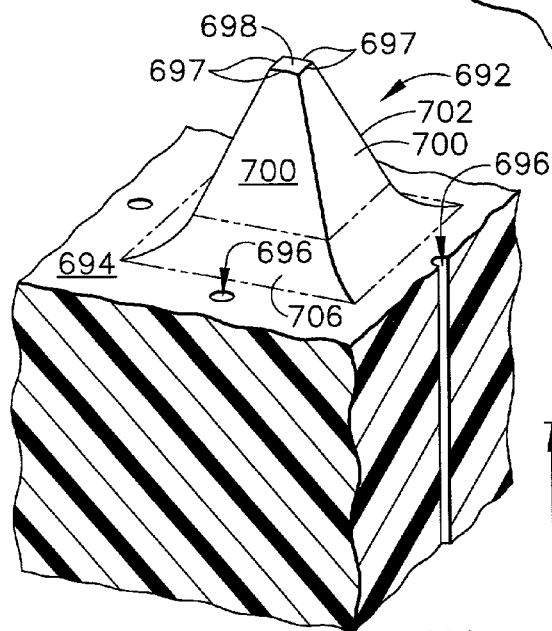
FIG. 53 is a perspective view of one of the partially-pyramidal microelements of FIG. 52.
Figure 54:
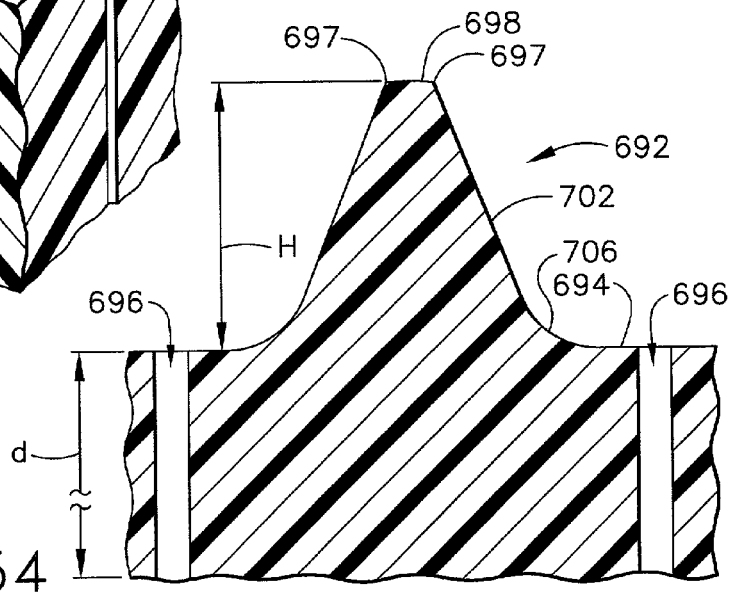
FIG. 54 is a side elevational view in cross-section of one of the partially-pyramidal microelements of FIG. 52.

The overall shapes of the microelement 692 are more easily viewed by inspecting FIGS. 53 and 54, where it can be seen that microelements 692 have the appearance of truncated four-sided pyramids, and where it is indicated that the overall height dimension "H" of the microelement 692 is smaller than the final thickness of the substrate at dimension "d." This is the same dimensional relationship as was discussed immediately above in reference to FIGS. 49–51. As before, the use of a plastic or other moldable material is probably called for in this type of microstructure, and a plastic molding operation would likely be preferred. However, it should be noted that a pressing operation could alternatively be used, if desired, also as discussed above in reference to FIGS. 49–51.

In FIG. 53, it can be seen that each microelement 692 comprises a four-sided partial pyramid that is not quite complete at its tip, such that an upper surface 698 is formed at its uppermost region. The sides of the partial pyramid are sloped at 700, which are separated by angled edges 702. The sloped sides meet the substrate 694 at a base line 706, which is illustrated on FIGS. 53 and 54 as having some curvature. As noted above in reference to the microstructure 670, the microelement 692 of this microstructure 690 can perform an exfoliation operation, but additionally the microstructure 690 can also provide some type of fluidic compound (such as a skin active) via the through-holes 696. In this situation, the microstructure 690 could be the top member of an overall application device for applying a skin active or other fluidic compound to the surface of skin, in which case the overall structure would include a reservoir or fluidic chamber that is located beneath the distal surface (not shown) of the base or substrate 694. It will be understood that the shape and orientation of these microelements 692 is such that microstructure 690 could be used in an omnidirectional manner.

It will be understood that the shape, size, and exact placement of the openings 696 can significantly vary over the surface of the substrate 694 without departing from the principles of the present invention. This statement is also true for the through-holes 656 of the substrate 654, illustrated in FIGS. 46–48. Moreover, it will be further understood that the overall size, shape, and placement of the microelements of all of the microstructures in FIGS. 40–54 can vary significantly without departing from the principles of the present invention. Certainly other shapes could be used which do not come to a substantially sharp point, if it is desirable to reduce skin irritation of the user when used in a manner that will exfoliate the skin.

In FIGS. 40–54, the microelements have been referred to as being partially-pyramidal in overall shape, since they are by design not expected to come to a substantially sharp point at their uppermost regions (or tips) at their distal ends. Alternatively, if these microelements were conical in shape, having a similar shape to the microelements 222 as viewed in FIG. 22, then once again they would be designed to not come to a substantially sharp point, such as the point 232 as seen on FIG. 22. As stated above, the lack of substantially sharp points will provide a different feel to the user of the microstructure, and will likely cause less irritation to the skin when in use.

Another alternative embodiment is illustrated in FIG. 55, which shows a microstructure generally designated by the reference numeral 710. Microstructure 710 contains a large number of microelements 712, which are generally rectangular in shape when seen from above (see FIGS. 55 and 57). Each microelement 712 has a set of sloped side walls and end walls, and has a slot-shaped opening or through-hole at 716 (see FIGS. 56–58 for details). These microelements 712 extend from the upper or proximal surface of a base or substrate 712. In the orientation of placement seen in FIG. 55, a preferred direction of use is indicated by the arrow "D."

Further details of the structure of microelement 712 are better viewed in FIGS. 56 and 57. The sloped side walls are indicated at 720, the sloped end walls are indicated at 724, and these end- and side-walls are each separated by an angled edge at 722. The sloped walls of the microelement 712 join the substrate 714 at a base line 726, which is illustrated on FIGS. 56 and 58 as having some curvature.

In an exemplary embodiment of the present invention, the rectangular-shaped microelements 712 can be manufactured using a continuous embossing operation, in which the initial thickness of the substrate 714 is indicated at a dimension "t" on FIG. 58, and the overall height of the microelement 712 is indicated by the dimension "H" on that same figure. This is another situation where the material is intentionally stretched beyond its ultimate stress characteristic, thereby fracturing at a predetermined location or height in the vertical direction, as seen in FIG. 58. The uppermost dimension of this fracture line is indicated at 718 on FIGS. 57 and 58. This fracturing edge 718 forms the surface that will come into contact with a user's skin during an exfoliation procedure. Since the actual fracturing event will cause an opening or through-hole to form at 716, some type of fluidic compound can be dispensed through the opening 716 from a reservoir or fluid chamber beneath the lower or distal surface of the substrate 714 onto the user's skin. Of course, an exfoliation procedure can simultaneously take place by which loose skin cells and other matter on the surface of the skin is essentially scraped loose from the skin, and accumulates in the areas between the individual microelements 712 on the surface of the substrate 714.

The radius of top edges 718 can control the amount and type of exfoliated skin, and therefore, this radius can be optimized as a function of desired benefit. The overall shape of top edges 718 provides substantially sharp cutting edges, similar to a blade. By use of this type of structure, the microelements 712 can be made to any desired length without the possibility of piercing the stratum corneum layer of the skin, because there are no focal discrete points of pressure created by the microelements 712.

Although not illustrated on FIGS. 55–58, it would also be possible to manufacture this type of rectangular microstructure such that the height dimension H is reduced so that the material does not fracture, thereby creating a microstructure that could be used for exfoliation, but would not contain openings within the microelements themselves. Other openings could also be added or designed into the substrate itself, as illustrated in previous embodiments of the present invention.

Figure 59:
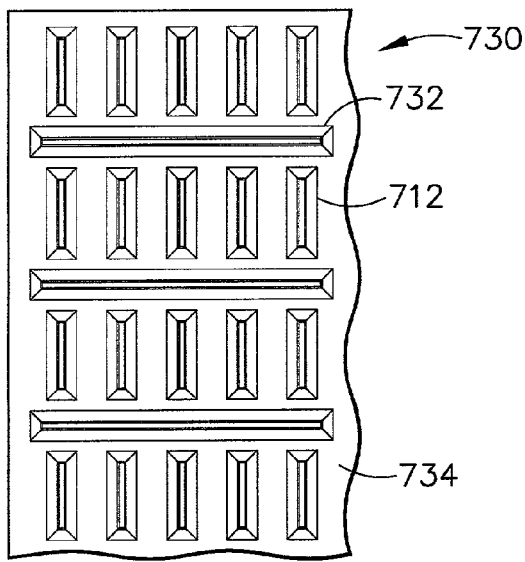
FIG. 59 is a plan view of an array of the mostly-rectangular microelements of FIG. 55, in which the microelements are of different sizes and are oriented in different directions.

FIG. 59 illustrates a microstructure 730 that contains an array of rectangular microelements 712, but also contains other larger rectangular microelements at 732. On FIG. 59, the microelements 732 are oriented at right angles to the smaller rectangular microelements 712. This orientation of the microelements allows the user to use the microstructure 730 in an omnidirectional manner. A fluidic compound could be dispensed through the openings in both the microelements 712 and 732. The use of two different sized rectangular microstructures could provide a different degree of smoothness or "feel" as a function of direction.

Figure 60:
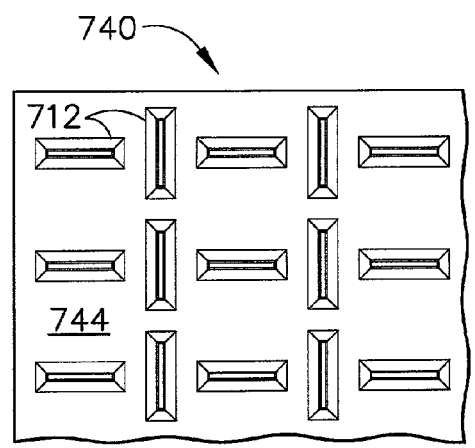
FIG. 60 is a plan view of an array of the mostly-rectangular microelements of FIG. 55, in which the microelements are oriented in different directions, thereby forming an array having an orthogonal-type pattern of "x" and "y" axis lines.

FIG. 60 illustrates a microstructure generally depicted by the reference numeral 740 which contains multiple individual microelements 712 in a predetermined pattern extending from a substrate 744. In microstructure 740, all of the multiple microelements 712 are of virtually the same size and shape. They are laid out in a relatively "neat" pattern generally forming an X-Y grid, which thereby has the appearance of an orthogonal pattern. Once again, by use of the microelements being oriented in more than one direction, the microstructure 740 is useable in an omnidirectional manner.

Figure 61:
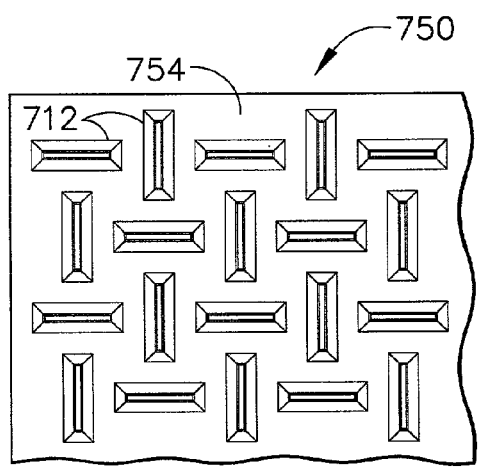
FIG. 61 is a plan view of an array of the mostly-rectangular microelements of FIG. 55, in which the microelements are oriented in different directions, thereby forming an array having a perpendicular-type pattern, but not in continuous lines.

Another variation of the use of these microelements 712 is illustrated on FIG. 61 in which a microstructure is generally designated by the reference numeral 750. The numerous microelements 712 extend from the top or proximal surface of a substrate 754, and are again oriented in an orthogonal manner with respect to the individual longitudinal directions of the individual microelement 712. However, they are not specifically laid out in a manner that has the appearance of an orthogonal X-Y grid, but instead are more tightly interspersed. However, since the microelements 712 are oriented in different directions, the microstructure 750 is useable in an omnidirectional manner.

Figure 62:
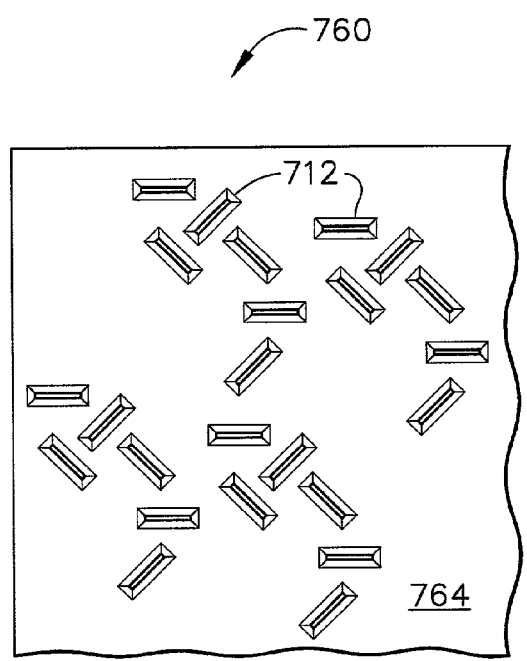
FIG. 62 is a plan view of an array of the mostly-rectangular microelements of FIG. 55, in which the microelements are oriented in different directions, thereby forming an array having a more irregular pattern.

A further variation using microelements 712 is illustrated on FIG. 62 in which a microstructure is generally depicted by the reference numeral 760. Multiple microelements 712 extend from the top or proximal surface of a substrate 764. In FIG. 62, the microelements 712 are arranged in multiple angular orientations, and appear to have a somewhat random pattern. More specifically, they are not laid out in an orthogonal manner that would have the appearance of an X-Y grid.

As seen in FIG. 62, the groupings or patterns of the microelements 712 can be repeated if desired, or they can be more or less randomly placed at various locations on the surface of the substrate 764. If equal numbers of microelements 712 are oriented at each angular relationship with respect to the other angular relationships of microelement orientations, then the microstructure 760 will have the capability of omnidirectional use. This is likely a preferred embodiment, so that there are no artificial restrictions on use by a human user for exfoliation procedures.

It will be understood that the exact size and shapes of the rectangular-type microelements depicted in FIGS. 55–62 can vary by a significant amount without departing from the principles of the present invention. It will also be understood that, while a continuous embossing manufacturing procedure may be preferred, certainly other manufacturing operations could be performed to create such microstructures, including injection molding of plastic materials. It will be yet further understood that the exact materials can vary to create these shapes without departing from the principles of the present invention, including a step of metalization of the upper or proximal surface, if desired.

Figure 63:
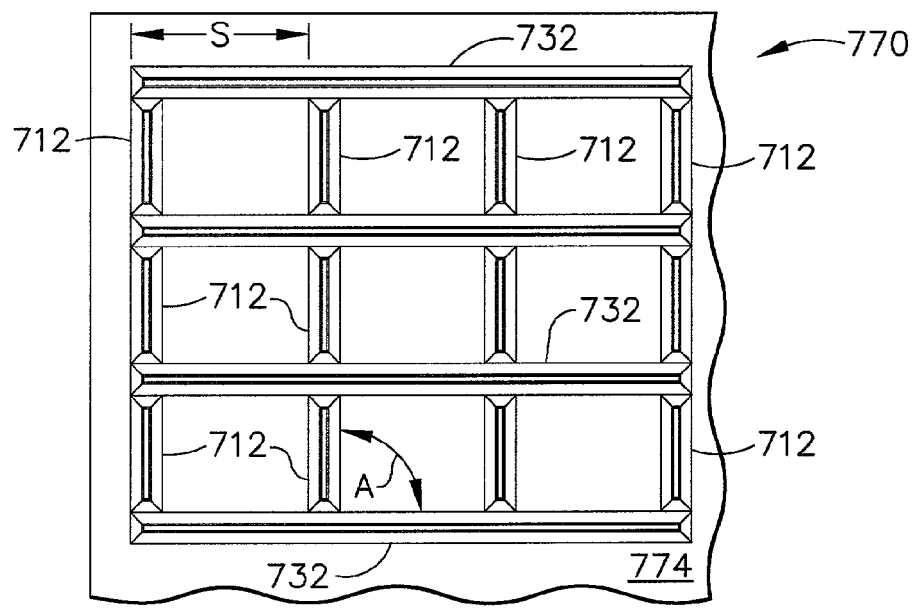
FIG. 63 is a plan view of an array of microelements similar to those of FIG. 55, which are mostly rectangular in shape but with sloped side walls and end walls, and which include through-slots in the microelements, and which are arranged in a closed box-like array pattern, as constructed according to the principles of the present invention.

FIG. 63 illustrates another microstructure that uses rectangular-shaped microelements 712, in which the microstructure as a whole is generally designated by the reference numeral 770. On FIG. 63, several of these microelements 712 are found in an array of such microelements that are closely abutted with lengthier rectangular-shaped microelements 732. In some ways this configuration is similar to that illustrated on FIG. 59. However, a significant difference in the microstructure 770 of FIG. 63 is that the microelements are oriented such that they virtually enclose areas therebetween, by use of the substantially "continuous edges" provided by these closely-packed microelements 712 and 732. Another way to describe this microstructure 770 is that the closely-packed microelements form an array pattern of "closed boxes," much like the appearance of a series of adjacent reservoirs from a high altitude.

Figure 64:
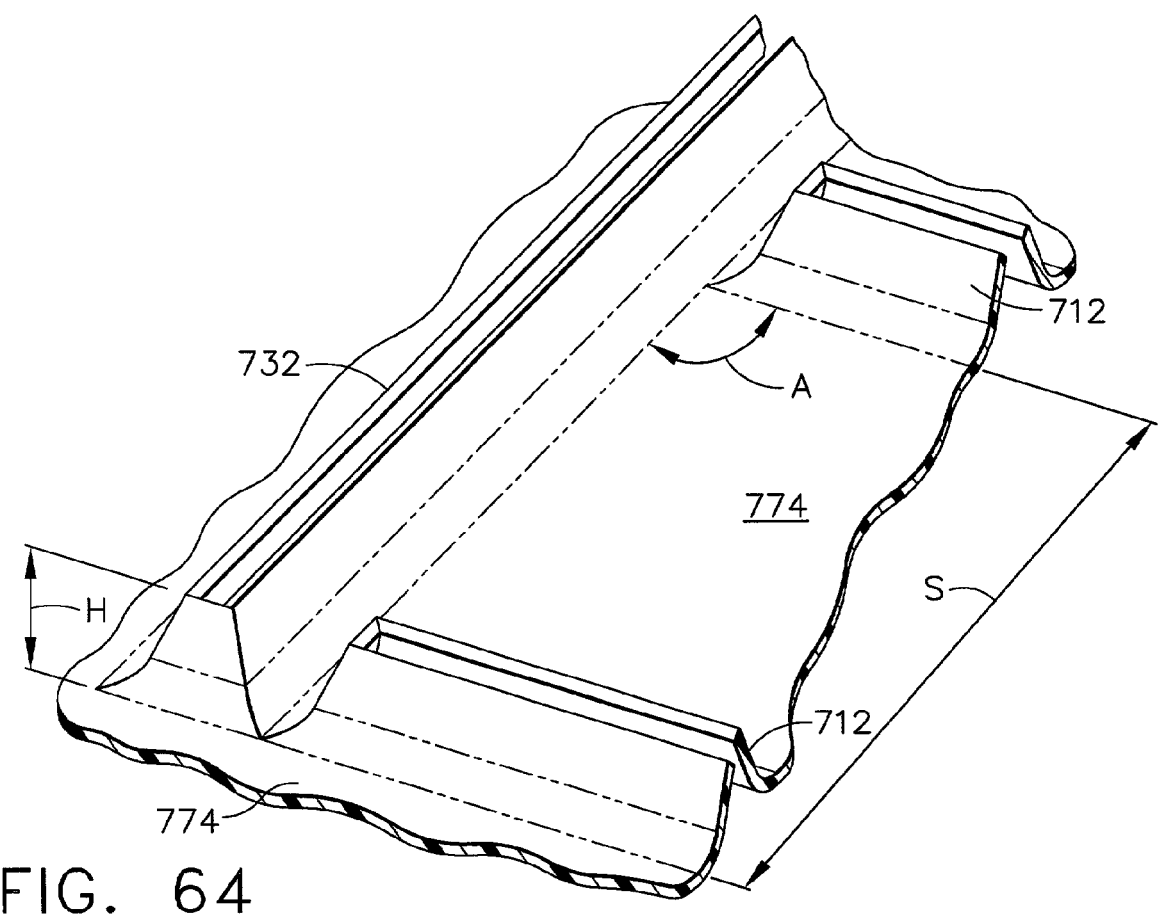
FIG. 64 is a perspective view of portions of a few of the mostly-rectangular microelements of FIG. 63.

FIG. 64 shows the same structure in a perspective view as illustrated in FIG. 63, in which one of the lengthier microelements 732 is closely abutted by two separate microelements 712. All of these microelements extend or protrude from a substrate 774. In FIG. 64, the spacing between the two microelements 712 is illustrated by the dimension "S" and the angular relationship between one of the microelements 712 and the illustrated microelement 732 is designated by the angle "A." These same dimensions also appear on FIG. 63. In addition, a dimension "H" is illustrated on FIG. 64 to represent the height of the microelement 732 with respect to the distance between its distal end (along its edge) and its base line where it meets the substrate 774.

Figure 65:
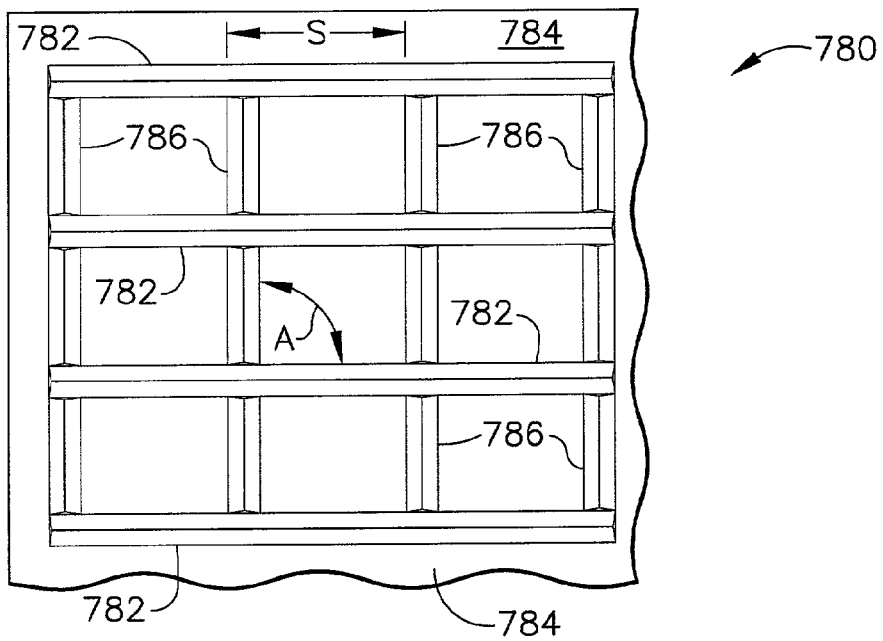
FIG. 65 is a plan view of an array of microelements similar to those of FIG. 63, which are mostly rectangular in shape but with sloped side walls and end walls, but without through-slots in the microelements, and which are arranged in a closed box-like array pattern, as constructed according to the principles of the present invention.
Figure 66:
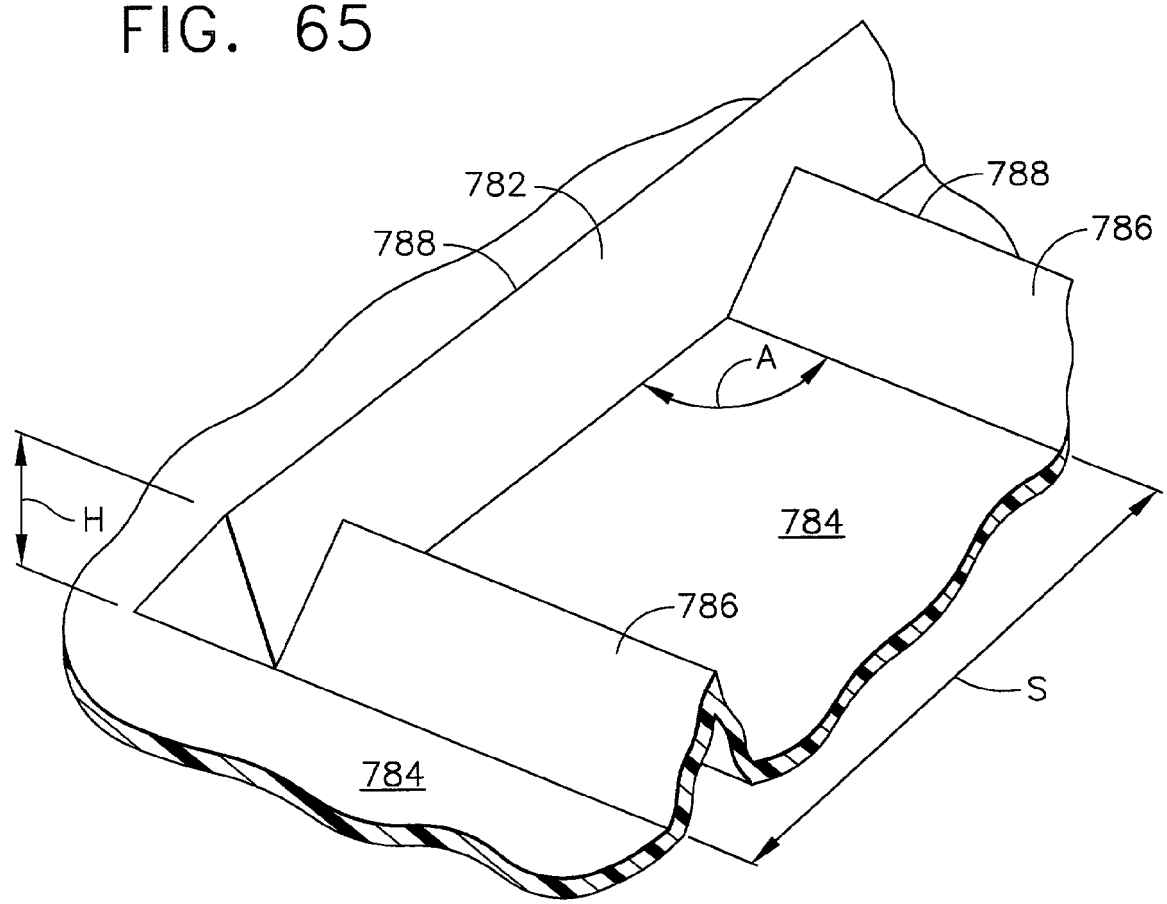
FIG. 66 is a perspective view of portions of a few of the mostly-rectangular microelements of FIG. 65.

It will be understood that the microstructure 770 could be fabricated of such microelements having various different spacings and angular relationships, as well as different heights of their microelements, all without departing from the principles of the present invention. Moreover, various shapes of microelements could be utilized in a continuous edged structure, including microstructures that have triangular shapes forming a top edge, such as illustrated in FIGS. 65 and 66, described below. Finally, it will be understood that the microelements that make up the microstructure 770 will preferably exhibit a substantially sharp edge, and thus will perform an exfoliation procedure when used on skin.

FIG. 65 illustrates another microstructure generally designated by the reference numeral 780 which includes several different microelements that provide at least one substantially continuous edge, similar to the microstructure 770 of FIG. 63. In FIG. 65, the microelements have a substantially "full" triangular cross-section, as can be seen in the perspective view of FIG. 66. In FIG. 65, the majority of the microelements are designated by a reference numeral 786, while there are also lengthier microelements designated by the reference numeral 782. These microelements are oriented in an angular relationship as designated by the angle "A," and the shorter microelements 786 have a spacing designated by the letter "S." The microelements 782 and 786 protrude from a substrate 784.

It will be understood that such microelements can be formed of virtually any angular relationship or spacing, as indicated by the angle A and spacing between the "short" microelements at S; additionally, the height of these microelements can also vary, as indicated by the height dimension "H." It should be noted that the substantially sharp edges along the top edges 788 of the triangular cross-section of the microelements 782 and 786 could potentially penetrate entirely through the stratum corneum of skin if the H dimension was made longer than, for example, 200 microns. This is in contrast to the microelements 732 and 712 illustrated in FIGS. 63 and 64, in which these slotted microelements that have dual edges along their longitudinal dimensions will virtually ensure that the skin will not be pierced in such a significant manner, regardless of the length of the height dimension H.

The radius of the top edges designated at the reference numerals 788 of these triangular cross-sectioned microelements 782 and 786 could be made "razor sharp" so as to provide a cutting edge with respect to performing an exfoliation operation. This radius can be controlled so that it would be less likely to actually pierce all the way through the stratum corneum of skin, even if the height dimension H is greater than 200 microns. Of course, the radius of the edges for the microstructures illustrated in FIGS. 40–76 can all be controlled, as desired to perform the beneficial effect of exfoliation. Moreover, the radius of the sharp tips in the embodiments illustrated in FIGS. 1–39 can also be controlled so as to perform exfoliation procedures, but not necessarily made so sharp as to literally pierce all the way through the stratum corneum.

FIGS. 67–70 illustrate various shapes of "inverted" microelements, which are still able to perform exfoliation operations if fabricated properly. In FIG. 67, an inverted microelement generally designated by the reference numeral 800 is illustrated as protruding downward from a substrate 804. The downward tip of the microelement is designated at 802, and the cutting edges are designated at the reference numerals 806. In this embodiment, the microstructure will be pressed against skin, in which the skin would touch the upper surface of the substrate 804, as illustrated on FIG. 67. The overall shape of the microelement 800 is very similar to that illustrated in FIG. 2 by the microelement 12. Of course, in FIG. 67, the microelement 800 is inverted with respect to its placement against skin. The cutting edges would indeed be the base of the pyramidal-shaped microelement 800, which correspond to the line segments 806 in this view. When using an inverted microelement, the dead skin cells and other matter would accumulate within the interior space 808 of the pyramidal-shaped microelement 800. This interior space 808 is also referred to herein as a substantially empty space within the microelements, regardless as to the actual shape or size of the microelements. The interior space 808 can function to collect, pack, and also limit exfoliation in a predetermined manner, thereby rendering this microstructure self-limiting.

FIG. 68 illustrates another pyramidal microelement generally designated by the reference numeral 810. This microelement 810 protrudes downward as seen in this view from a substrate 814, and exhibits a point 812 that is beneath the substrate in this view. The cutting edges are designated by the reference numeral 816, which also form the base lines of this pyramidal-shaped microelement 810. The main difference between the structures of FIGS. 67 and 68 are a set of through-holes 818, which are placed in the substrate 814 at locations that are somewhat adjacent to the microelement 810. By placing a fluidic material, such as a skin active, beneath the substrate 814 (as seen in FIG. 68) an exfoliation operation can be simultaneously carried out while the fluidic compound is placed upon the skin surface of the user. As in the microelement 800, there is a substantially empty space within the microelement 810 on FIG. 68.

Another inverted microelement is illustrated on FIG. 69, in which a triangular-shaped elongated microelement is designated by the reference numeral 820. Microelement 820 protrudes from the bottom of a substrate 824, and has a "tip" seen at the reference numeral 822, which actually represents a longitudinal edge along the bottommost region of this microelement 820 as seen in FIG. 69. The base lines of the microelement 820 make up the cutting edges, and are designated by the reference numerals 826 and 828. Reference numerals 826 represent the longer base lines in the longitudinal direction, while the reference numerals 828 represent the transverse base lines that are perpendicular thereto. In most respects, the overall shape of the microelement 820 is the same as the microelements 782 and 786 as seen on FIG. 66. Of course, on FIG. 69 the microelement is inverted, and the base lines 826 and 828 comprise the cutting edges for an exfoliation operation. As in the microelement 800, there is a substantially empty space within the microelement 820 on FIG. 69.

FIG. 70 shows another configuration of an inverted microelement that is generally designated by the reference numeral 830. Microelement 830 protrudes downward from a substrate 834, and instead of forming a tip or edge as was seen in the microelement 820 of FIG. 69, microelement 830 does not come to a single sharp edge, but instead has a through-slot at 832 formed therein. This slot 832 creates a pair of parallel sharp edges. If desired, however, these parallel edges may not necessarily be made extremely sharp since their radiuses can be controlled. In the inverted microelement 830, the true cutting edges are represented by the base lines 836 and 838, and thus the slot 832 does not necessarily need to form any type of sharp edges at all at its bottommost region.

The longer cutting edges 836 are run in the longitudinal direction of the microelement 830, whereas the shorter cutting edges 832 are substantially perpendicular and in a transverse direction in this embodiment. Both sets of cutting edges 836, 838 will preferably be substantially sharp so as to be able to perform an exfoliation operation when the top surface (as seen in FIG. 70) is pressed against skin and rubbed thereagainst. As in the microelement 820, there is a substantially empty space within the microelement 830 on FIG. 70; this empty space also forms the through-hole (or "slot" or "opening") 832 in microelement 830.

It will be understood that the metalization (or other coating material) can be applied to every structure described herein, including those depicted in FIGS. 67–70. It will be further understood that, if the substrate is made of a transparent material for any of these embodiments, then the metalization could be deposited on the reverse (or back) side of the microstructure, while still achieving the same visual feedback effect.

Figure 71:
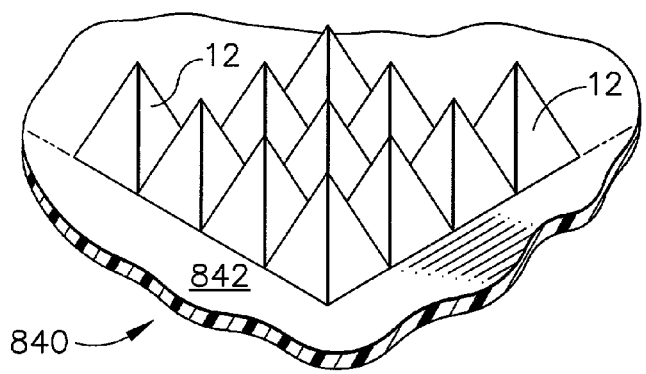
FIG. 71 is a perspective view of an array of very closely-packed microelements, in which each microelement is similar in appearance to the microelements seen in FIG. 2, as constructed according to the principles of the present invention.

FIGS. 71–76 illustrate several different shapes of microelements that are quite closely packed with one another, and thus have no intentional spaces between base lines of adjacent microelements. In other words, any spacing between side walls of adjacent microelements is substantially minimized. As seen in FIG. 71, an array of pyramidal microelements 12 (similar to that of FIG. 2) are placed upon a substrate 842, thereby forming a microstructure generally designated by the reference numeral 840. This microstructure 840 can be used in an exfoliation operation, in which the skin cells that are scraped by the microelements 12 will accumulate in the spaces between the tips and sloped side walls of the microelements 12.

If the upper surface (as seen on FIG. 71) is metalized, then there will be a visual feedback provided such that the reflectivity or "shininess" of the microelements will appear to become dull as the spaces between the pyramids 12 accumulate skin cells or other matter from a person's skin surface during exfoliation. It will be understood that, if the substrate is made of a transparent material, then the metalization could be deposited on the reverse (or lower) side of the microstructure, while still achieving the same visual feedback effect.

Figure 72:
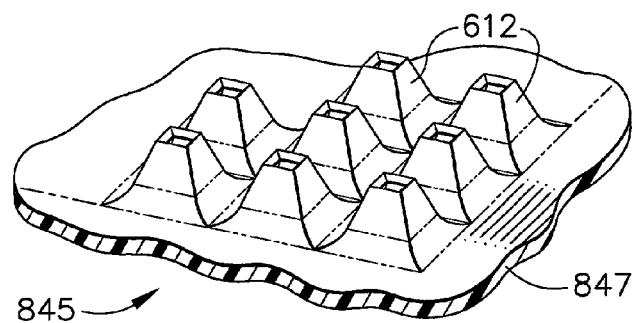
FIG. 72 is a perspective view of an array of very closely-packed microelements, in which each microelement is similar in appearance to the microelements seen in FIG. 41, as constructed according to the principles of the present invention.

FIG. 72 illustrates a microstructure generally designated by the reference numeral 845 in which multiple semi-pyramidal-shaped microelements 612 protrude from a substrate 847. The truncated (or partial) pyramidal microelements 612 are similar to those illustrated in FIGS. 40–42. Again, microelements 612 are very closely packed to one another, and have no intentional spacing between their base lines, yet they can accumulate skin cells between their uppermost regions, including between their sloped side walls. Since the individual microelements 612 incorporate a through-hole (see the through-hole 610 illustrated on FIG. 42), a skin active or other fluidic compound could be used to treat the skin after flowing through these through-holes from the bottom of the substrate 847. As described above, the upper surface of microstructure 845 could be metalized so as to provide a visual feedback if desired. It will be understood that, if the substrate is made of a transparent material, then the metalization could be deposited on the reverse (or lower) side of the microstructure, while still achieving the same visual feedback effect.

Figure 73:
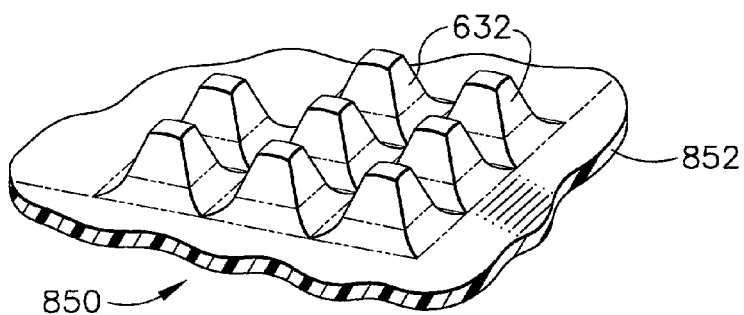
FIG. 73 is a perspective view of an array of very closely-packed microelements, in which each microelement is similar in appearance to the microelements seen in FIG. 44, as constructed according to the principles of the present invention.

FIG. 73 illustrates a microstructure 850 which incorporates a number of partially-pyramidal-shaped (e.g., truncated pyramids) microelements 632 that protrude from a substrate 852. These microelements 632 are similar to those illustrated in FIGS. 43–45. In FIG. 73, there are no through-holes in either the microelements 632 or in the substrate 852, and therefore, the microstructure 850 would be useful strictly for an exfoliation procedure. Of course, some type of fluid or solid compound could be placed on the surface of the skin and rubbed into the skin at the same time the microstructure 850 is rubbed against the same skin surface, thereby performing an exfoliation operation while also applying some type of skin active or other compound to the surface of the skin. The upper surface of microstructure 850 could be metalized so as to provide a visual feedback if desired. It will be understood that, if the substrate is made of a transparent material, then the metalization could be deposited on the reverse (or lower) side of the microstructure, while still achieving the same visual feedback effect.

Figure 74:
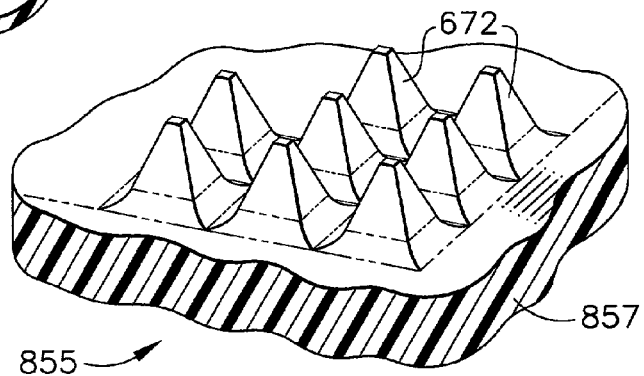
FIG. 74 is a perspective view of an array of very closely-packed microelements, in which each microelement is similar in appearance to the microelements seen in FIG. 50, as constructed according to the principles of the present invention.

FIG. 74 illustrates a microstructure generally designated by the reference numeral 855 which contains a number of partially-pyramidal-shaped (e.g., truncated pyramids) microelements 672, which protrude from a substrate 857. Microelements 672 are essentially the same as those illustrated in FIGS. 49–51. Again, there are no through-holes in the microelements 672 or in the substrate 857 in the embodiment illustrated on FIG. 74, and thus the microstructure 855 would be used for exfoliation. Of course, it could be used in conjunction with a separate fluidic compound that is placed upon the same surface of the skin that the exfoliation operation is also performed on by this microstructure. The upper surface of microstructure 855 could be metalized so as to provide a visual feedback if desired. It will be understood that, if the substrate is made of a transparent material, then the metalization could be deposited on the reverse (or lower) side of the microstructure, while still achieving the same visual feedback effect.

Figure 75:
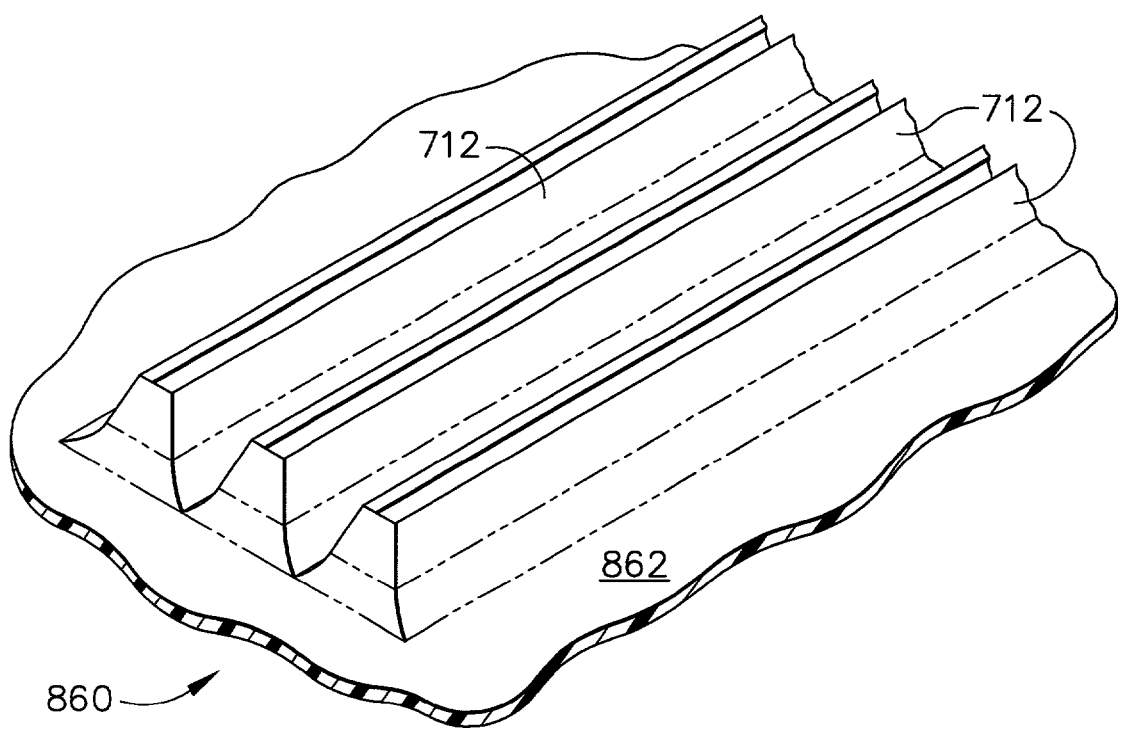
FIG. 75 is a perspective view of an array of very closely-packed microelements, in which each microelement is similar in appearance to the microelements seen in FIG. 56, as constructed according to the principles of the present invention.

FIG. 75 illustrates a microstructure generally designated by the reference numeral 860 which includes several parallel rectangular-shaped microelements 712 which protrude from a substrate 862. The microelements 712 are similar to those illustrated on FIGS. 55–58, and include a through-slot similar to the slot 716 illustrated on FIG. 58. By virtue of this slot, the microstructure 860 could be used for both exfoliation and simultaneously to apply a fluidic compound such as a skin active to the surface of the skin. The upper surface of microstructure 860 could be metalized so as to provide a visual feedback if desired. It will be understood that, if the substrate is made of a transparent material, then the metalization could be deposited on the reverse (or lower) side of the microstructure, while still achieving the same visual feedback effect.

Figure 76:
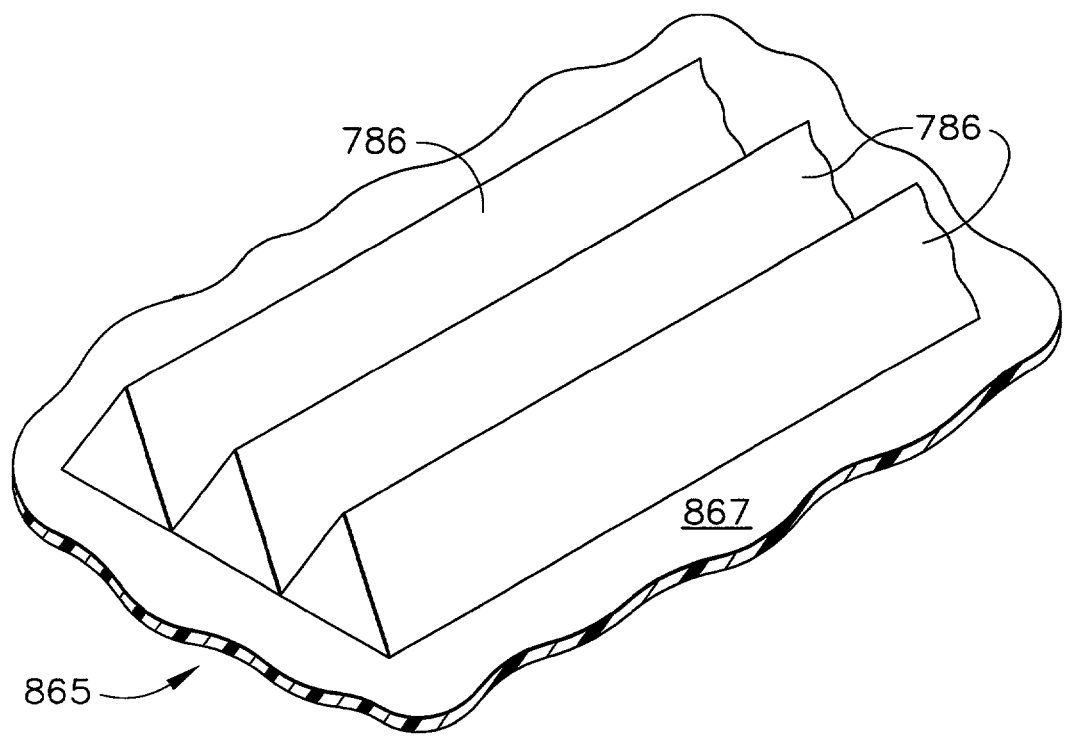
FIG. 76 is a perspective view of an array of very closely-packed microelements, in which each microelement is similar in appearance to the microelements seen in FIG. 66, as constructed according to the principles of the present invention.

FIG. 76 illustrates a microstructure generally designated by the reference numeral 865 which contains a number of parallel wedge-shaped microelements 786 that protrude from a substrate 867. These microelements 786 are similar to those illustrated on FIGS. 65 and 66, and have no through-holes or through-slots therewithin. Unless some type of through-holes are placed in the substrates 867, this microstructure 865 would be used for exfoliation only, although a fluidic compound such as a skin active could be placed upon the same skin surface that the microstructure 865 will be rubbed against, if desired. The upper surface of microstructure 865 could be metalized so as to provide a visual feedback if desired. It will be understood that, if the substrate is made of a transparent material, then the metalization could be deposited on the reverse (or lower) side of the microstructure, while still achieving the same visual feedback effect.

As can be seen from FIGS. 71–76, virtually all of these examples of microstructures can be closely spaced to one another, or "closely packed" as referred to above. It will be understood that the actual spacing between the base lines of the adjacent microelements can range from virtually zero distance to as large a separation as is desired to achieve the purposes of the microstructure designer for performing a particular application, such as exfoliation. While true "zero-spacing" may be virtually impossible, at the micron level, the distances between the base lines of individual microelements can approach zero. This actually may be easier to manufacture than attempting to have individual microelements that are separated by a substantially planar substrate surface. In all cases, the sloped side walls of the individual microelements will provide spaces in which skin cells and other material can accumulate during an exfoliation operation, which not only can accumulate skin cells, but also vellus hair and other substances such as dirt or makeup.

It will be understood that all of the microstructures of FIGS. 71–76 can be metalized or can have other non-metallic surfaces coated thereupon, which can affect the frictional characteristics of the microelements when placed against the skin, or the visual characteristics as a form of user feedback. All of these various coatings can be made without departing from the principles of the present invention. Moreover, it will be understood that shapes other than illustrated in the figures of this patent document could be utilized to perform exfoliation procedures without departing from the principles of the present invention, regardless as to whether the very closely-packed microelements are provided, or if there is intentional spacing between individual microelements upon the substrate.

It will be understood that the microstructures of FIGS. 40–70 could be laminated to a backing material as seen at 502 in FIG. 39, such as a non-woven material, without departing from the principles of the present invention. Such a backing material could be porous with respect to a fluid to be delivered (e.g., a skin active), or it could be impregnated with such a fluid.

In addition to skin cells that are removed by the microstructures of FIGS. 40–76, vellus hair can be removed at the same time, if desired. The vellus hair is very small in diameter, on the order of ten (10) microns, and thus is extremely difficult to see. Typically, vellus hair becomes visible only after makeup is applied to the skin. The microelements of the present invention can be made sufficiently small to cut the vellus hair during one of the exfoliation procedures described above. This can be quite useful, particularly for older women who tend to grow vellus hair on the sides of their faces, in that a single procedure of exfoliation will not only clean their skin, but also remove their vellus hair. If, for example, a metalized microstructure is used for this purpose, then the visual feedback will provide an indication that both skin cells and vellus hair have been removed.

The microstructures of FIGS. 1–76 can be made of a material and thickness so as to be quite flexible, if desired. In such a configuration, the microstructures could be used as a type of "sandpaper" with regard to "how" it could be applied to skin, although of course the shapes and sizes of the microelements would be quite different from grains of sand. The flexibility of the microstructures of the present invention can be much greater than that of normal sandpaper, thereby enabling a user to conform the microstructures to locations on their skin having a very tight radius, either inner or outer radius configurations. It will be understood that such flexible microstructures can nevertheless be metalized, thereby providing the visual feedback to the user described in the preceding paragraph.

The foregoing description of a preferred embodiment of the invention has been presented for purposes of illustration and description. It is not intended to be exhaustive or to limit the invention to the precise form disclosed. Obvious modifications or variations are possible in light of the above teachings. The embodiment was chosen and described in order to best illustrate the principles of the invention and its practical application to thereby enable one of ordinary skill in the art to best utilize the invention in various embodiments and with various modifications as are suited to the particular use contemplated. It is intended that the scope of the invention be defined by the claims appended hereto.

What is claimed is:

1. A method for removing cells from skin, said method comprising:
    (a) providing a microstructure having a substrate and a plurality of microelements, wherein a majority of said microelements are of at least one predetermined shape that includes at least one substantially sharp edge at a distal end of the microelements;
    (b) placing said microstructure on skin then rubbing the microstructure against said skin, thereby scraping and accumulating skin cells on said substrate in areas between said plurality of microelements, wherein said at least one predetermined shape of said majority of microelements does not create substantial focal discrete points of pressure on skin; and
    (c) withdrawing said microstructure from said skin, and thereby removing a large majority of said skin cells that have accumulated and are retained upon said substrate.

2. The method as recited in claim 1, wherein during said step of rubbing the microstructure against the skin, vellus hair is also removed along with skin cells.

3. The method as recited in claim 1, wherein said majority of microelements have a length and shape that tend to scrape skin cells loose without penetrating entirely through a stratum corneum layer of skin.

4. The method as recited in claim 1, wherein said microstructure is coated so as to act as a feedback indicator during use.

5. A method for removing cells from skin, said method comprising:
    (a) providing a microstructure having a substrate and a plurality of inverted microelements, wherein a majority of said microelements extends from a first surface of said substrate and which exhibit a substantially empty space within said microelements, and wherein said majority of microelements exhibits at least one substantially sharp edge along a second surface of said substrate, said second surface being opposite the first surface of said substrate;
    (b) placing the second surface of said microstructure on skin and then rubbing the microstructure against said skin, thereby scraping and accumulating skin cells within said substantially empty space within said majority of microelements; and
    (c) withdrawing said microstructure from said skin, and thereby removing a large majority of said skin cells that have accumulated and are retained within said substantially empty space within said majority of microelements.

6. The method as recited in claim 5, wherein said microstructure is coated so as to act as a feedback indicator during use.

7. A method for removing cells from skin, said method comprising:
   (a) providing a microstructure having a substrate and a plurality of microelements, wherein a majority of said microelements are of at least one predetermined size and shape, and each exhibit at least one side wall that extends above said first surface of the substrate, and wherein said majority of microelements are oriented in a closely-packed arrangement such that any spacing between portions of said side walls of adjacent microelements is substantially minimized;
   (b) placing said microstructure on skin then rubbing the microstructure against said skin, thereby scraping and accumulating skin cells in areas between said majority of microelements; and
   (c) withdrawing said microstructure from said skin, and thereby removing a large majority of said skin cells that have accumulated and are retained upon said microstructure.

8. The method as recited in claim 7, wherein said majority of microelements exhibits at least one substantially sharp edge and does not create substantial focal discrete points of pressure on skin.

9. The method as recited in claim 7, wherein said majority of microelements have a length and shape that tend to scrape skin cells loose without penetrating entirely through a stratum corneum layer of skin.

* * * * *